(12) United States Patent
Watanabe et al.

(10) Patent No.: US 8,232,420 B2
(45) Date of Patent: Jul. 31, 2012

(54) ASYMMETRIC CATALYST AND PROCESS FOR PREPARING OPTICALLY ACTIVE ALCOHOLS USING THE SAME

(75) Inventors: Masahito Watanabe, Saitama (JP); Junichi Hori, Saitama (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 193 days.

(21) Appl. No.: 12/758,257

(22) Filed: Apr. 12, 2010

(65) Prior Publication Data
US 2010/0261924 A1 Oct. 14, 2010

(30) Foreign Application Priority Data

Apr. 10, 2009 (JP) ................. 2009-096520

(51) Int. Cl.
C07F 15/00 (2006.01)
C07C 27/00 (2006.01)
C07C 303/00 (2006.01)
(52) U.S. Cl. .......... 556/137; 564/89; 568/700; 568/812; 568/814
(58) Field of Classification Search .................. 556/137; 568/700, 812, 814; 564/89
See application file for complete search history.

(56) References Cited

U.S. PATENT DOCUMENTS

| 5,763,688 | A | 6/1998 | Ikariya et al. |
| 6,184,381 | B1 | 2/2001 | Ikariya et al. |
| 2004/0082820 | A1 | 4/2004 | Torii et al. |
| 2008/0234525 | A1 | 9/2008 | Utsumi et al. |

FOREIGN PATENT DOCUMENTS

| GB | 2 451 190 | 1/2009 |
| JP | 2731377 B2 | 3/1998 |
| JP | 2962668 B2 | 10/1999 |
| JP | 11-335385 A | 12/1999 |
| JP | 3040353 B2 | 5/2000 |
| WO | WO 98/42643 A1 | 10/1998 |
| WO | WO 00/56332 A1 | 9/2000 |
| WO | WO 02/051781 A1 | 7/2002 |
| WO | WO 2004/024708 A2 | 3/2004 |
| WO | WO 2004/110976 | 12/2004 |
| WO | WO 2006/067395 A1 | 6/2006 |
| WO | WO 2006/137195 A1 | 12/2006 |
| WO | WO 2007/120824 A2 | 10/2007 |

OTHER PUBLICATIONS

Li, X. et al., "An Efficient Ir(III) Catalyst for the Asymmetric Transfer Hydrogenation of Ketones in Neat Water," *SYNLETT* 2006; 8:1155-1160.
Mashima, K. et al., "The Half-sandwich Hydride and 16-Electron Complexes of Rhodium and Iridium Containing (1S,2S)-N-(p-Toluenesulfonyl)-1,2-diphenylethylenediamine: Relevant to the Asymmetric Transfer Hydrogenation," *Chemistry Letters* 1998; 1201-1202.

Mashima, K. et al., "Asymmetric Transfer Hydrogenation of Ketonic Substrates Catalyzed by ($\eta^5$-C$_5$Me$_5$)MCl Complexes (M = Rh and Ir) of (1S,2S)-N-(p-Toluenesulfonyl)-1,2-diphenylethylenediamine," *Chemistry Letters* 1998; 1199-1200.
Murata, K. et al., "New Chiral Rhodium and Iridium Complexes with Chiral Diamine Ligands for Asymmetric Transfer Hydrogenation of Aromatic Ketones," *J. Org. Chem.* 1999; 64(7):2186-2187.
Ohkuma, T. et al., "The Hydrogenation/Transfer Hydrogenation Network: Asymmetric Hydrogenation of Ketones and Chiral $\eta^6$-Arene/N-Tosylethylenediamine-Ruthenium(II) Catalysts," *J. Am. Chem. Soc.* 2006; 128(27):8724-8725.
Ohkuma, T. et al., "Asymmetric Hydrogenation of α-Chloro Aromatic Ketones Catalyzed by $\eta^6$-Arene/TsDPEN-Ruthenium(II) Complexes," *Organic Letters* 2007; 9(2):255-257.
Ohkuma, T. et al., "Asymmetric Hydrogenation of α-Hydroxy Ketones Catalyzed by MsDPEN-Cp*Ir(III) Complex," *Organic Letters* 2007; 9(13):2565-2567.
Wu, X. et al., "Accelerated asymmetric transfer hydrogenation of aromatic ketones in water," *Org. Biomol. Chem.* 2004; 2:1818-1821.
Wu, X. et al., "A remarkably effective catalyst for the asymmetric transfer hydrogenation of aromatic ketones in water and air," *Chem. Commun.* 2005; 4447-4449.
Cheung, F.K. et al., "The use of a [4+2] cycloaddition reaction for the preparation of a series of 'tethered' Ru(II)-diamine and aminoalcohol complexes," *Org. Biomol. Chem.* 2007; 5:1093-1103.

*Primary Examiner* — Porfirio Nazario Gonzalez
(74) *Attorney, Agent, or Firm* — Wolf, Greenfield & Sacks, P.C.

(57) ABSTRACT

The present invention provides an organic metal compound, a ligand, an asymmetric catalyst, and a process for preparing optically-active alcohols using the asymmetric catalyst. The organic metal compound of the present invention is expressed by the following general formula (1):

(Chem. 1)

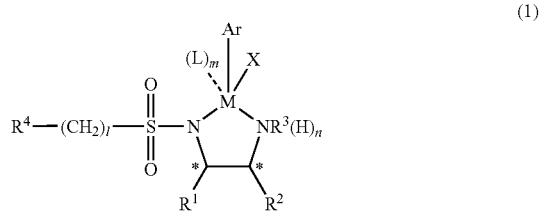

(1)

wherein in general formula (1), $R^1$ and $R^2$ are a mutually identical or mutually different, unsubstituted or substituted alkyl group, aryl group, cycloalkyl group, or $R^1$ and $R^2$ are bound to form an alicyclic ring, $R^3$ is a hydrogen atom or an alkyl group, $R^4$ is a branched alkyl group or an alkyl group that does or does not form a ring by itself, or an unsubstituted or substituted aryl group, or an unsubstituted or substituted heterocyclic group, Ar is an unsubstituted or substituted cyclopentadienyl group that is bound to M via a π bond, or an unsubstituted or substituted benzene, X is a hydride group or an anionic group, M is ruthenium, rhodium or iridium, L is a solvent molecule or a water molecule, l is 1 or 2, m is an integer from 0 to 2, n is 0 or 1, and when n is 0, X does not exist, and * represents asymmetric carbon, wherein $R^4$ is not a camphor group, a camphor derivative group, an isopropyl group or a phenyl group whenever $R^1$ and $R^2$ are both a phenyl group.

28 Claims, No Drawings

ASYMMETRIC CATALYST AND PROCESS FOR PREPARING OPTICALLY ACTIVE ALCOHOLS USING THE SAME

TECHNICAL FIELD

The present invention relates to an organic metal compound, a ligand, an asymmetric catalyst, and a process for preparing optically active alcohols using the asymmetric catalyst.

BACKGROUND ART

To date, various preparation processes of optically-active alcohols using metal complexes as a catalyst have been reported. In particular, processes in which optically-active alcohols are synthesized from ketone compounds by a reductive process using ruthenium complexes as a catalyst under the presence of base have been actively investigated. These processes are classified into "asymmetric hydrogenation" wherein hydrogen is used as a hydrogen source, and "asymmetric reduction" wherein organic substances and metal hydrides are used as a hydrogen source; their characteristics are as follows.

With respect to asymmetric hydrogenation wherein optically-active alcohols are obtained from ketones by asymmetric hydrogenation using hydrogen as a reducing agent, and to catalysts used therein, for example, JP No. 2731377 reports a case wherein an optically-active alcohol was prepared by hydrogenation of a ketone compound under the presence of base, using a catalyst consisting of a complex in which BINAP (2,2'-bis(diphenylphosphino)-1,1'-binaphthyl) and DMF are coordinated to ruthenium and of a diphenylethylenediamine ligand. While this catalyst had an extremely high activity, it had problems regarding the applicability to ketone substrates, namely, that the hydrogenation reaction did not progress efficiently or the enantiomeric excess was insufficient depending on the structure of the ketone compound. Therefore, catalysts with different structures have been developed with the aim of expanding the range of applicable ketone substrates.

For example, reactions of α-chloroketones (Org. Lett. Vol. 9, p. 255 (2007)) and 4-chromanone (J. Am. Chem. Soc. Vol. 128, p. 8724 (2006)) using a ruthenium catalyst having TsDPEN (N-(p-toluenesulfonyl)-1,2-diphenylethanediamine) as a ligand, and asymmetric hydrogenation of α-hydroxyketone using an iridium catalyst having MsDPEN (N-methanesulfonyl-1,2-diphenylethanediamine) as a ligand (WO 2006/137195, Org. Lett. Vol. 9, p. 2565 (2007)) have been reported. With these catalyst systems, there is no need to add bases, so that the kind of ketone substrates that can be used for reactions has been expanded. However, there are still many ketone substrates with which hydrogenation is difficult. In addition, these catalyst systems are easily affected by slight amounts of impurities contained in ketone substrates, which is problematic when actual industrial application is considered.

Meanwhile, asymmetric reduction systems have been developed to obtain optically-active alcohols by asymmetric reduction of ketones using organic substances such as formate and sodium formate as a hydrogen source. Since these catalyst systems do not use hydrogen gas, and do not require a pressure-resistant container, there is only a few limitation in production equipments; therefore, a number of reports have been published. In particular, in cases of asymmetric ruthenium catalysts that have a diamine ligand having a sulfonyl amide group as an anchor (JP No. 2962668), since a wide range of ketones can be asymmetrically reduced compared to hydrogenation catalysts, their performance is particularly notable. There are also several reports on rhodium catalysts and iridium catalysts that have a diamine ligand with the same structure (WO 98/42643, JP A No. 11-335385, Chem. Lett. p. 1199 (1998), Chem. Lett. p. 1201 (1998), J. Org. Chem. Vol. 64, p. 2186 (1999)). These rhodium and iridium catalysts have characteristic catalytic performances, and they are reported to exhibit significant effects on asymmetric reduction of imines (WO 00/56332) and α-haloketone (WO 2002/051781).

With respect to reactions wherein formate is used as a hydrogen source, there are reports on asymmetric reduction of aromatic ketones such as acetophenones, indanone and acetonaphtone under the presence of asymmetric ruthenium catalyst (Org. Biomol. Chem. Vol. 2, p. 1818 (2004)), and asymmetric reduction of ketones using asymmetric rhodium and iridium catalysts (Chem. Commun. p. 4447 (2005)).

With these catalyst systems however, catalytic performance such as catalytic efficiency and enantioselectivity in most cases were lower than those of hydrogenation catalysts, causing a significant problem. In cases where formate is used, problems of catalytic efficiency and substrate specificity have been resolved to some extent, but enantioselectivity is hardly improved.

To solve the above-mentioned various problems of asymmetric reduction catalyst systems, improvement of catalytic structure has been investigated. As a complex having CsDPEN (N-camphorsulfonyl-1,2-diphenylethylenediamine) as a ligand, JP. No. 3040353 discloses a ruthenium complex, and JP. A. No. 11-335385 discloses a rhodium complex and an iridium complex. An example wherein a complex having CsDPEN as a ligand is applied to the preparation of a duloxetine derivative has been disclosed (WO 2004/024708). In addition, a reaction wherein formate is used as a hydrogen source and a rhodium or iridium complex having a CsDPEN ligand is used as a catalyst has been reported in WO 2006/067395 and Synlett p. 1155 (2006). With these methods using CsDPEN complexes, the enantioselectivity has been improved compared to conventional hydrogen-transfer catalysts; however, in some cases the enantioselectivity is not sufficient depending on the structure of substrates. One such example includes a case of preparation of 3',5'-bis(trifluoromethyl)acetophenone by means of two-phase asymmetric reduction using Cp*RhCl(Csdpen) as a catalyst and sodium formate as a hydrogen source; here, its optical purity is at the highest 83.0% ee (WO 2006/067395).

In the case of 2'-methoxyacetophenone, even when it was prepared by two-phase asymmetric reduction using Cp*IrCl (Csdpen) (Cp represents cyclopentadienyl group) as a catalyst and sodium formate as a hydrogen source, its optical purity was at the highest 85.0% ee (Synlett p. 1155 (2006)). Moreover, applicable substrates in these reports are limited to acetophenones having a substituent, and the range of applicable ketone substrates is not expanded. In addition, because camphor groups are an optically-active substance, it is difficult and costly to obtain a large amount of camphor groups. In addition, since CsDPEN has three asymmetric sites, its cost as a ligand and a complex becomes rather expensive, directly resulting in an increase in the cost of preparation process of optically-active alcohols, so that the industrial utility of this catalyst has been largely limited.

Other than those described above, WO 2007/120824 describes, as a catalyst used for the reduction of ketones in the synthesis of ezetimibe, a catalyst (Example 30) wherein [RuCl$_2$(p-cymene)]$_2$ and (S,S)-Bn-SO$_2$-DPEN are combined, and a catalyst (Example 48) wherein [RuCl$_2$(mesitylene)]$_2$ and (S,S)-i-Bu-SO$_2$-DPEN are combined. However, the applicable substrate range of these catalysts is narrow, and their enantioselectivity is low compared to CsDPEN complexes; accordingly, they are not sufficient for the application to the industrial preparation of optically-active alcohols.

As described above, with respect to the asymmetric hydrogenation catalysts which have been reported to date, the structure of applicable ketone substrates has been significantly limited; with respect to the asymmetric reduction catalysts, while the kind of applicable ketone substrates has been fairly expanded, it is not yet sufficient and their catalytic efficiency is problematic. CsDPEN complex catalysts which have been developed to overcome such problems are also practically insufficient in terms of cost and catalytic performance. Accordingly, the development of an inexpensive catalyst that can convert, with high enantioselectivity and high efficiency, ketones having various functional groups into optically-active alcohols, as well as a process for the preparation using said catalyst, have been desired.

CITATION LIST

Patent Literature

[Patent Literature 1] JP No. 2731377
[Patent Literature 2] WO 2006/137195
[Patent Literature 3] JP No. 2962668
[Patent Literature 4] WO 98/42643
[Patent Literature 5] JP A No. 11-335385
[Patent Literature 6] WO 00/56332
[Patent Literature 7] WO 2002/051781
[Patent Literature 8] JP No. 3040353
[Patent Literature 9] WO 2004/024708
[Patent Literature 10] WO 2006/067395
[Patent Literature 11] WO 2007/120824

Non Patent Literature

[Non Patent Literature 1] J. Am. Chem. Soc. Vol. 128, p. 8724 (2006)
[Non Patent Literature 2] Org. Lett. Vol. 9, p. 255 (2007)
[Non Patent Literature 3] Org. Lett. Vol. 9, p. 2565 (2007)
[Non Patent Literature 4] Chem. Lett. p. 1199 (1998)
[Non Patent Literature 5] Chem. Lett. p. 1201 (1998)
[Non Patent Literature 6] J. Org. Chem. Vol. 64, p. 2186 (1999)
[Non Patent Literature 7] Org. Biomol. Chem. Vol. 2, p. 1818 (2004)
[Non Patent Literature 8] Chem. Commun. p. 4447 (2005)
[Non Patent Literature 9] Synlett p. 1155 (2006)

SUMMARY OF INVENTION

Technical Problem

Therefore, the object of the present invention is to provide a catalyst used for enentioselective preparation of optically-active alcohols having various industrially-effective functional groups, in industrial preparation of optically-active alcohols by means of catalytic asymmetric hydrogenation or reduction of ketones, and to provide a method to carry out highly efficient, i.e., low-cost preparation of optically-active alcohols by an easily-obtainable catalyst using a simple reaction apparatus.

Solution to Problem

In order to solve the above-mentioned problems, the present inventors have found that, from their devoted research on structure and performance of catalysts, a complex having a methylene group at the position adjacent to a sulfonyl group (—SO$_2$—) has a catalytic activity superior than that of CsDPEN complexes, and in addition, it exhibits the same or higher level of enantioselectivity. Furthermore, while CsDPEN complex catalysts show not a light degree of substrate specificity, the inventive complex catalyst shows adaptability to ketones with a wide range of structures. Moreover, the inventors have found that the inventive complex catalyst exhibits superior catalytic performance and substrate adaptability in two-phase reduction using formate as a hydrogen source and water, and thus accomplished the present invention.

Namely, the present invention relates to an organic metal compound of general formula (1):

(Chem. 1)

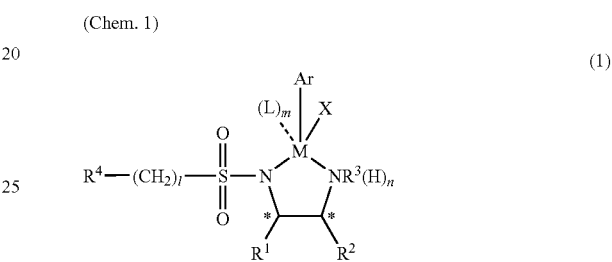

wherein in general formula (1), R$^1$ and R$^2$ are a mutually identical or mutually different, unsubstituted or substituted alkyl group, aryl group, or cycloalkyl group, or R$^1$ and R$^2$ are bound to form an alicyclic ring, R$^3$ is a hydrogen atom or an alkyl group, R$^4$ is an alkyl group that is branched or that does or does not form a ring by itself, an unsubstituted or substituted aryl group, or an unsubstituted or substituted heterocyclic group, Ar is an unsubstituted or substituted cyclopentadienyl group that is bound to M via a π bond, or an unsubstituted or substituted benzene, X is a hydride group or an anionic group, M is ruthenium, rhodium or iridium, L is a solvent molecule or a water molecule, l is 1 or 2, m is an integer from 0 to 2, n is 0 or 1, and when n is 0, X does not exist, and * represents asymmetric carbon, wherein R$^4$ is not a camphor group, a camphor derivative group, an isopropyl group or a phenyl group whenever R$^1$ and R$^2$ are both a phenyl group.

In addition, the present invention relates to the above organic metal compound, wherein in general formula (1), R$^4$ is an unsubstituted or substituted aryl group, or an unsubstituted or substituted heterocyclic group.

Furthermore, the present invention relates to the above organic metal compound, wherein in general formula (1), M is ruthenium and Ar is an unsubstituted or substituted benzene.

In addition, the present invention relates to the above organic metal compound, wherein in general formula (1), M is iridium and Ar is an unsubstituted or substituted cyclopentadienyl group.

Furthermore, the present invention relates to the above organic metal compound, wherein in general formula (1), R$^3$ is a hydrogen atom, n is 1, and X is a sulfonate group.

In addition, the present invention relates to the above organic metal compound, wherein in general formula (1), R$^3$ is a hydrogen atom, n is 1, and X is a halogen atom.

Furthermore, the present invention relates to a compound of general formula (2):

(Chem. 2)

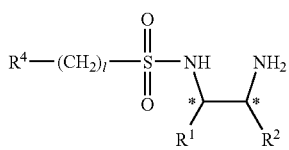

(2)

wherein in general formula (2), $R^1$ and $R^2$ are a mutually identical or mutually different, unsubstituted or substituted alkyl group, aryl group, or cycloalkyl group, or $R^1$ and $R^2$ are bound to form an alicyclic ring, $R^4$ is an unsubstituted or substituted C4-C15 alkyl group that is branched or that does or does not form a ring by itself, and that does not have a multiple bond and a hetero atom, or an unsubstituted or substituted aryl group, or an unsubstituted or substituted heterocyclic group, l is 1 or 2, * represents asymmetric carbon, wherein $R^4$ is not a camphor group, a camphor derivative group, an isopropyl group or a phenyl group whenever $R^1$ and $R^2$ are both a phenyl group.

In addition, the present invention relates to the above compound, wherein in general formula (2), $R^4$ is an unsubstituted or substituted aryl group, or an unsubstituted or substituted heterocyclic group.

Furthermore, the present invention relates to a catalyst comprising a compound of general formula (2):

(Chem. 3)

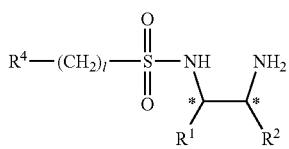

(2)

wherein in general formula (2), $R^1$ and $R^2$ are a mutually identical or mutually different, unsubstituted or substituted alkyl group, aryl group, or cycloalkyl group, or $R^1$ and $R^2$ are bound to form an alicyclic ring, $R^4$ is an unsubstituted or substituted C4-C15 alkyl group that is branched or that does or does not form a ring by itself, and that does not have a multiple bond and a hetero atom, or an unsubstituted or substituted aryl group, or an unsubstituted or substituted heterocyclic group, l is 1 or 2, * represents asymmetric carbon, wherein $R^4$ is not a camphor group, a camphor derivative group, an isopropyl group or a phenyl group whenever $R^1$ and $R^2$ are both a phenyl group,
and an organic metal compound of general formula (3):

$$(ArMX_2)_2 \quad (3)$$

wherein in general formula (3), Ar is an unsubstituted or substituted cyclopentadienyl group that is bound to M via a π bond, or an unsubstituted or substituted benzene, X is a hydride group or an anionic group, M is ruthenium, rhodium or iridium.

In addition, the present invention relates to the above catalyst, wherein in general formula (2), $R^4$ is an unsubstituted or substituted aryl group, or an unsubstituted or substituted heterocyclic group.

Furthermore, the present invention relates to a process for preparing optically active alcohols, wherein a ketone substrate and a hydrogen donor are reacted under the presence of the organic metal compound of general formula (1).

In addition, the present invention relates to a process for preparing optically active alcohols, wherein a ketone substrate and a hydrogen donor are reacted under the presence of a catalyst comprising the organic compound of general formula (2) and the organic metal compound of general formula (3).

Furthermore, the present invention relates to the above process, wherein hydrogen gas is used as the hydrogen donor.

In addition, the present invention relates to the above process, wherein a mixture of formic acid and organic amine is used as the hydrogen donor.

Furthermore, the present invention relates to the above process, wherein a formate is used as the hydrogen donor and in addition, water or water/organic solvent is used as the solvent.

In addition, the present invention relates to the above process, wherein a phase-transfer catalyst is further added.

Furthermore, the present invention relates to the above process, wherein an aromatic ketone having a substituent at 2'-position of the benzene ring is used as the substrate.

In addition, the present invention relates to the above process, wherein an aromatic ketone having a plurality of substituents in the benzene ring is used as the substrate.

In addition, the present invention relates to the above process, wherein bis(trifluoromethyl)acetophenone is used as the substrate.

Furthermore, the present invention relates to the above process, wherein 3',5'-bis(trifluoromethyl)acetophenone is used as the substrate.

Advantageous Effects of Invention

When the organic metal compound of the present invention is used as a catalyst, ketone substrates having various functional groups can be efficiently converted to optically-active alcohols and highly-pure optically-active alcohols can be obtained. Namely, even in the case of substrates which show insufficient enantioselectivity and insufficient catalytic efficiency by ruthenium, rhodium or iridium catalysts having a CsDPEN ligand, which are known to be the most high-performance catalysts, these substrates can be efficiently and enantioselectively converted to optically-active alcohols by using the organic metal compound of the present invention. Thus, the organic metal compound of the present invention can be used for the preparation of optically-active alcohols used as synthetic intermediates of medical, agrichemical and a numbers of general-purpose chemical substances. Furthermore, the inventive catalyst itself is inexpensive, different from expensive catalysts having an optically-active site such as a camphor group, so that together with the high catalytic efficiency, the inventive catalyst enables to decrease the cost of hydrogenation and reduction reactions, realizing low-cost production of optically-active alcohols.

In addition, in most of catalytic asymmetric reactions, catalytic reactions are usually affected by slight amounts of impurities existing in ketone substrates; however, when asymmetric reduction is carried out using the catalyst according to the present invention and using a formate as a hydrogen donor, even if a commercially-available ketone substrate is, used without purification, the reaction is not inhibited and objective optically-active alcohols can be obtained at a high yield.

DESCRIPTION OF EMBODIMENTS

An organic metal compound of the present invention that can be used as an organic metal catalyst is expressed by the following general formula (1), and an asymmetric ligand of the invention is expressed by the following general formula (2), and an organic metal compound that can constitute a catalyst by a combination with the asymmetric ligand of general formula (2) is expressed by general formula (3). Here, in the following general formulae, l is 1 or 2, m is from 0 to 2, n is 0 or 1, and when n is 0, X does not exist, and * represents asymmetric carbon.

[Chem. 4]

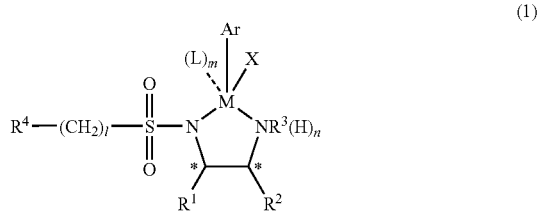

(1)

[Chem. 5]

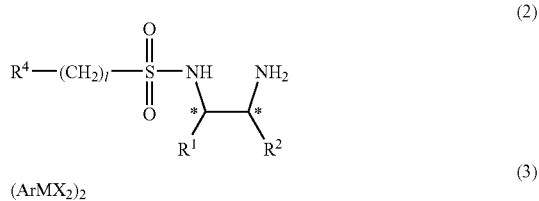

(2)

$(ArMX_2)_2$ (3)

$R^1$ and $R^2$ in general formulae (1) and (2) may be identical or different each other, and are an alkyl group, an aryl group, or a cycloalkyl group, which may have a substituent, or $R^1$ and $R^2$ are bound to form an alicyclic ring. Examples of alkyl group include C1-C10 alkyl groups such as methyl group, ethyl group, n-propyl group, isopropyl group, n-butyl group, sec-butyl group, and tert-butyl group. Examples of aryl group include phenyl group, naphthyl group, etc. Examples of cycloalkyl group include cyclopentyl group, cyclohexyl group, etc. Examples of alicyclic group formed by binding $R^1$ and $R^2$ that may have a substituent include cyclopentane ring and cyclohexane ring formed by binding $R^1$ and $R^2$. Examples of substituent for the above $R^1$ and $R^2$ include methyl group, ethyl group, isopropyl group, etc. One or more these substituents may be present.

$R^3$ in general formula (1) is a hydrogen atom or an alkyl group, and specific examples of alkyl group include C1-C5 alkyl groups such as methyl group, ethyl group, 1-propyl group, 2-propyl group, 1-butyl group, 2-butyl group, tert-butyl group, 1-pentyl group, 2-pentyl group, 3-pentyl group, cyclopentyl group, 2,2-dimethylpropyl group, etc. $R^3$ is preferably a hydrogen atom.

$R^4$ in general formula (1) is an alkyl group that may have a substituent, and that may be branched or may form a ring by itself, or an aryl group that may have a substituent, or a heterocyclic group that may have a substituent.

Specific examples of alkyl group that may have a substituent and that may be branched or may form a ring by itself include alkyl groups that may be branched such as methyl group, ethyl group, 1-propyl group, 2-propyl group, 1-butyl group, 2-butyl group, isobutyl group, tert-butyl group, 1-pentyl group, 2-pentyl group, 3-pentyl group, cyclopentyl group, 2,2-dimethylpropyl group, 3,3-dimethyl-2-butyl group, 3-methyl-2-pentyl group, 1-hexyl group, 2-hexyl group, 3-hexyl group, cyclohexyl group, 2,6-dimethyl-4-heptyl group, 2-methylcyclopentyl group, 3-methylcyclopentyl group, 2-ethylbutyl group, 1-heptyl group, 2-heptyl group, 3-heptyl group, 4-heptyl group, cycloheptyl group, 2,4-dimethyl-3-pentyl group, 1-octyl group, 2-octyl group, 3-octyl group, 4-octyl group, 4-nonyl group, 5-nonyl group, etc., or alkyl groups that my form a ring by themselves such as cyclopentyl group, cyclohexyl group, cycloheptyl group, etc. Of these alkyl groups, from the viewpoint of enantioselectivity of catalytic reaction, 3-pentyl group, tert-butyl group, 4-heptyl group, cyclopentyl group, cyclohexyl group, cycloheptyl group, etc. are preferred.

Examples of substituent for the above alkyl groups include methyl group, ethyl group, isopropyl group, etc. One or more these substituents may be present.

Examples of aryl group represented by $R^4$ that may have a substituent include phenyl group, naphthyl group, fluorenyl group, indenyl group, anthracenyl group, etc.

Of these aryl groups, from the viewpoint of enantioselectivity of catalytic reaction, phenyl group, naphthyl group, etc. are preferred.

Examples of substituent for aryl groups include methyl group, ethyl group, 1-propyl group, 2-propyl group, 1-butyl group, 2-butyl group, isobutyl group, tert-butyl group, 1-pentyl group, 2-pentyl group, 3-pentyl group, cyclopentyl group, 1-hexyl group, 2-hexyl group, 3-hexyl group, cyclohexyl group, halogen (F, Br, Cl, I), amino group, dimethylamino group, cyano group, trifluoromethyl group, trimethylsilyl group, hydroxyl group, alkoxy group (methoxy group, ethoxy group, propoxy group, phenoxy group, etc.), alkoxymethyl group, nitro group, phenyl group, etc.

Of these substituents for aryl groups, from the viewpoint of enantioselectivity of catalytic reaction, methyl group, methoxy group, phenoxy group, nitro group, ethyl group, isopropyl group, etc. are preferred. One or more these substituents may be present.

Specific examples of aryl groups that may have a substituent include phenyl groups that may have a substituent such as phenyl group, 2'-methylphenyl group, 3'-methylphenyl group, 4'-methylphenyl group, 2'-isopropylphenyl group, 3'-isopropylphenyl group, 4'-isopropylphenyl group, 2'-tert-butylphenyl group, 3'-tert-butylphenyl group, 4'-tert-butylphenyl group, 2'-ethylphenyl group, 3'-ethylphenyl group, 4'-ethylphenyl group, 2',6'-dimethylphenyl group, 2',4'-dimethylphenyl group, 3',5'-dimethylphenyl group, 2',5'-dimethylphenyl group, 2',6'-diethylphenyl group, 2',4'-diethylphenyl group, 3',5'-diethylphenyl group, 2',5'-diethylphenyl group, 2',4',6'-trimethylphenyl group, 2',4',6'-triethylphenyl group, 2',3',4',5',6'-pentamethylphenyl group, 2',3',5',6'-tetramethylphenyl group, 2',6'-diisopropylphenyl group, 3',5'-diisopropylphenyl group, 2',4',6'-triisopropylphenyl group, 3',5'-di-tert-butylphenyl group, 2',3',4',5',6'-pentafluorophenyl group, 2'-chlorophenyl group, 3'-chlorophenyl group, 4'-chlorophenyl group, 2',6'-dichlorophenyl group, 2',4'-dichlorophenyl group, 3',5'-dichlorophenyl group, 2',5'-dichlorophenyl group, 2',4',6'-trichlorophenyl group, 2'-fluorophenyl group, 3'-fluorophenyl group, 4'-fluorophenyl group, 2'-cyanophenyl group, 3'-cyanophenyl group, 4'-cyanophenyl group, 2'-aminophenyl group, 3'-aminophenyl group, 4'-aminophenyl group, 2',6'-diaminophenyl group, 3',5'-diaminophenyl group, 2'-dimethylaminophenyl group, 3'-dimethylaminophenyl group, 4'-dimethylaminophenyl group, 2',6'-dimethylaminophenyl group, 3',5'-dimethylaminophenyl group, 2'-methoxyphenyl group, 3'-methoxyphenyl group, 4'-methoxyphenyl group, 2',6'-dimethoxyphenyl group, 2',4'-dimethoxyphenyl group, 3',5'-dimethoxyphenyl group, 2',5'-dimethoxyphenyl group, 2',4',6'-trimethoxyphenyl group, 2'-trifluoromethyl phenyl group, 3'-trifluoromethyl phenyl group, 4'-trifluoromethyl phenyl group, 2',6'-ditrifluoromethyl phenyl group, 3',5'-ditrifluorophenyl phenyl group, 2'-nitrophenyl group, 3'-nitrophenyl group, 4'-nitrophenyl group, 2',6'-dinitrophenyl group, 2',4'-dinitrophenyl group, 3',5'-dinitrophenyl group, 2',5'-dinitrophenyl group, 2',4',6'-trinitrophenyl group, 2'-phenylphenyl group, 3'-phenylphenyl group, 4'-phenylphenyl group, 2',6'-diphenylphenyl group, 2',4'-diphenylphenyl group, 3',5'-diphenylphenyl group, 2',5'-diphenylphenyl group, 2'-phenoxyphenyl group, 3'-phenoxyphenyl group, 4'-phenoxyphenyl group, 2',6'-diphenoxyphenyl group, 2',4'-diphenoxyphenyl group, 3',5'-diphenoxyphenyl group, 2'-hydroxyphenyl group, 3'-hydroxyphenyl group, 4'-hydroxyphenyl group, 2',6'-dihydroxyphenyl group, 3',5'-dihydroxyphenyl group, 2',4',6'-trihydroxyphenyl group, 4'-trimethylsilylphenyl group, 3',5'-ditrimethylsilyl phenyl group, 2',5'-diphenoxyphenyl group, etc., and naphtyl groups that may have a substituent such as 1-naphthyl group, 2-naphthyl group, etc., and fluorenyl group, indenyl group, and anthracenyl group, etc.

Of these groups, 2',6'-dimethylphenyl group, 3',5'-dimethylphenyl group, 2',4',6'-trimethylphenyl group, 2',3',4',5',6'-pentamethylphenyl group, 3',5'-dimethoxyphenyl group, 2'-phenoxyphenyl group, 1-naphtyl group, etc. are preferred.

Examples of heterocyclic group represented by $R^4$ that may have a substituent include heterocyclic groups such as thienyl group, pyridyl group, furanyl group, tetrahydrofuranyl group, pyrrole group, picolyl group, etc. Of these heterocyclic groups, from the viewpoint of easiness in the synthesis of ligand, thienyl group, pyridyl group, etc. are preferred.

Examples of substituent of the above heterocyclic groups include the above-described substituents for the aryl groups.

Particularly preferable examples of the groups represented by $R^4$ in general formula (1) include, from the viewpoint of enantioselectivity in asymmetric reduction or asymmetric hydrogenation, tert-butyl group, 3-pentyl group, 4-heptyl group, cyclopentyl group, cyclohexyl group, cycloheptyl group, 2'-nitrophenyl group, 2',6'-dimetylphenyl group, 3',5'-dimetylphenyl group, 3',5'-dimethoxyphenyl group, 2',4',6'-trimethylphenyl group, 2',3',4',5',6'-pentamethylphenyl group, 2'-phenoxyphenyl group, 1-naphthyl group, etc.

In the compound of general formula (1), when M is ruthenium, Ar is preferably a benzene that may have a substituent; when M is iridium or rhodium, Ar is preferably a cyclopentadienyl group that may have a substituent.

The compounds of general formulae (1) and (2) of the present invention do not include the compounds wherein $R^4$ is a camphor group, camphor derivative group (7,7-dimethyl-2-hydroxybicyclo[2,2,1]hept-1-yl group, etc.), isopropyl group or phenyl group whenever $R^1$ and $R^2$ are both a phenyl group.

$R^4$ in general formula (2) may have a substituent, and may be branched or may form a ring by itself, and is a C4-C15 alkyl group that does not have a multiple bond and a heteroatom, an aryl group that may have a substituent, or a heterocyclic group that may have a substituent.

Specific examples of the alkyl group include 1-butyl group, 2-butyl group, tert-butyl group, 1-pentyl group, 2-pentyl group, 3-pentyl group, cyclopentyl group, 2,2-dimethylpropyl group, 3,3-dimethyl-2-butyl group, 3-methyl-2-pentyl group, 1-hexyl group, 2-hexyl group, 3-hexyl group, cyclohexyl group, 2,6-dimethyl-4-heptyl group, 2-methylcyclopentyl group, 3-methylcyclopentyl group, 2-ethylbutyl group, 1-heptyl group, 2-heptyl group, 3-heptyl group, 4-heptyl group, cycloheptyl group, 2,4-dimethyl-3-pentyl group, 1-octyl group, 2-octyl group, 3-octyl group, 4-octyl group, 4-nonyl group, 5-nonyl group, etc. Of these alkyl groups, from the viewpoint of enantioselectivity of catalytic reaction, tert-butyl group, 4-heptyl group, cyclopentyl group, cyclohexyl group, cycloheptyl group, etc. are preferred.

Examples of substituent of the above alkyl groups include methyl group, ethyl group, isopropyl, etc. One or more these substituents may be present.

Examples of the aryl group represented by $R^4$ in general formula (2) include phenyl group, naphthyl group, azulenyl group, phenantolyl group, fluorenyl group, indenyl group, anthracenyl group, etc. Examples of substituent for the aryl groups include methyl group, ethyl group, 1-propyl group, 2-propyl group, 1-butyl group, 2-butyl group, isobutyl group, tert-butyl group, 1-pentyl group, 2-pentyl group, 3-pentyl group, cyclopentyl group, 1-hexyl group, 2-hexyl group, 3-hexyl group, cyclohexyl group, halogen group (fluorine group, chlorine group, bromine group, iodine group), amino group, dimethylamino group, cyano group, trifluoromethyl group, trimethylsilyl group, hydroxy group, alkoxy group (methoxy group, ethoxy group, propoxy group, phenoxy group, etc.), alkoxymethyl group, nitro group, phenyl group, ester group (methoxycarbonyl group, ethoxycarbonyl group, isopropoxycarbonyl group, tert-butoxycarbonyl group, benzoyloxy group, acetoxy group, etc.), sulfonyl group (methanesulfonyl group, phenylsulfonyl group, p-toluenesulfonyl group, trifluoromethanesulfonyl group, etc.), acyl group (acetyl group, propionyl group, isobutyryl group, isovaleryl group, pivaloyl group, benzoyl group, etc.), amido group (acetoamido group, benzamido group, etc.), carbamoyl group etc. Of these aryl groups, from the viewpoints of easiness in the synthesis of ligand and enantioselectivity of catalytic reaction, phenyl group, naphthyl group, etc. are preferred.

Preferred Examples of substituent for the aryl groups include, in particular, methyl group, ethyl group, 2-propyl group, tert-butyl group, trifluoromethyl group, trimethylsilyl group, methoxy group, ethoxy group, isopropoxy group, phenoxy group, benzyloxy group, nitro group, methoxycarbonyl group, isopropoxycarbonyl group, tert-butoxycarbonyl group, acetoxy group, benzoyloxy group, methanesulfonyl group, phenylsulfonyl group, trifluoromethanesulfonyl group, acetyl group, isobutyryl group, pivaloyl group, or benzoyl group. Of these substituents for the aryl groups, from the viewpoint of enantioselectivity of catalytic reaction, more preferred examples include methyl group, ethyl group, isopropyl group, methoxy group, phenoxy group, etc. One or more these substituents may be present.

Specific examples of aryl groups that may have a substituent include phenyl groups that may have a substituent such as phenyl group, 2'-methylphenyl group, 3'-methylphenyl group, 4'-methylphenyl group, 2'-isopropylphenyl group, 3'-isopropylphenyl group, 4'-isopropylphenyl group, 2'-tert-butylphenyl group, 3'-tert-butylphenyl group, 4'-tert-butylphenyl group, 2'-ethylphenyl group, 3'-ethylphenyl group, 4'-ethylphenyl group, 2',6'-dimethylphenyl group, 2',4'-dimethylphenyl group, 3',5'-dimethylphenyl group, 2',5'-dimethylphenyl group, 2',6'-diethylphenyl group, 2',4'-diethylphenyl group, 3',5'-diethylphenyl group, 2',5'-diethylphenyl group, 2',4',6'-trimethylphenyl group, 2',4',6'-triethylphenyl group, 2',3',4',5',6'-pentamethylphenyl group, 2',3',5',6'-tetramethylphenyl group, 2',6'-diisopropylphenyl group, 3',5'-diisopropylphenyl group, 2',4',6'-triisopropylphenyl group, 3',5'-di-tert-butylphenyl group, 2',3',4',5',6'-pentafluorophenyl group, 2'-chlorophenyl group, 3'-chlorophenyl group, 4'-chlorophenyl group, 2',6'-dichlorophenyl group, 2',4'-dichlorophenyl group, 3',5'-dichlorophenyl group, 2',5'-dichlorophenyl group, 2',4',6'-trichlorophenyl group, 2'-fluorophenyl group, 3'-fluorophenyl group, 4'-fluorophenyl group, 2'-cyanophenyl group, 3'-cyanophenyl group, 4'-cyanophenyl group, 2'-aminophenyl group, 3'-aminophenyl group, 4'-aminophenyl group, 2',6'-diaminophenyl group, 3',5'-diaminophenyl group, 2'-dimethylaminophenyl group, 3'-dimethylaminophenyl group, 4'-dimethylaminophenyl group, 2',6'-dimethylaminophenyl group, 3',5'-dimethylaminoaminophenyl group, 2'-methoxyphenyl group, 3'-methoxyphenyl group, 4'-methoxyphenyl group, 2',6'-dimethoxyphenyl group, 2',4'-dimethoxyphenyl group, 3',5'-dimethoxyphenyl group, 2',5'-dimethoxyphenyl group, 2',4',6'-trimethoxyphenyl group, 2'-trifluoromethyl phenyl group, 3'-trifluoromethyl phenyl group, 4'-trifluoromethyl phenyl group, 2',6'-ditrifluoromethyl phenyl group, 3',5'-ditrifluorophenyl phenyl group, 2'-nitrophenyl group, 3'-nitrophenyl group, 4'-nitrophenyl group, 2',6'-dinitrophenyl group, 2',4'-dinitrophenyl group, 3',5'-dinitrophenyl group, 2',5'-dinitrophenyl group, 2',4',6'-trinitrophenyl group, 2'-phenylphenyl group, 3'-phenylphenyl group, 4'-phenylphenyl group, 2',6'-diphenylphenyl group, 2',4'-diphenylphenyl group, 3',5'-diphenylphenyl group, 2',5'-diphenylphenyl group, 2'-phenoxyphenyl group, 3'-phenoxyphenyl group, 4'-phenoxyphenyl group, 2',6'-diphenoxyphenyl group, 2',4'-diphenoxyphenyl group, 3',5'-diphenoxyphenyl group, 2'-hydroxyphenyl group, 3'-hydroxyphenyl group, 4'-hydroxyphenyl group, 2',6'-dihydroxyphenyl group, 3',5'-dihydroxyphenyl group, 2',4',6'-trihydroxyphenyl group, 4'-trimethylsilylphenyl group, 3',5'-ditrimethylsilyl phenyl group, 2',5'-diphenoxyphenyl group, and naphthyl groups that may have a substituent such as 1-naphthyl group, 2-naphthyl group, etc., and fluorenyl group, indenyl group, anthracenyl group, etc.

Of these groups, 2',6'-dimethylphenyl group, 3',5'-dimethylphenyl group, 2',4',6'-trimethylphenyl group, 2',3',4',5',6'-pentamethylphenyl group, 3',5'-dimethoxyphenyl group, 2'-phenoxyphenyl group, 1-naphthyl group, etc. are preferred.

Examples of phenyl groups having a substituent include, preferably, phenyl groups having a substituent at the ortho- or meta-position. Specific examples include 2'-methylphenyl group, 3'-methylphenyl group, 2',3'-dimethylphenyl group, 2',5'-dimethylphenyl group, 2',6'-dimethylphenyl group, 3',5'-dimethylphenyl group, 2'-ethylphenyl group, 3'-ethylphenyl group, 2',3'-diethylphenyl group, 2',5'-diethylphenyl group, 2',6'-diethylphenyl group, 3',5'-diethylphenyl group, 2'-isopropylphenyl group, 3'-isopropylphenyl group, 2',3'-diisopropylphenyl group, 2',5'-diisopropylphenyl group, 2',6'-diisopropylphenyl group, 3',5'-diisopropylphenyl group, 2'-tert-butylphenyl group, 3'-tert-butylphenyl group, 2',3'-di-tert-butylphenyl group, 2',5'-di-tert-butylphenyl group, 2',6'-di-tert-butylphenyl group, 3',5'-di-tert-butylphenyl group, 2'-methoxyphenyl group, 3'-methoxyphenyl group, 2',3'-dimethoxyphenyl group, 2',5'-dimethoxyphenyl group, 2',6'-dimethoxyphenyl group, 3',5'-dimethoxyphenyl group, 2'-ethoxyphenyl group, 3'-ethoxyphenyl group, 2',3'-diethoxyphenyl group, 2',5'-diethoxyphenyl group, 2',6'-diethoxyphenyl group, 3',5'-diethoxyphenyl group, 2'-isopropoxyphenyl group, 3'-isopropoxyphenyl group, 2',3'-diisopropoxyphenyl group, 2',5'-diisopropoxyphenyl group, 2',6'-diisopropoxyphenyl group, 3',5'-diisopropoxyphenyl group, 2'-tert-butoxyphenyl group, 3'-tert-butoxyphenyl group, 2',3'-di-tert-butoxyphenyl group, 2',5'-di-tert-butoxyphenyl group, 2',6'-di-tert-butoxyphenyl group, 3',5'-di-tert-butoxyphenyl group, 2'-phenoxyphenyl group, 3'-phenoxyphenyl group, 2',3'-diphenoxyphenyl group, 2',5'-diphenoxyphenyl group, 2',6'-diphenoxyphenyl group, 3',5'-diphenoxyphenyl group, 2'-benzyloxyphenyl group, 3'-benzyloxyphenyl group, 2',3'-dibenzyloxyphenyl group, 2',5'-dibenzyloxyphenyl group, 2',6'-dibenzyloxyphenyl group, 3',5'-dibenzyloxyphenyl group, 2'-phenylphenyl group, 3'-phenylphenyl group, 2',3'-diphenylphenyl group, 2',5'-diphenylphenyl group, 2',6'-diphenylphenyl group, 3',5'-diphenylphenyl group, 2'-nitrophenyl group, 3'-nitrophenyl group, 2',3'-dinitrophenyl group, 2',5'-dinitrophenyl group, 2',6'-dinitrophenyl group, 3',5'-dinitrophenyl group, 2'-trifluoromethyl phenyl group, 3'-trifluoromethyl phenyl group, 2',3'-bis(trifluoromethyl)phenyl group, 2',5'-bis(trifluoromethyl)phenyl group, 2',6'-bis(trifluoromethyl)phenyl group, 3',5'-bis(trifluoromethyl)phenyl group, 2'-chlorophenyl group, 3'-chlorophenyl group, 2',3'-dichlorophenyl group, 2',5'-dichlorophenyl group, 2',6'-dichlorophenyl group, 3',5'-dichlorophenyl group, 2'-fluorophenyl group, 3'-fluorophenyl group, 2',3'-difluorophenyl group, 2',5'-difluorophenyl group, 2',6'-difluorophenyl group, 3',5'-difluorophenyl group, 2'-methoxycarbonylphenyl group, 3'-methoxycarbonylphenyl group, 2',3'-dimethoxycarbonylphenyl group, 2',5'-dimethoxycarbonylphenyl group, 2',6'-dimethoxycarbonylphenyl group, 3',5'-dimethoxycarbonylphenyl group, 2'-ethoxycarbonylphenyl group, 3'-ethoxycarbonylphenyl group, 2',3'-diethoxycarbonylphenyl group, 2',5'-diethoxycarbonylphenyl group, 2',6'-diethoxycarbonylphenyl group, 3',5'-diethoxycarbonylphenyl group, 2'-tert-butoxycarbonylphenyl group, 3'-tert-butoxycarbonylphenyl group, 2',3'-di-tert-butoxycarbonylphenyl group, 2',5'-di-tert-butoxycarbonylphenyl group, 2',6'-di-tert-butoxycarbonylphenyl group, 3',5'-di-tert-butoxycarbonylphenyl group, 2'-trimethylsilyl phenyl group, 3'-trimethylsilyl phenyl group, 2',3'-bis(trimethylsilyl)phenyl group, 2',5'-bis(trimethylsilyl)phenyl group, 2',6'-bis(trimethylsilyl)phenyl group, 3',5'-bis(trimethylsilyl)phenyl group, 2'-methanesulfonylphenyl group, 3'-methanesulfonylphenyl group, 2',3'-dimethanesulfonylphenyl group, 2',5'-dimethanesulfonylphenyl group, 2',6'-dimethanesulfonylphenyl group, 3',5'-dimethanesulfonylphenyl group, 2'-trifluoromethanesulfonylphenyl group, 3'-trifluoromethanesulfonylphenyl group, 2',3'-ditrifluoromethanesulfonylphenyl group, 2',5'-ditrifluoromethanesulfonylphenyl group, 2',6'-ditrifluoromethanesulfonylphenyl group, 3',5'-ditrifluoromethanesulfonylphenyl group, 2'-dimethylaminophenyl group, 3'-dimethylaminophenyl group, 2',3'-bis(dimethylamino)phenyl group, 2',5'-bis(dimethylamino)phenyl group, 2',6'-bis(dimethylamino)phenyl group, 3',5'-bis(dimethylamino)phenyl group, 2'-acetylphenyl group, 3'-acetylphenyl group, 2',3'-diacetylphenyl group, 2',5'-diacetylphenyl group, 2',6'-diacetylphenyl group, 3',5'-diacetylphenyl group, etc. Most preferable examples include 2',6'-di-substituted phenyl groups and 3',5'-di-substituted phenyl groups.

Of these, preferable examples include 2',6'-dimethylphenyl group, 3',5'-dimethylphenyl group, 2',4',6'-trimethylphenyl group, 2',3',4',5',6'-pentamethylphenyl group, 3',5'-dimethoxyphenyl group, 2'-phenoxyphenyl group, 1-naphtyl group, etc.

Specific examples of the heterocyclic group represented by $R^4$ in general formula (2) include heterocyclic groups such as tienyl group, pyridyl group, furanyl group, tetrahydrofuranyl group, pyrrole group, picolyl group, etc. Of these, examples of preferable heterocyclic group include tienyl group, pyridyl group, etc.

Examples of substituent for the above heterocyclic groups include the above-described substituents for the aryl groups.

Particularly preferable examples of the group represented by $R^4$ in general formula (2) include, from the viewpoint of enentioselectivity in asymmetric reduction or asymmetric hydrogenation, tert-butyl group, 3-pentyl group, 4-heptyl group, cyclopentyl group, cyclohexyl group, cycloheptyl group, 2'-nitrophenyl group, 2',6'-dimethylphenyl group, 3',5'-dimethylphenyl group, 3',5'-dimethoxyphenyl group, 2',4',6'-trimethylphenyl group, 2',3',4',5',6'-pentamethylphenyl group, 2'-phenoxyphenyl group, 1-naphtyl group, etc.

Specific examples of Ar in general formulae (1) and (3) include cyclopentadienyl groups that may have a substituent such as cyclopentadienyl group, methylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, 1,2,3,4,5-pentamethylcyclopentadienyl group, tetraphenylcyclopentadienyl group, pentaphenylcyclopentadienyl group, menthyl tetraphenylcyclopentadienyl group, neomenthyl tetraphenylcyclopentadienyl group, menthylcyclopentadienyl group, neomenthylcyclopentadienyl group, indenyl group, 1-methylindenyl group, 2-methylindenyl group, dimethylindenyl group, 2-methyl-4-phenylindenyl group, 2-methyl-4,5-benzoindenyl group, tetrahydroindenyl group, menthyltetrahydroindenyl group, neomenthyltetrahydroindenyl group, fluorenyl group, etc., or benzenes that may have a substituent such as benzene, toluene, o-xylene, m-xylene, p-xylene, o-cymene, m-cymene, p-cymene, 1-methyl-2-ethylbenzene, 1-methyl-3-ethylbenzene, 1-methyl-4-ethylbenzene, 1-methyl-2-n-propylbenzene, 1-methyl-3-n-propylbenzene, 1-methyl-4-n-propylbenzene, 1-methyl-2-n-butylbenzene, 1-methyl-3-n-butylbenzene, 1-methyl-4-n-butylbenzene, 1-methyl-2-iso-butylbenzene, 1-methyl-3-iso-butylbenzene, 1-methyl-4-iso-butylbenzene, 1-methyl-2-tert-butylbenzene, 1-methyl-3-tert-butylbenzene, 1-methyl-4-tert-butylbenzene, 1-methyl-2-n-pentylbenzene, 1-methyl-3-n-pentylbenzene, 1-methyl-4-n-pentylbenzene, 1-methyl-2-iso-pentylbenzene, 1-methyl-3-iso-pentylbenzene, 1-methyl-4-iso-pentylbenzene, 1-methyl-2-cyclopentylbenzene, 1-methyl-3-cyclopentylbenzene, 1-methyl-4-cyclopentylbenzene, 1-methyl-2-n-hexylbenzene, 1-methyl-3-n-hexylbenzene, 1-methyl-4-n-hexylbenzene, 1-methyl-2-cyclohexylbenzene, 1-methyl-3-cyclohexylbenzene, 1-methyl-4-cyclohexylbenzene, 1,2,3-trimethylbenzene, 1,2,4-trimethylbenzene, 1,3,5-trimethylbenzene, 1,2,4,5-tetramethylbenzene, 1,2,3,4-tetramethylbenzene, pentamethylbenzene, hexamethylbenzene, phenylbenzene, chlorobenzene, trifluorobenzene, etc.

From the viewpoint of easiness in the synthesis of complex, preferable examples of the above Ar include p-cymene, 1,3,5-trimethylbenzene, 1,2,3,4,5-pentamethylcyclopentadienyl group, etc.

X in general formulae (1) and (3) is a hydride group or an anionic group; an anionic group herein means a group bound to a metal atom M, which easily detaches from the metal atom M to generate a cationic catalytic molecule. Examples of the anionic group include halogen atoms. Specific examples of X include hydride group, cross-linked oxo group, fluorine group, chlorine group, bromine group, iodine group, tetrafluoroborate group, tetrahydroborate group, tetrakis[3',5'-bis(trifluoromethyl)phenyl]borate group, acetoxy group, benzoyloxy group, (2',6'-dihydroxybenzoyl)oxy group, (2',5'-dihydroxybenzoyl)oxy group, (3'-aminobenzoyl)oxy group, (2',6'-dimethoxybenzoyl)oxy group, (2',4',6'-triisopropylbenzoyl)oxy group, 1-naphthalenecarboxylic acid group, 2-naphthalenecarboxylic acid group, trifluoroacetoxy group, trifluoromethanesulfonimido group, nitromethyl group, nitroethyl group, sulfonate group (methanesulfonate group, ethanesulfonate group, n-propanesulfonate group, iso-propanesulfonate group, n-butanesulfonate group, fluoromethanesulfonate group, difluoromethanesulfonate group, trifluoromethanesulfonate group, pentafluoroethanesulfonate group, etc), hydroxyl group, etc. Of these, trifluoromethanesulfonate group, hydride group, fluorine group, chlorine group, bromine group or iodine group are particularly preferred.

M in general formulae (1) and (3) is either ruthenium, iridium or rhodium, and preferably ruthenium or iridium.

The compound of general formula (1) may possibly be isolated in a state wherein a solvent molecule or water molecule expressed by L used in its synthesis is weakly bound or coordinated in some cases; even if a solvent molecule or water molecule is bound or coordinated, its catalytic performance is not affected and the compound can be used similar to complexes having a structure wherein solvent molecules or water molecules are not bound or coordinated. The solvent bound or coordinated to the compound of general formula (1) is not particularly limited, and examples include tetrahydrofuran, diethyl ether, diisopropyl ether, tert-butyl methyl ether, dimethylformamido, chloroform, dichloroethane, methanol, ethanol, 2-propanol, etc.

* in general formula (1) represents asymmetric carbon; since a diamine ligand has two asymmetric carbons, there are four kinds of combination: (S,S), (R,R), (S,R), and (R,S) forms. Preferable forms include (S,S) and (R,R) forms.

Representative examples of the compound of general formula (1) are shown below, but said compound is not limited thereto.

[Chem. 6]

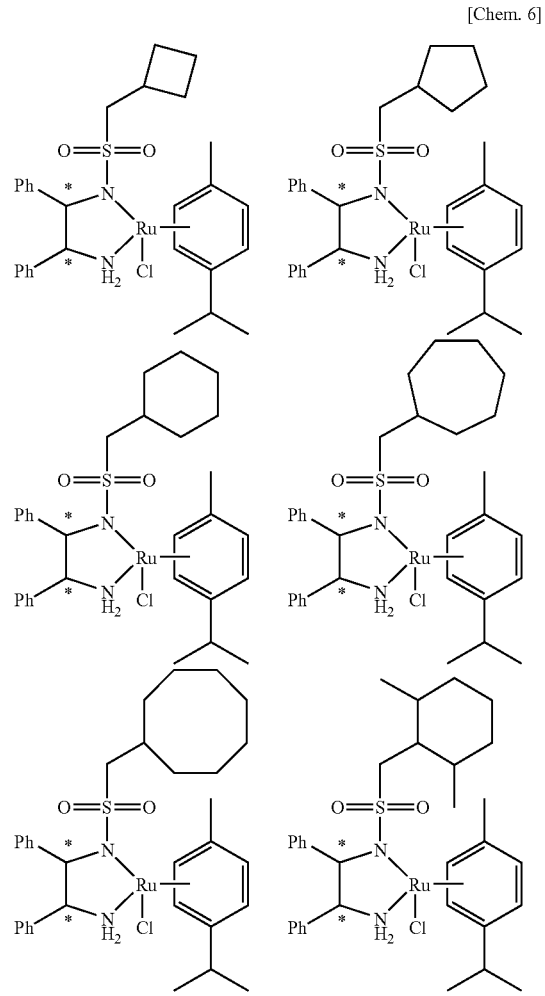

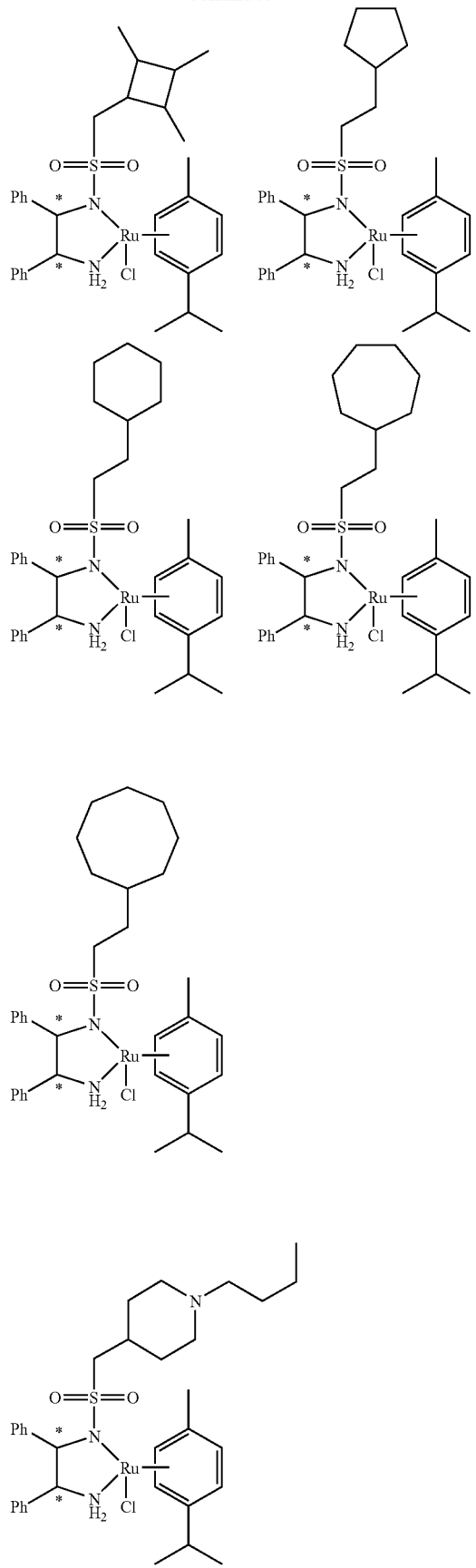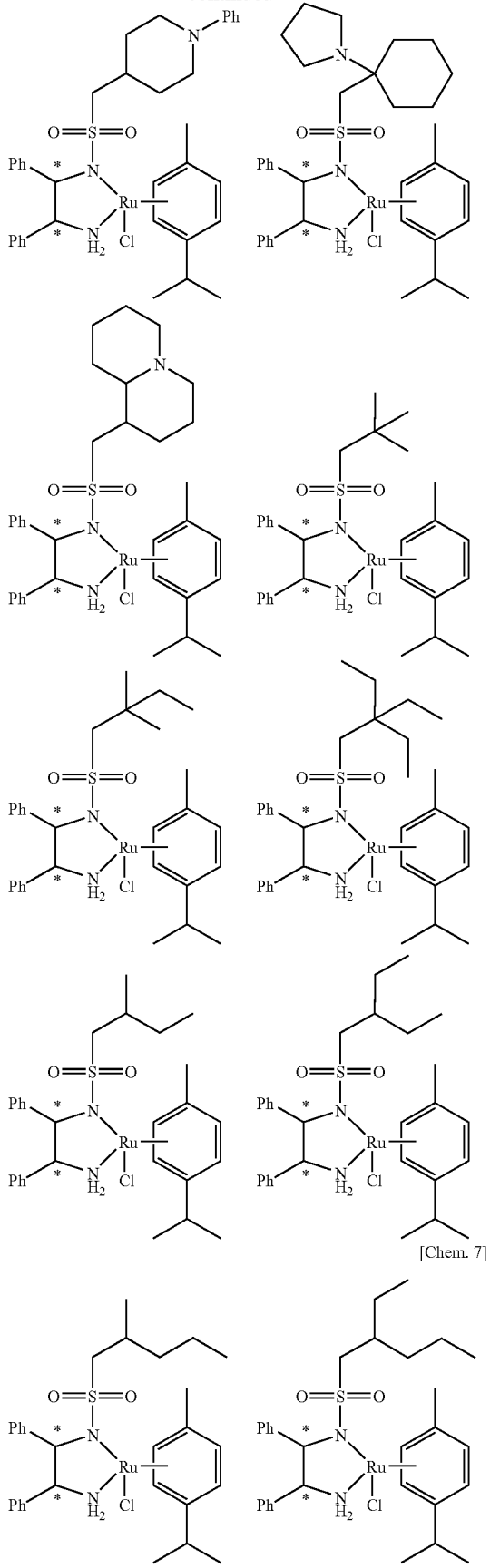
[Chem. 7]

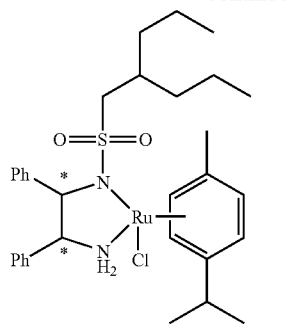
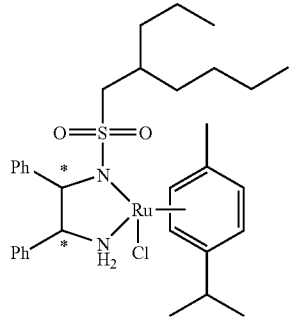
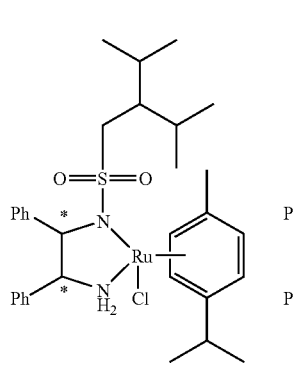
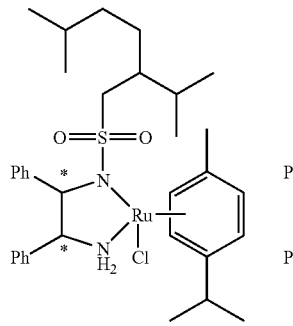
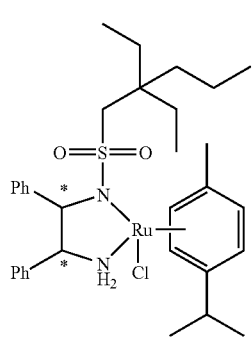
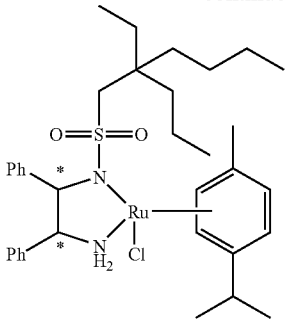
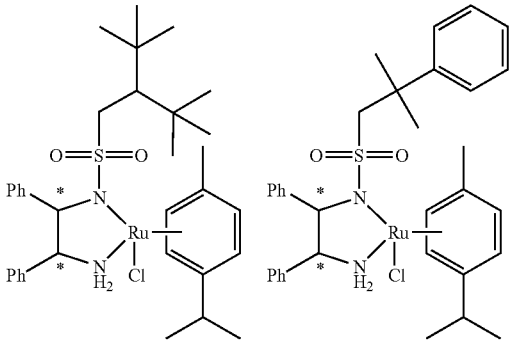
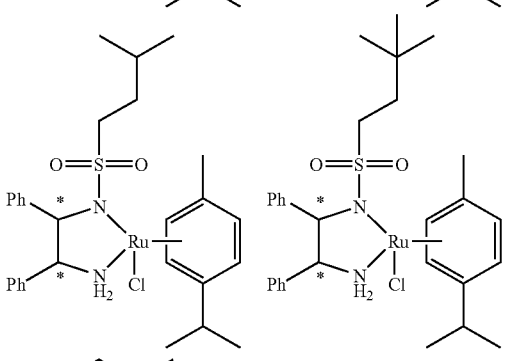
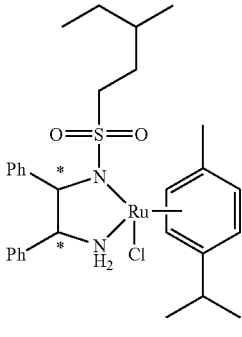
[Chem. 8]
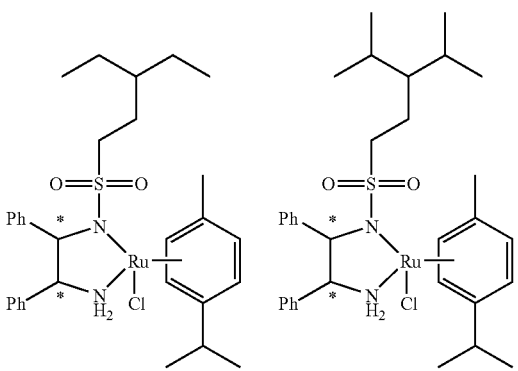

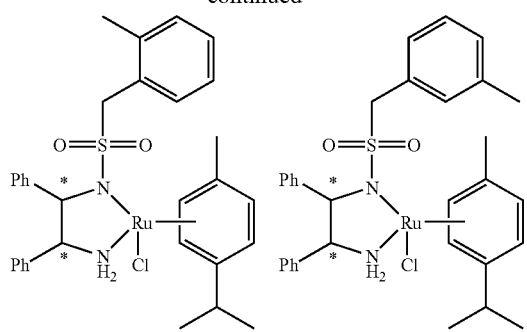
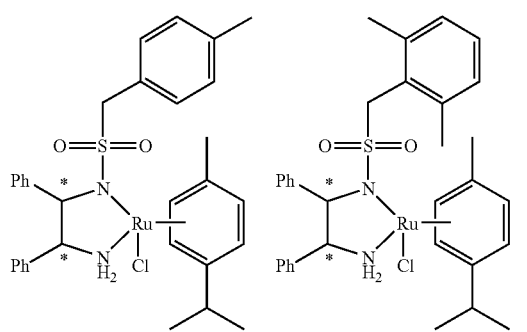
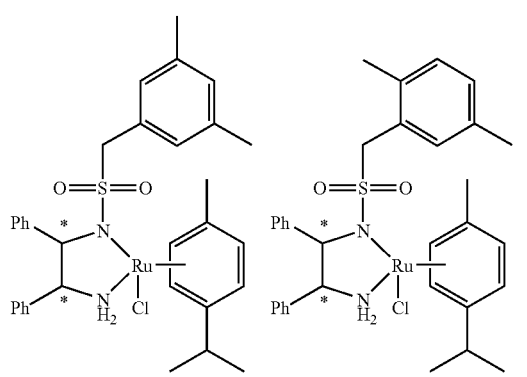
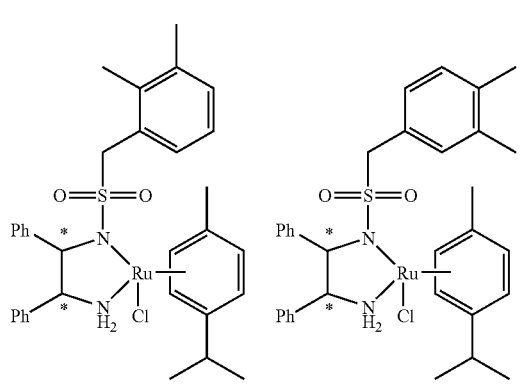
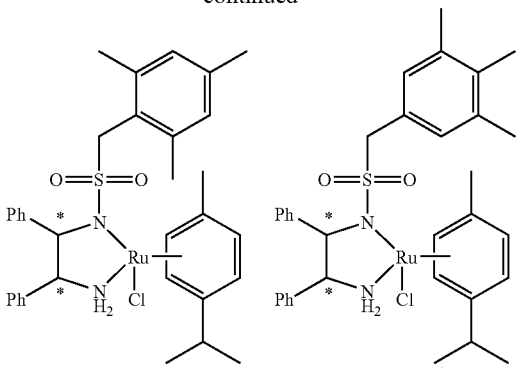
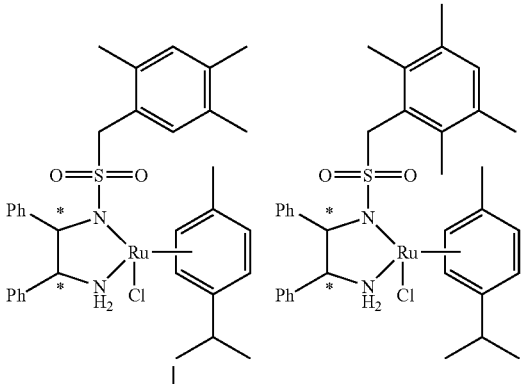
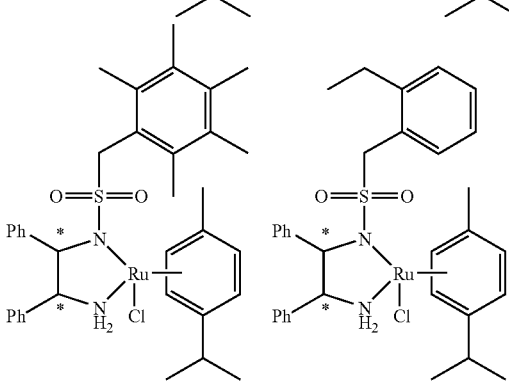
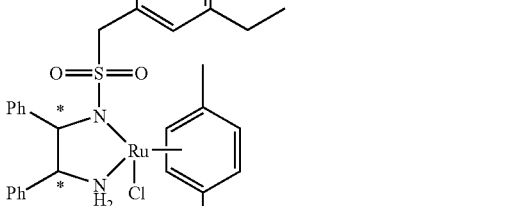
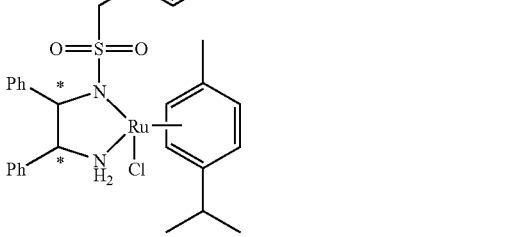

-continued
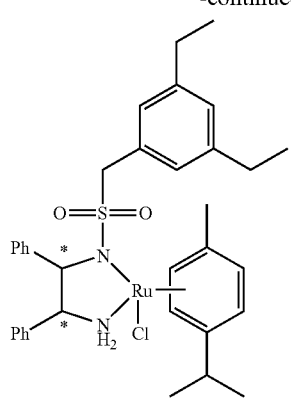
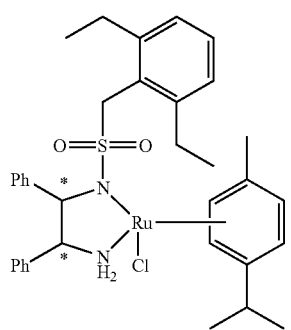
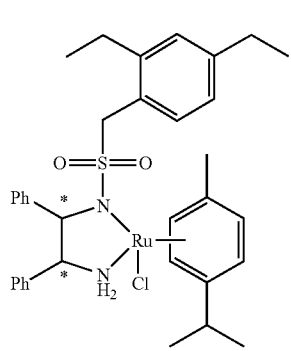
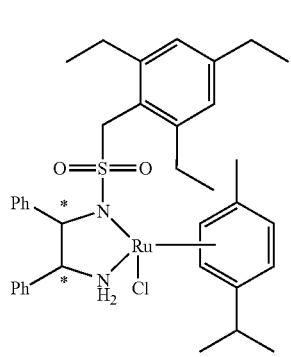
-continued
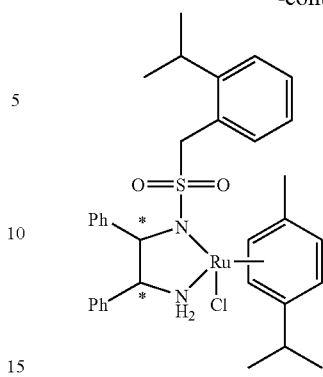
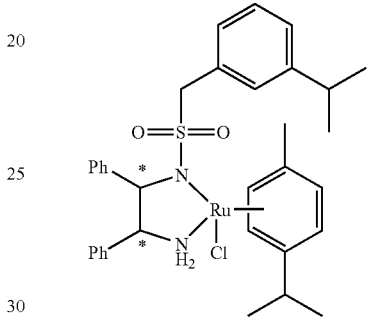
[Chem. 9]
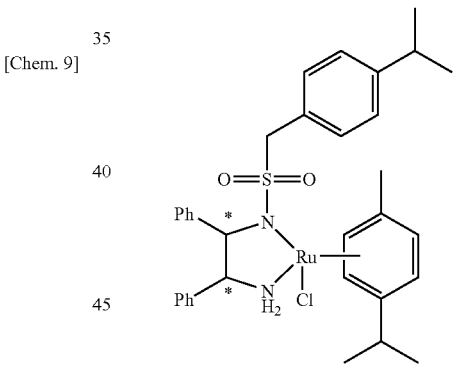
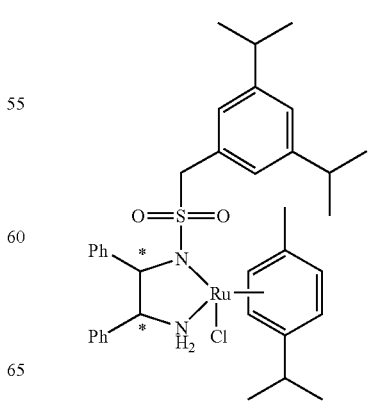

-continued
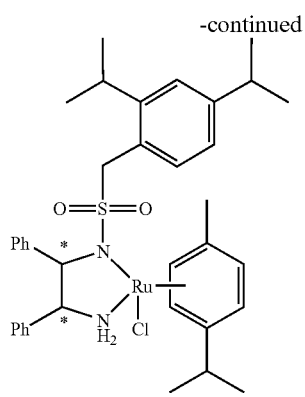
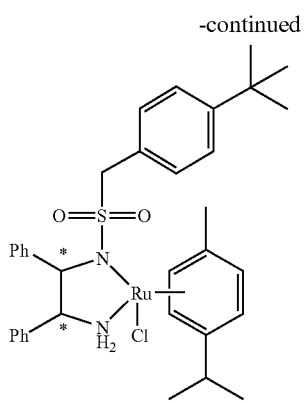
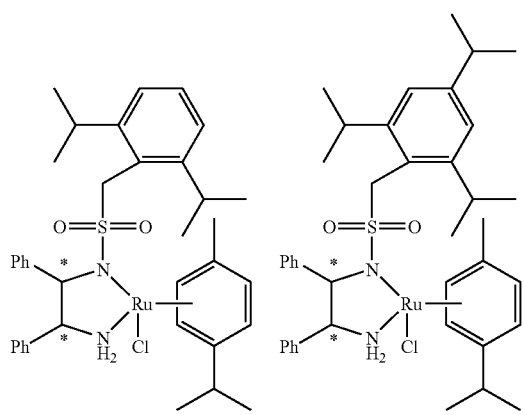
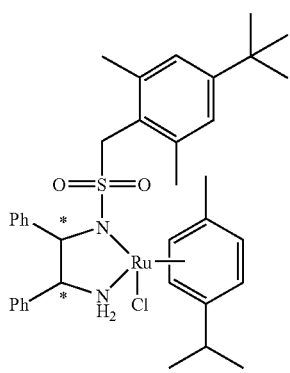
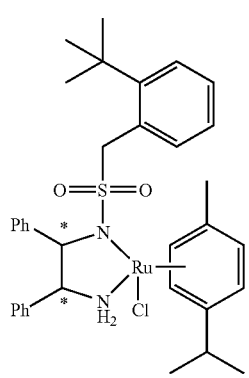
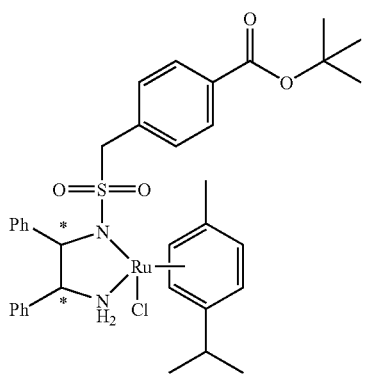
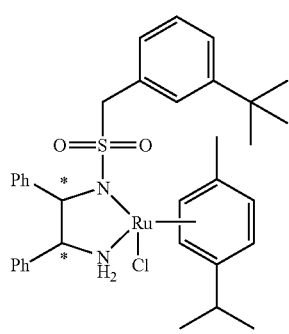
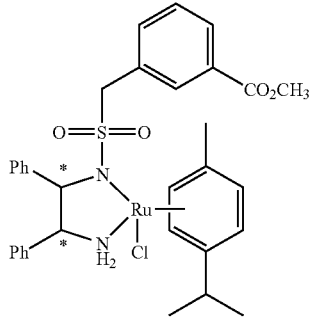

[Chem. 10]
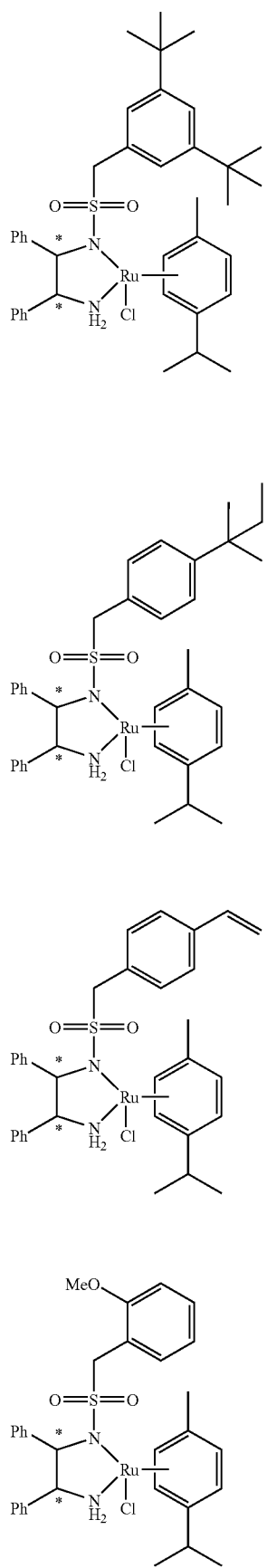
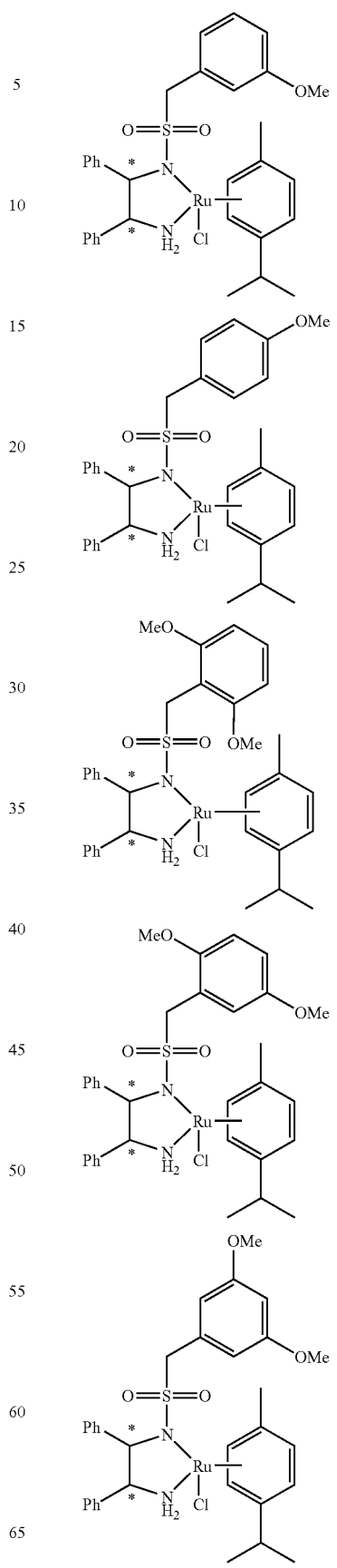

27
-continued
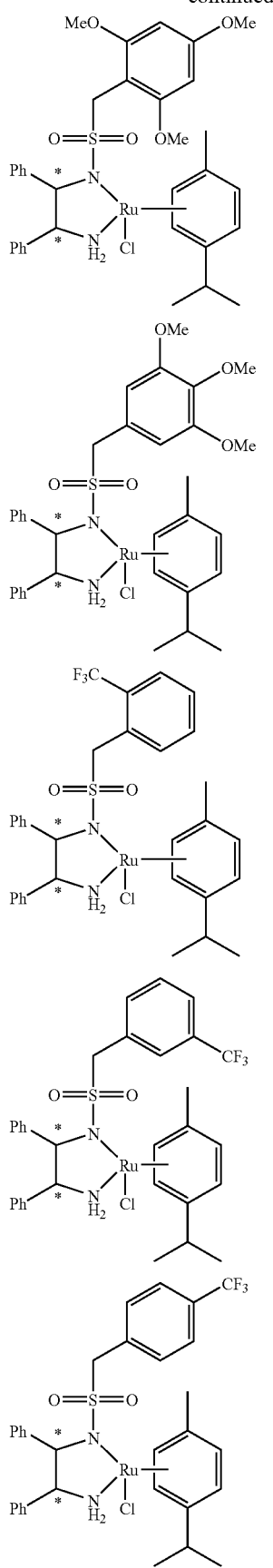
28
-continued
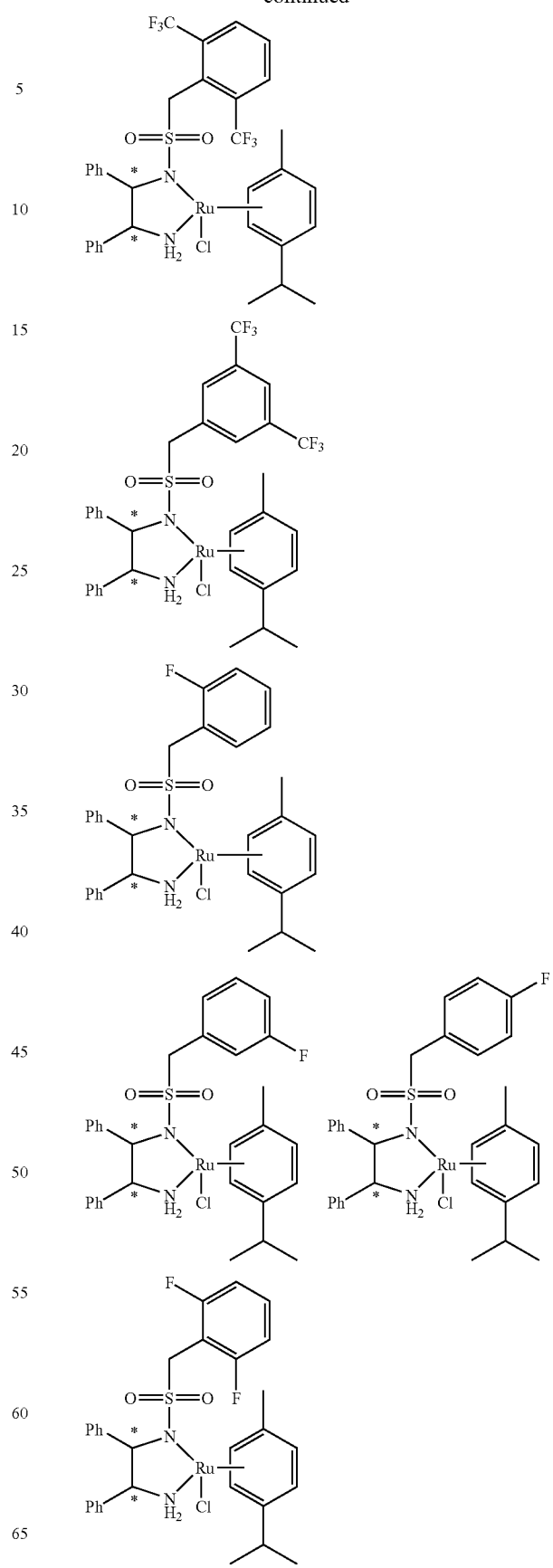

-continued

31
-continued
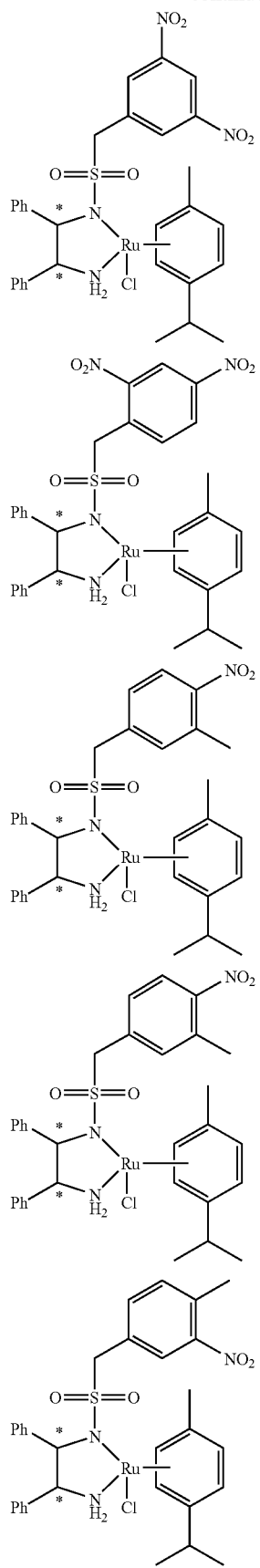
32
-continued
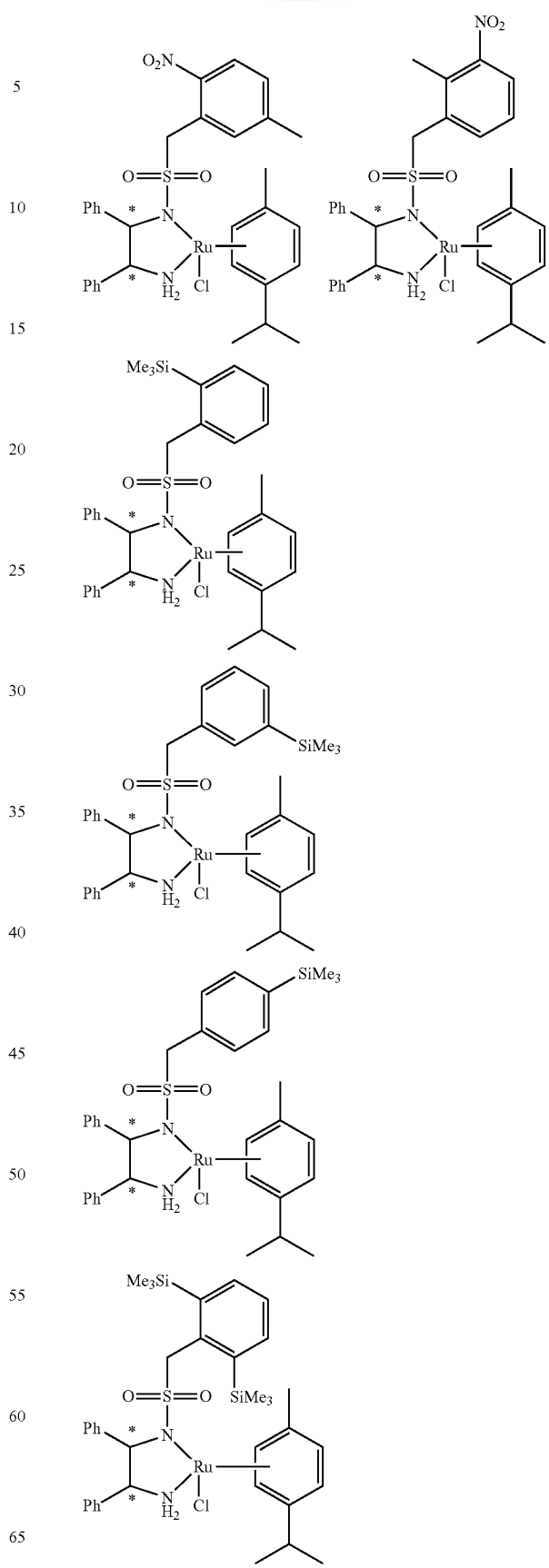

-continued
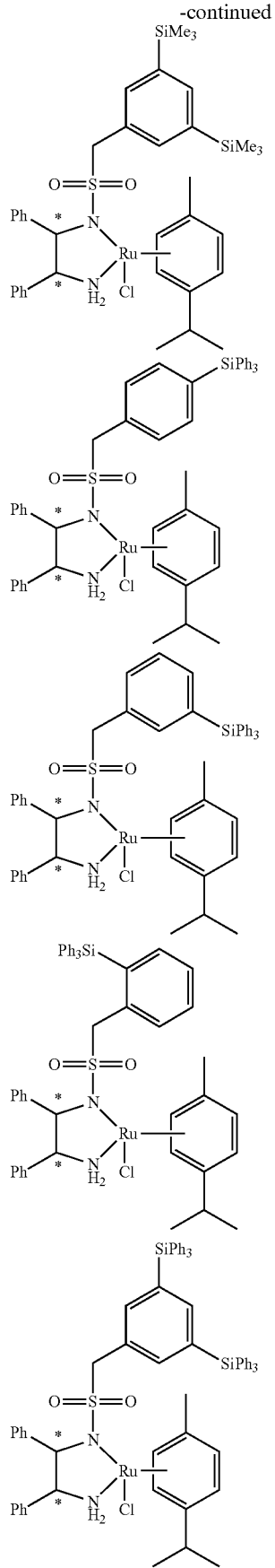
-continued
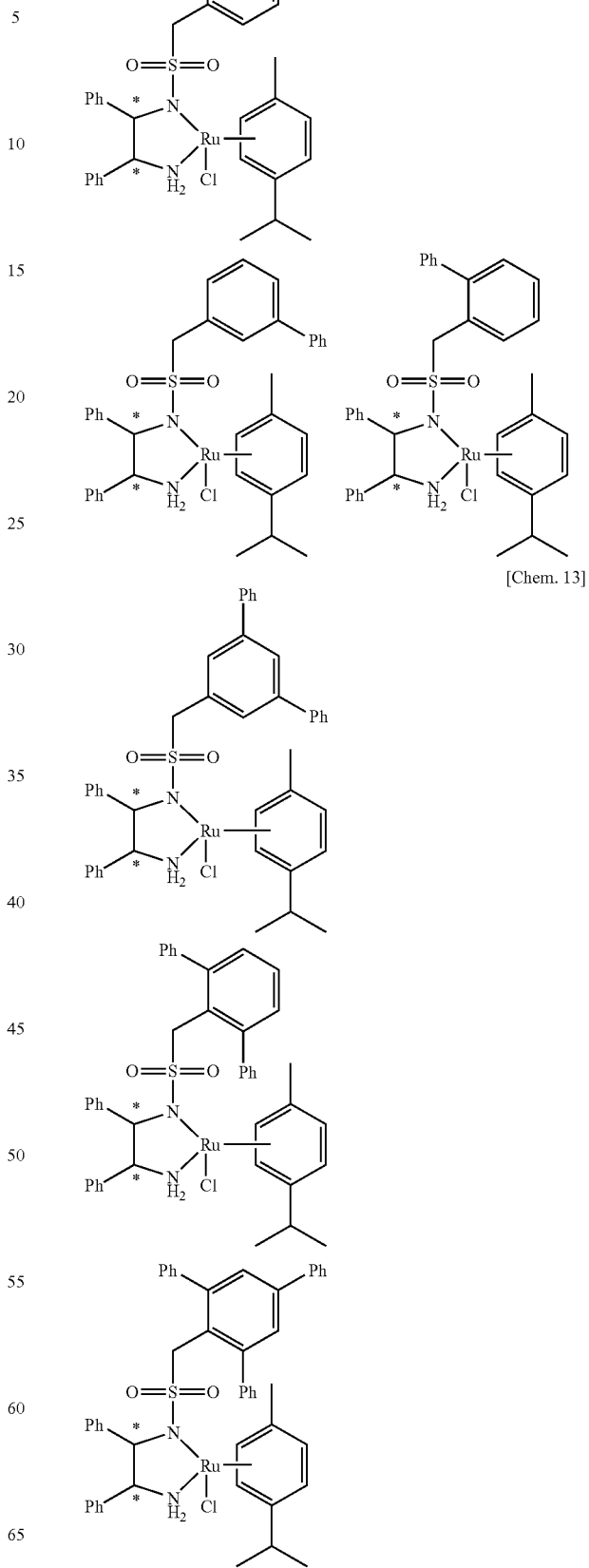
[Chem. 13]

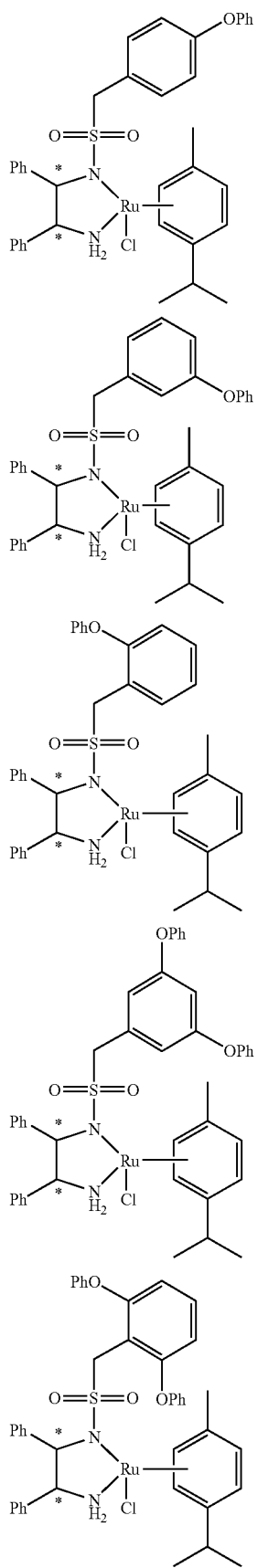
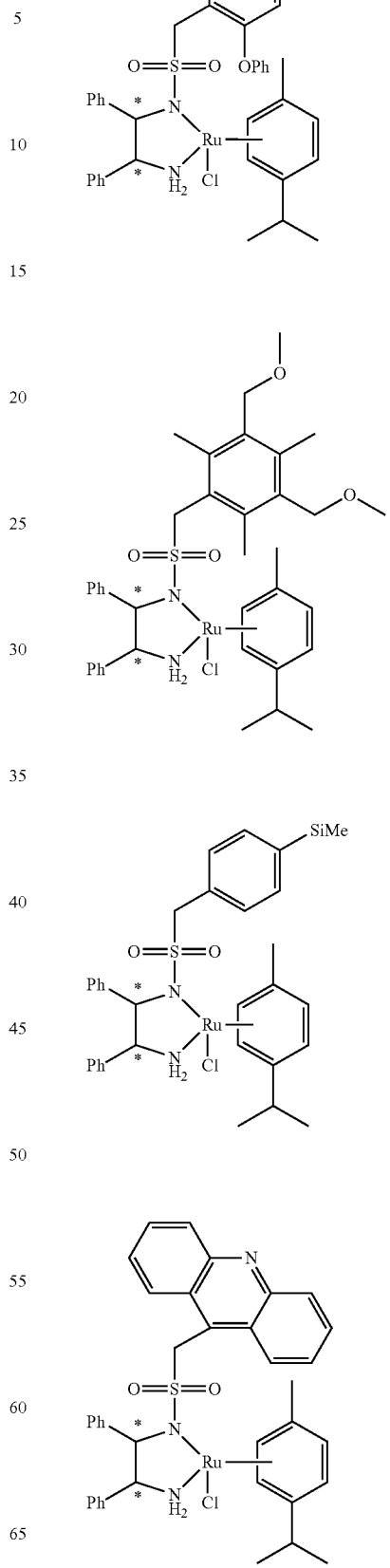

37
-continued
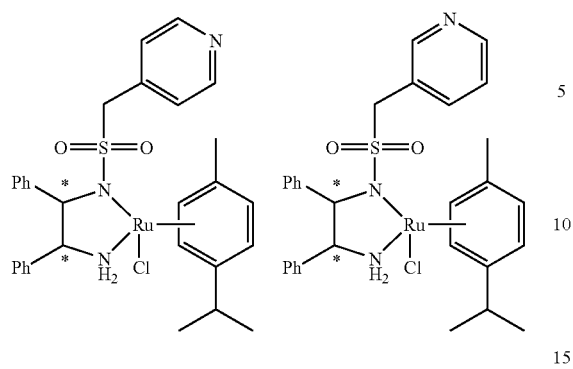
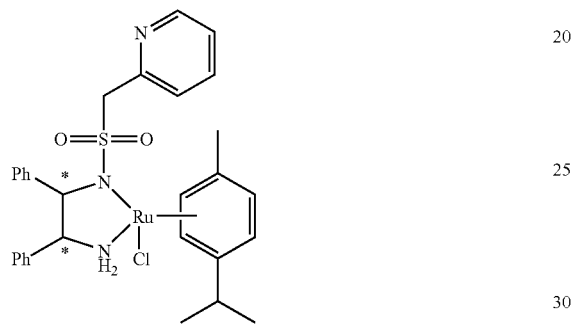
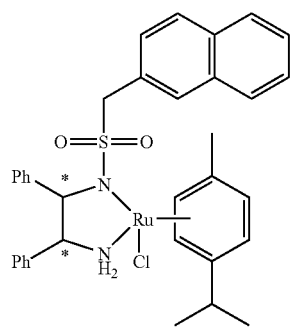
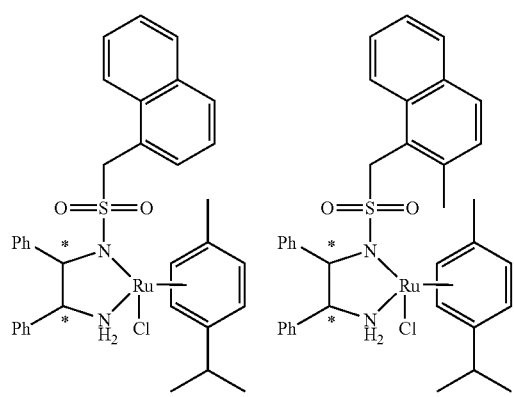
38
-continued
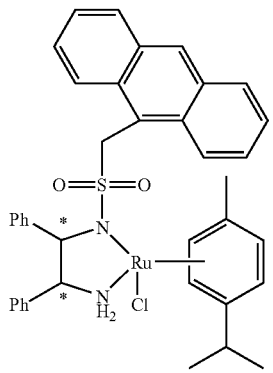
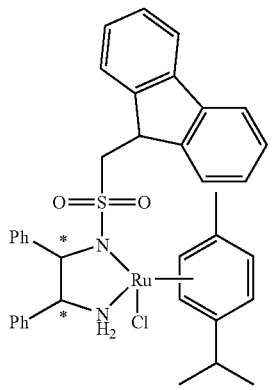
[Chem. 14]
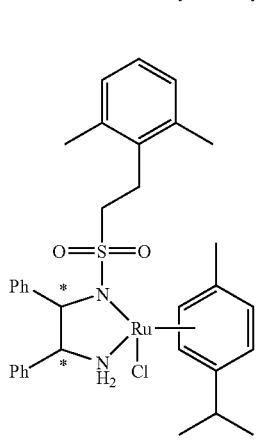
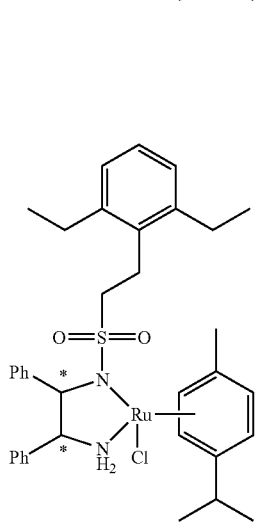

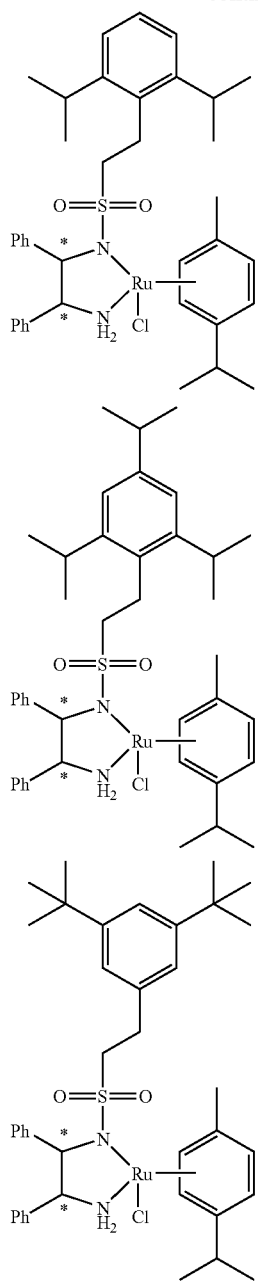
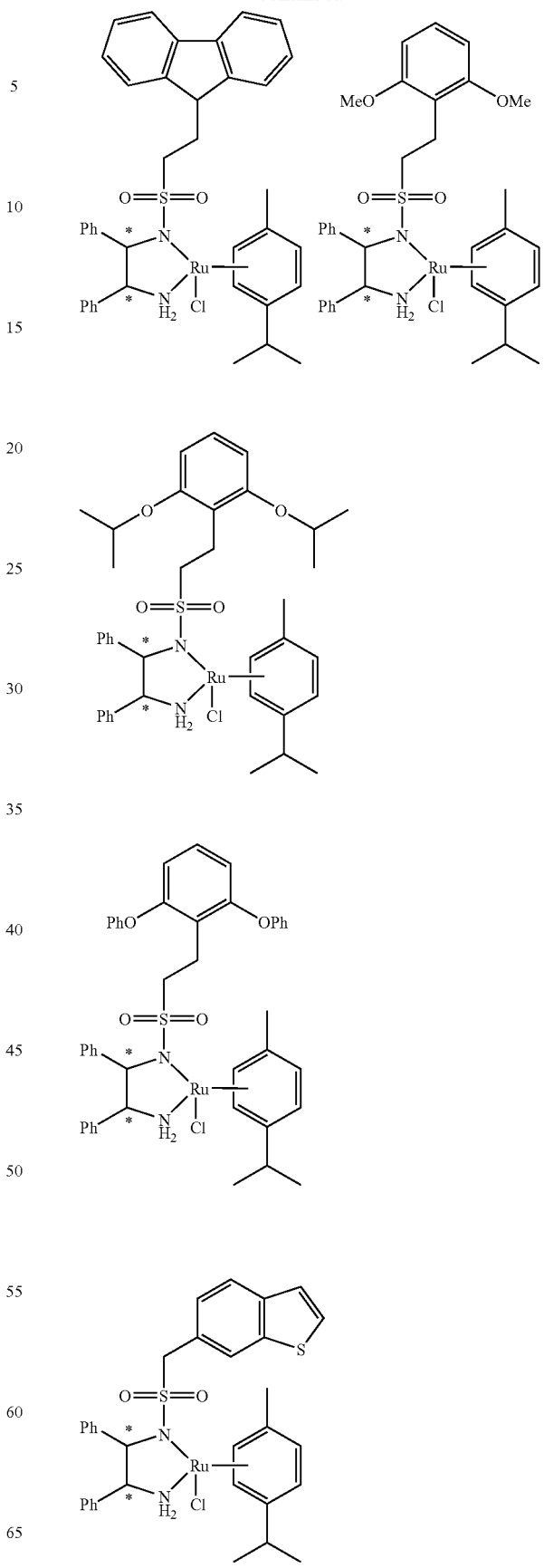

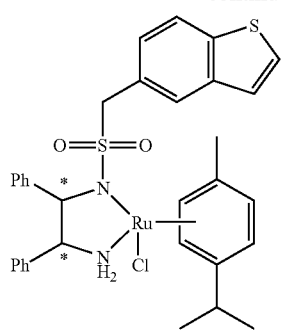
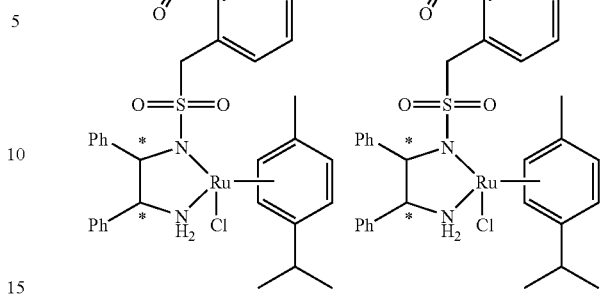
[Chem. 15]
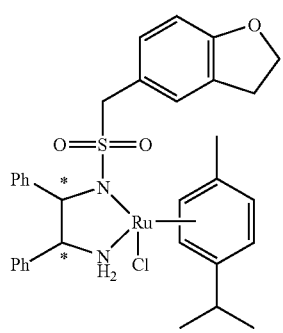
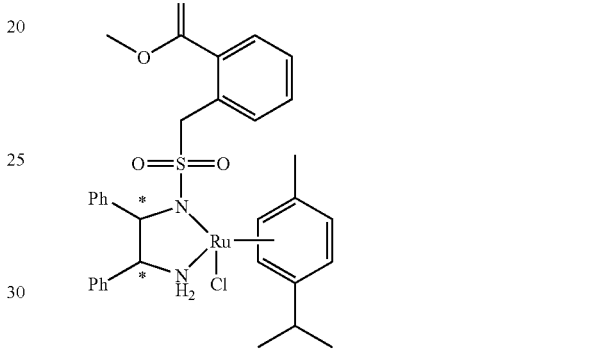
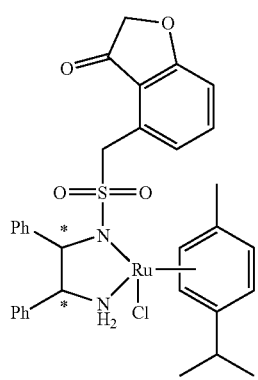
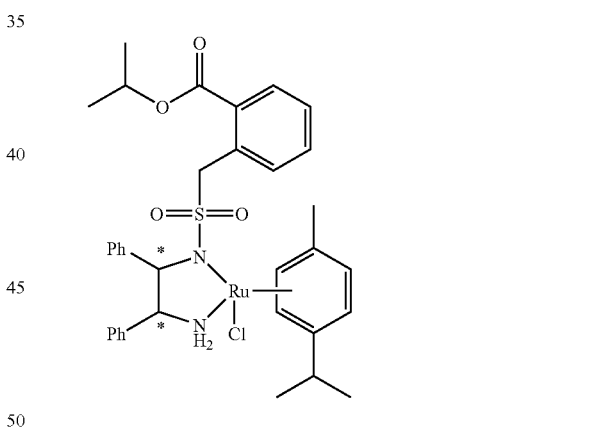
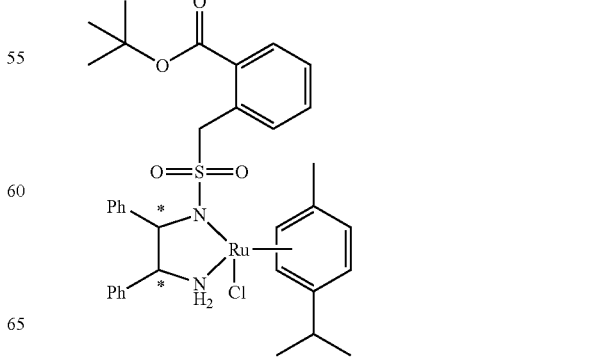

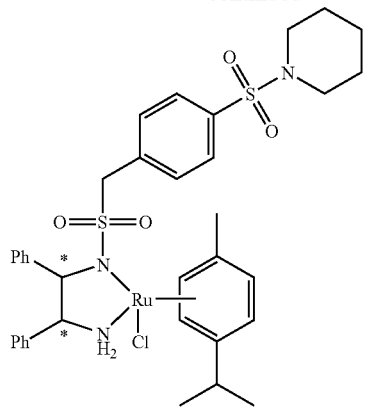
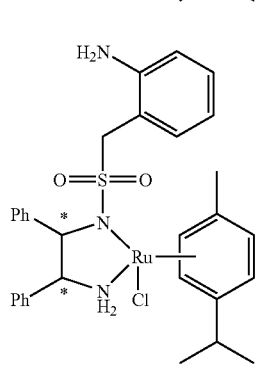
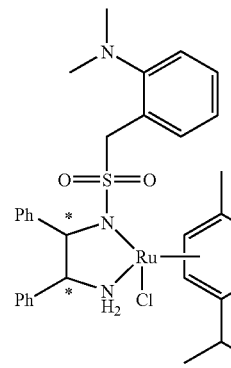
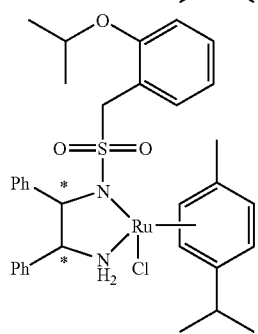
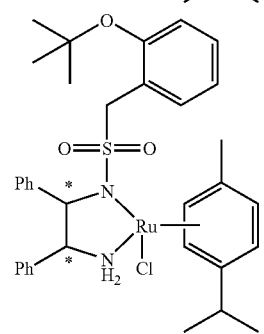
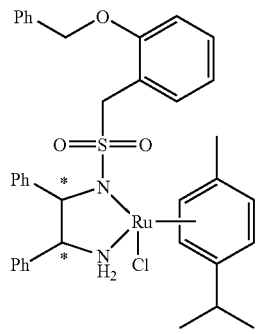
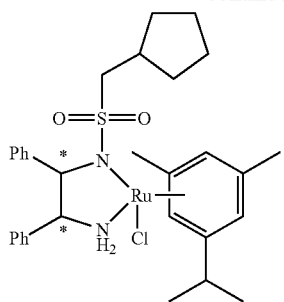
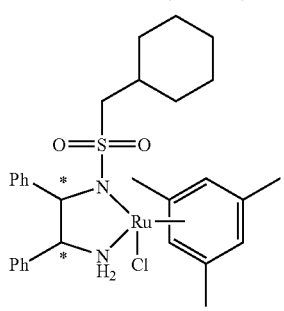
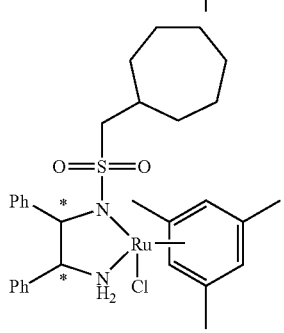
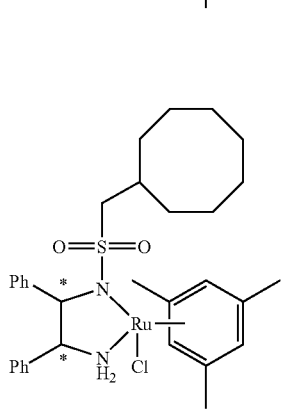
[Chem. 16]
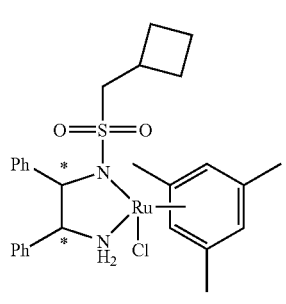
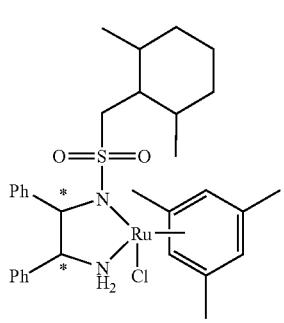

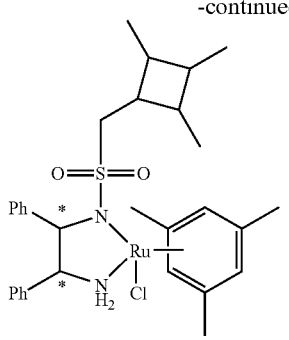
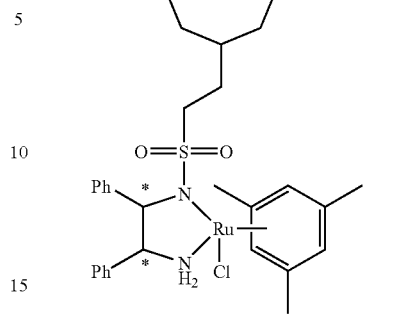
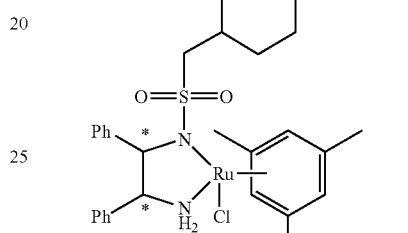
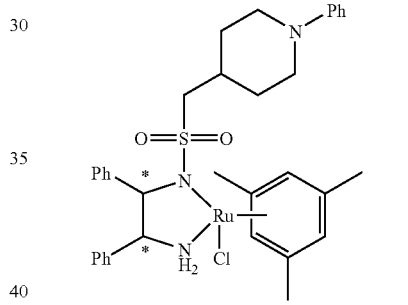
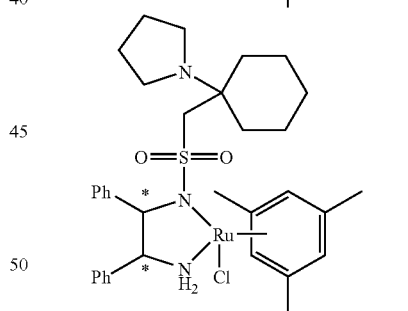
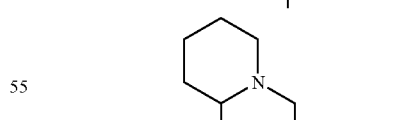
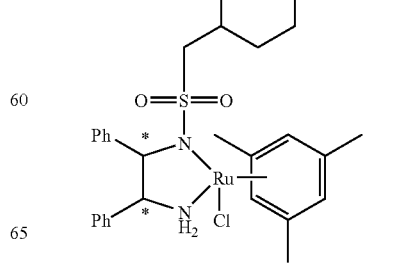

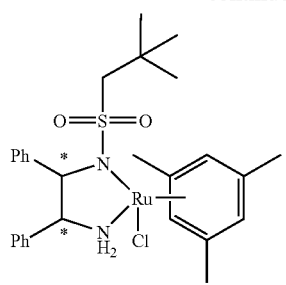
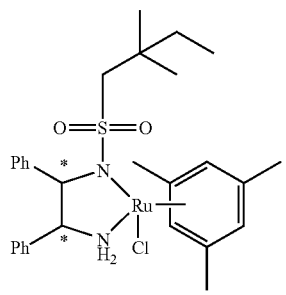
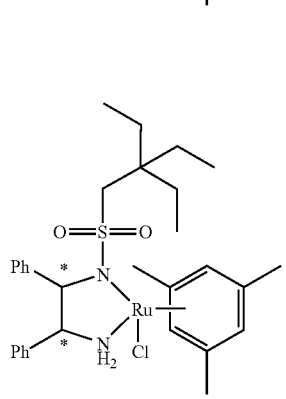
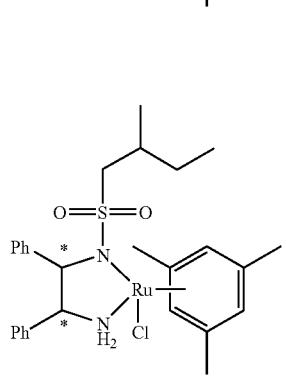
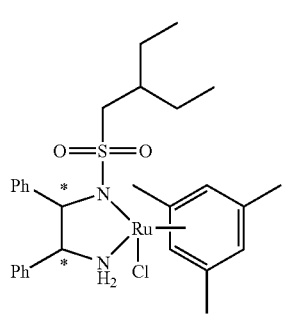
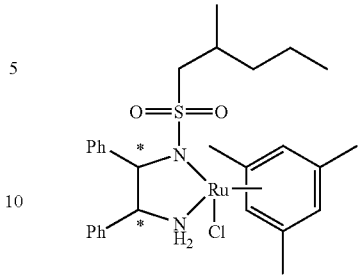
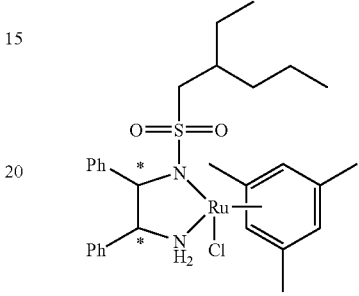
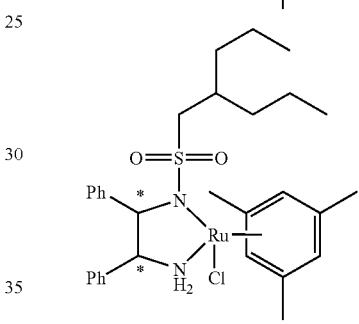
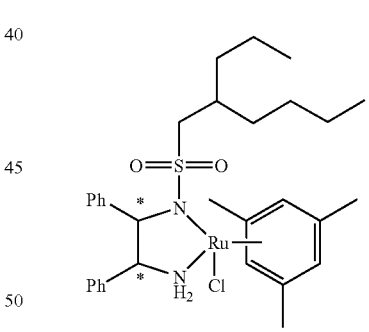
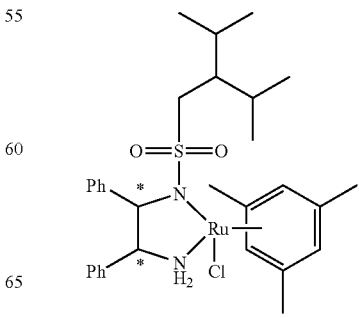
[Chem. 17]

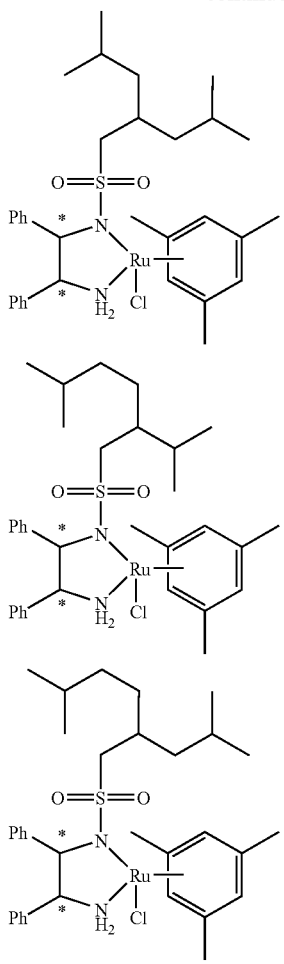
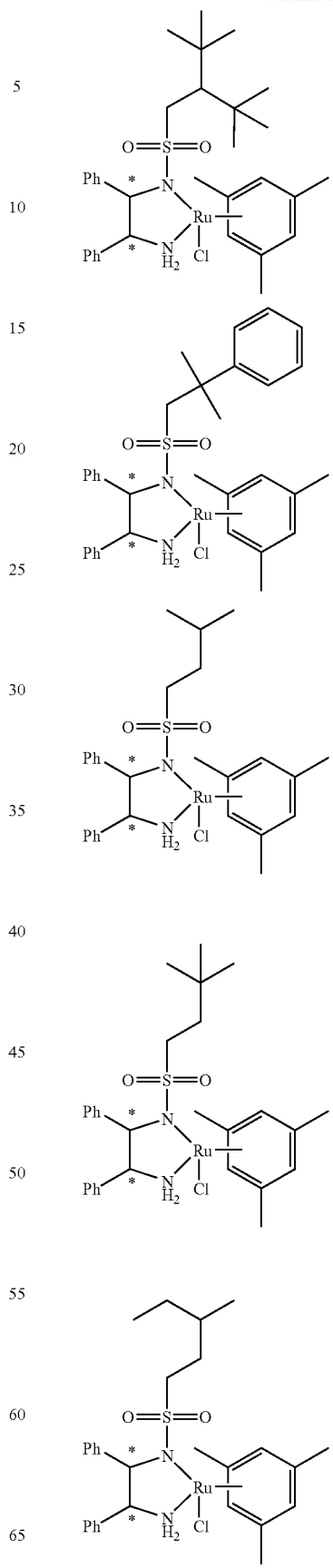

51
-continued
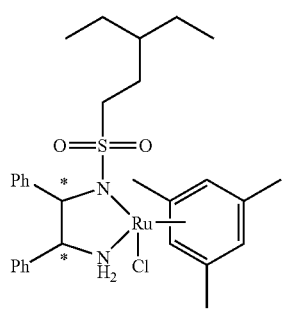
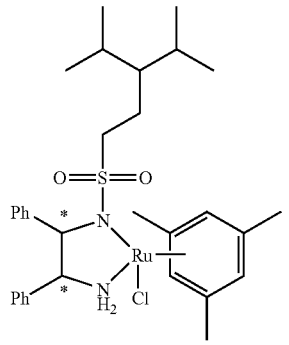
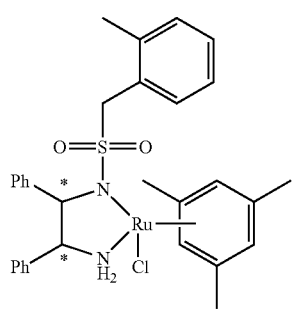
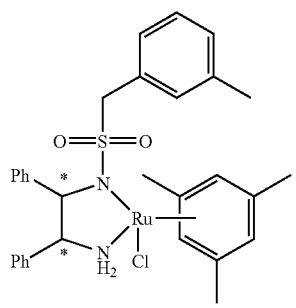
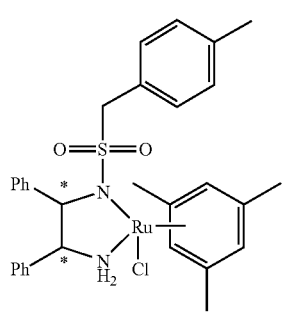
52
-continued
[Chem. 18]
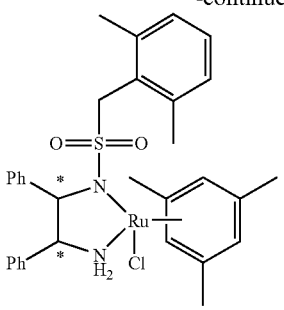
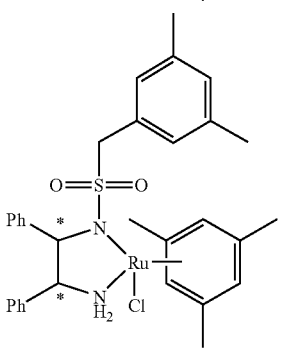
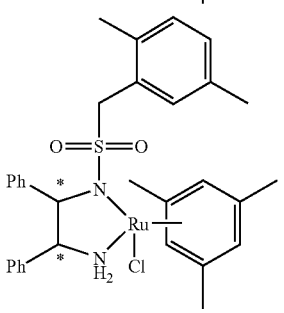
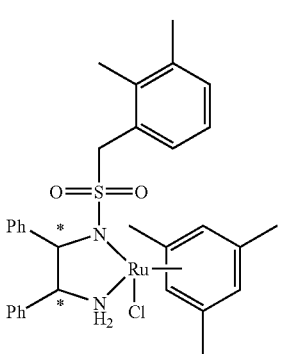
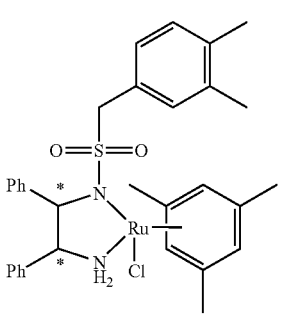

-continued
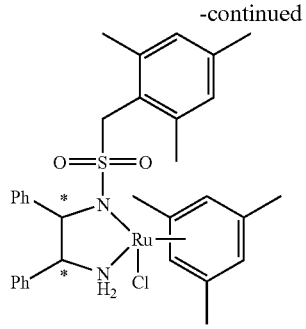
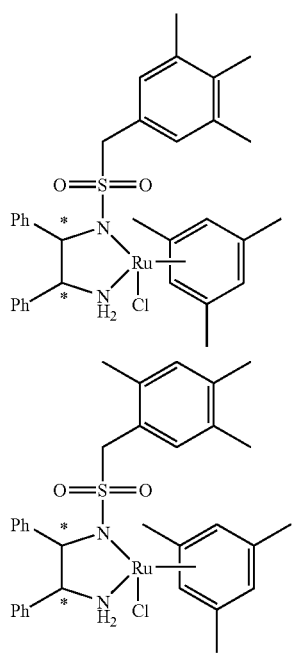
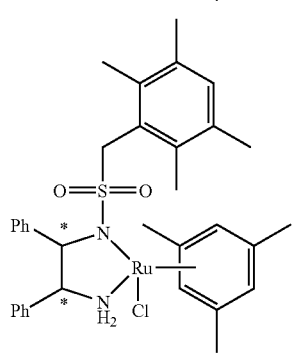
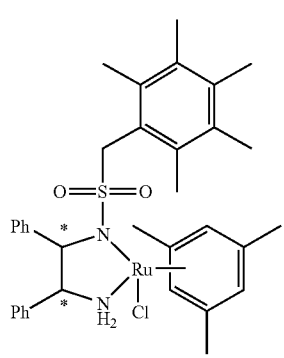
-continued
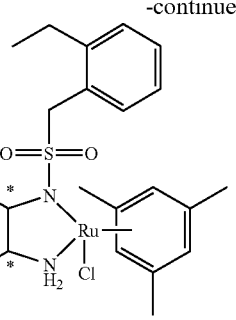
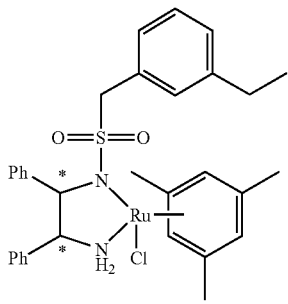
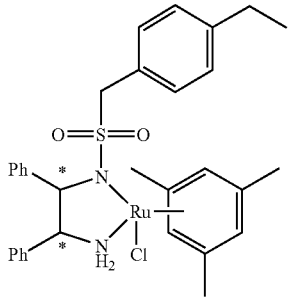
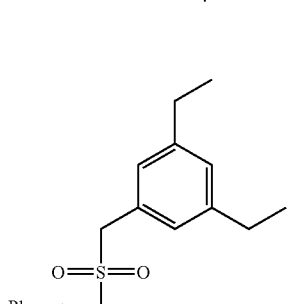

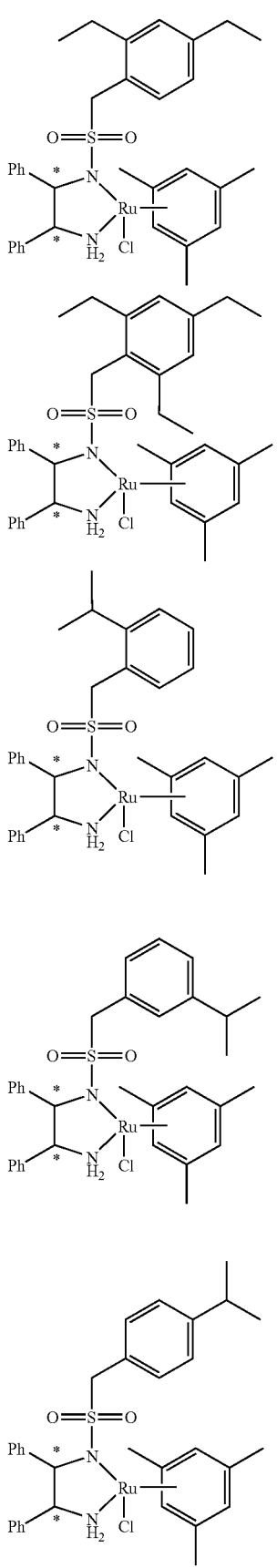
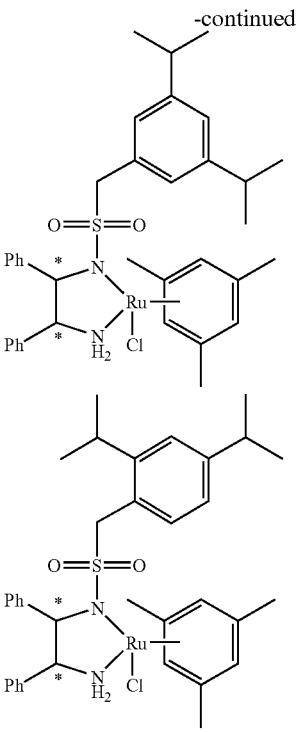

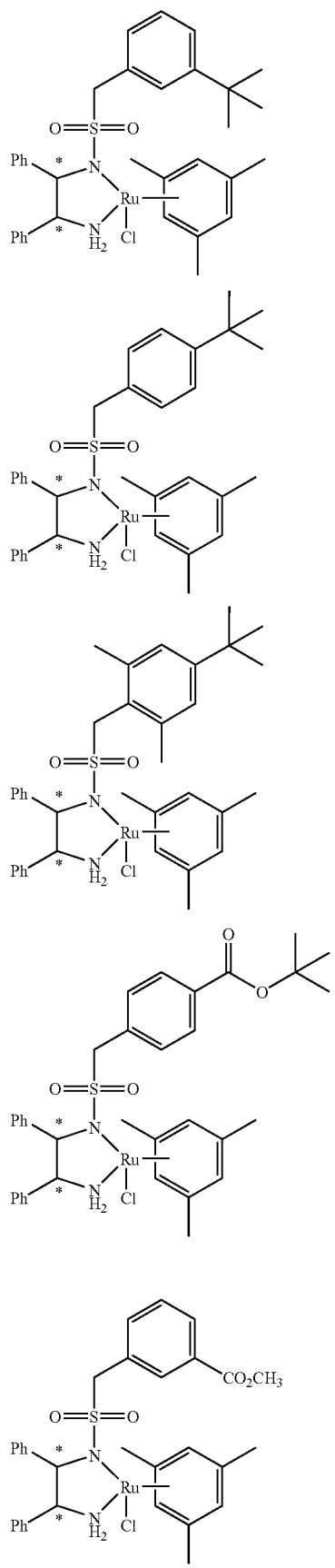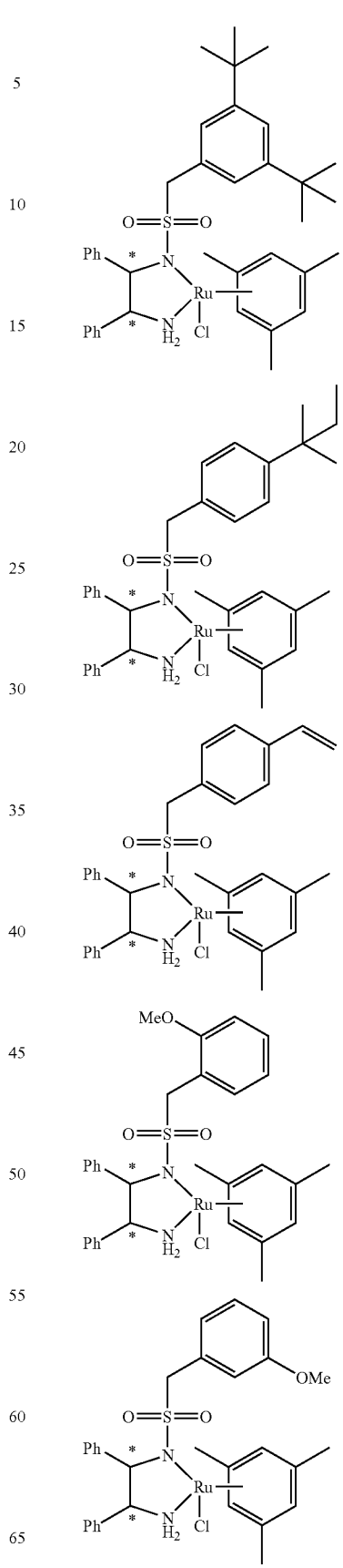

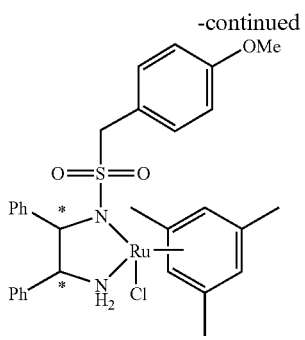
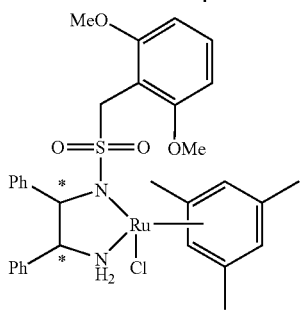
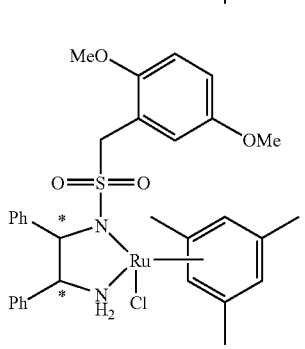
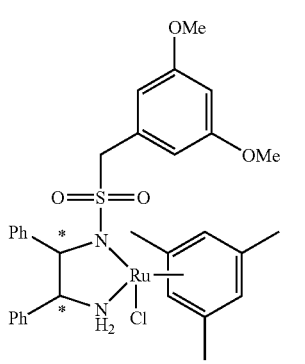
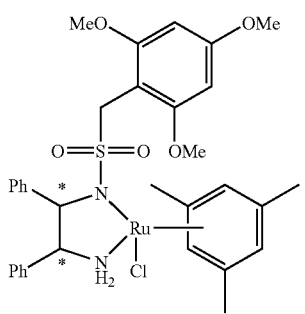
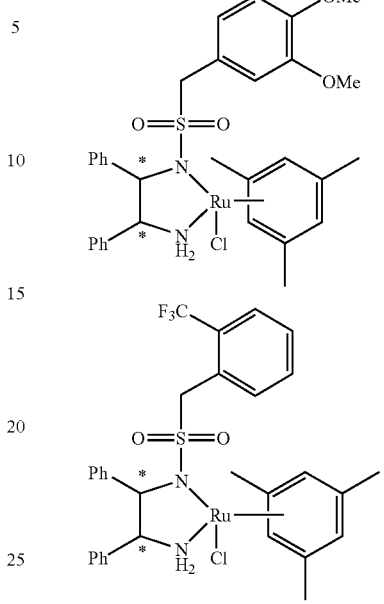
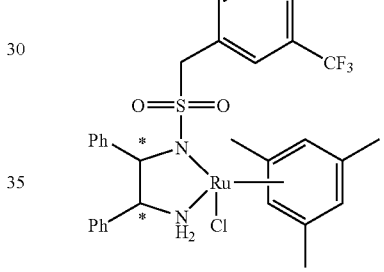
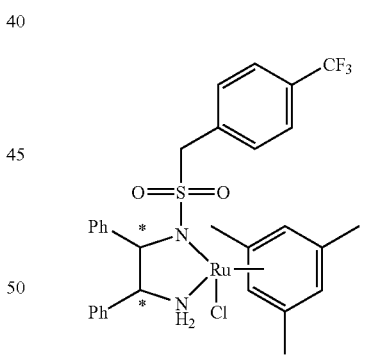
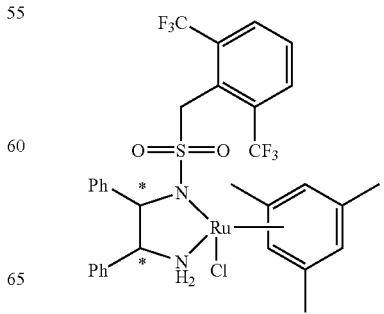

-continued
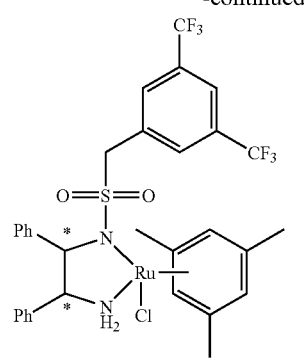
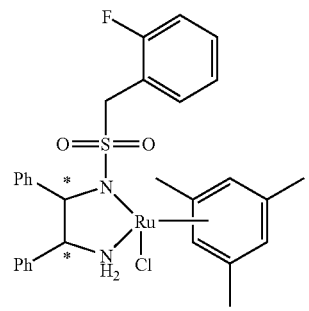
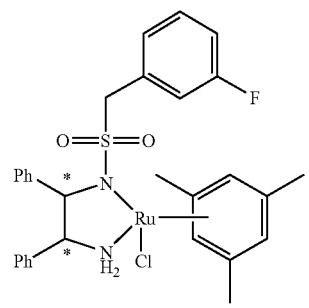
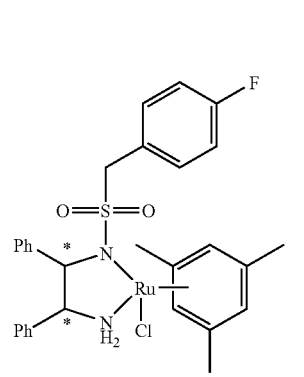
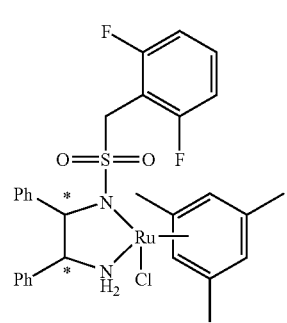
-continued
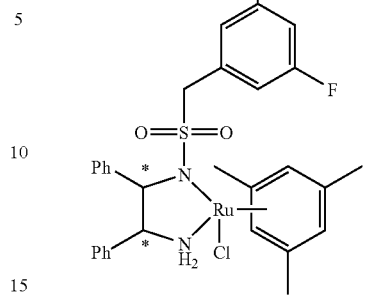
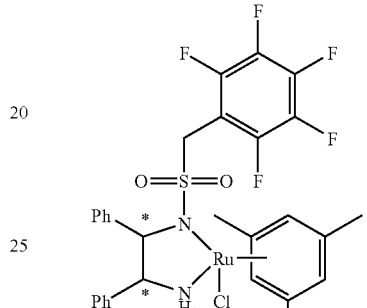
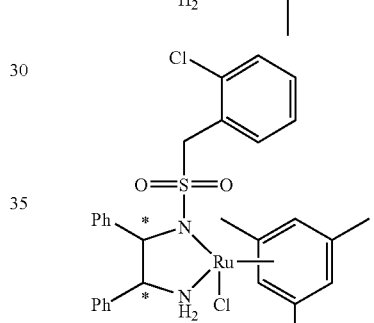
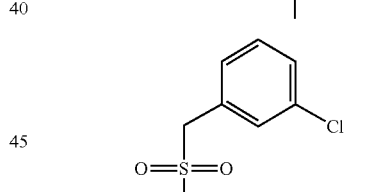
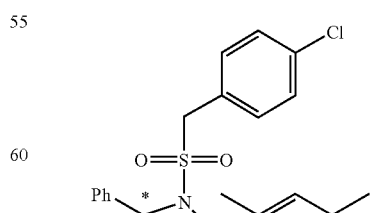
[Chem. 21]

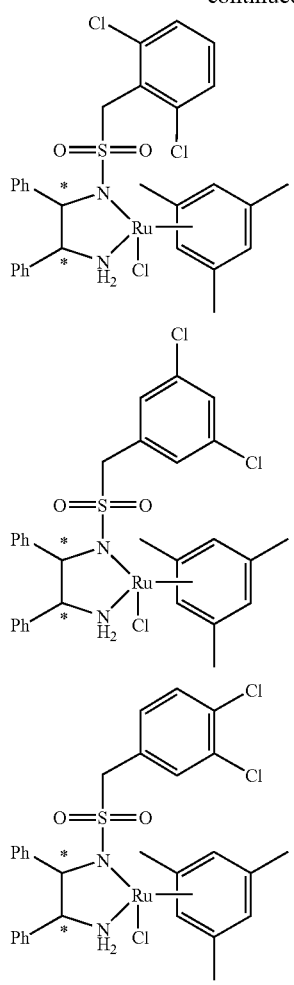
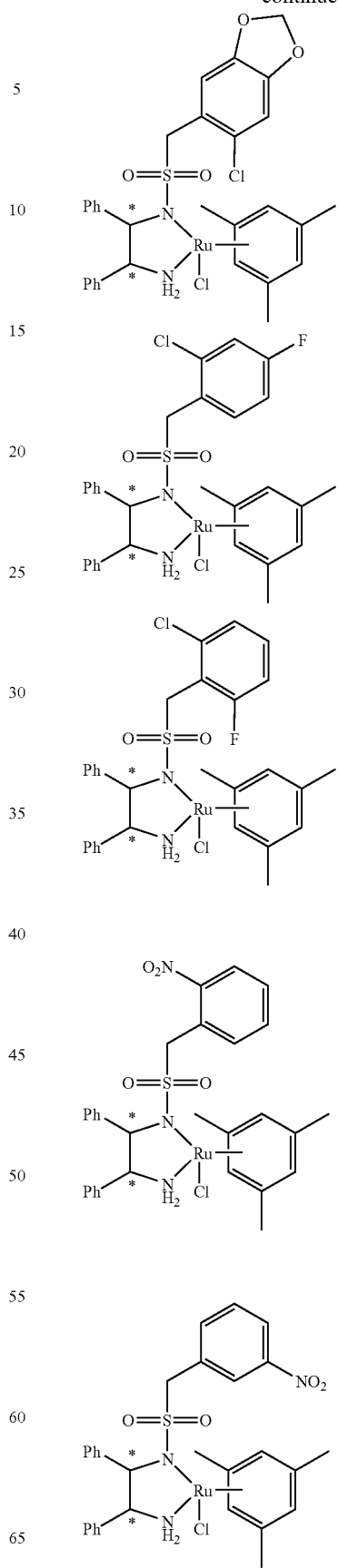

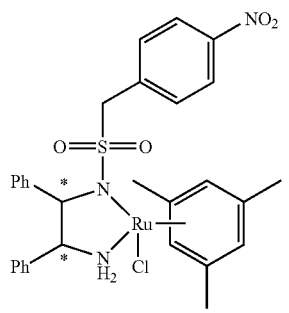
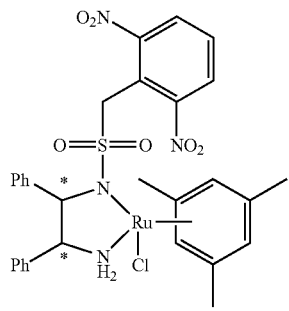
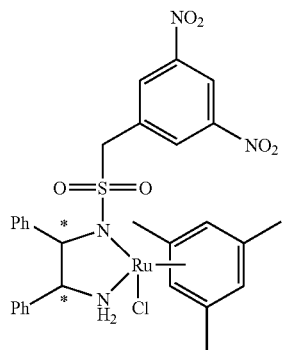
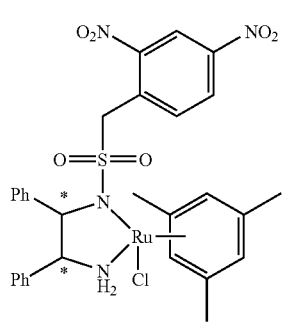
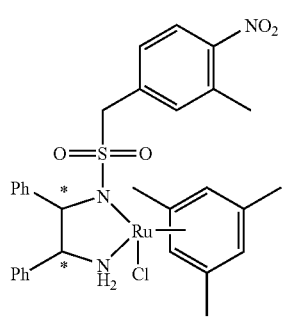
[Chem. 22]
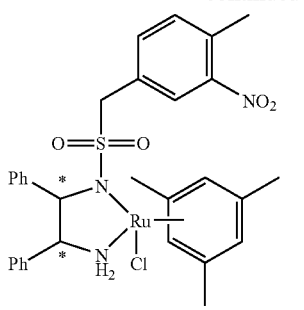
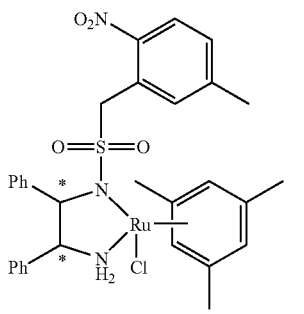
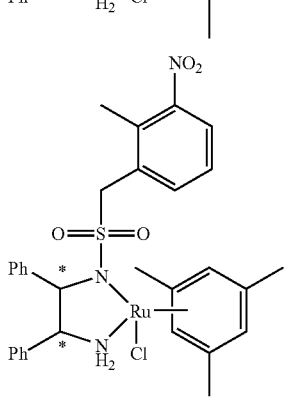
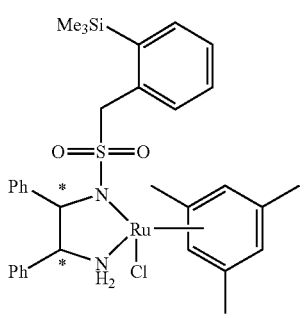
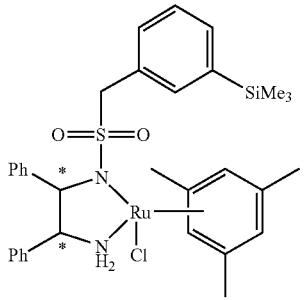

-continued
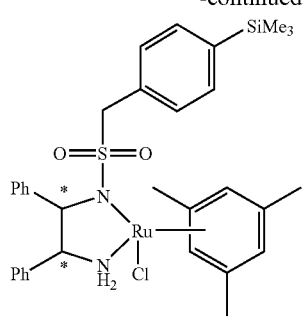
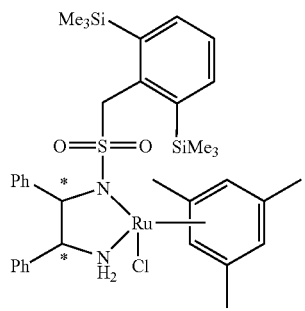
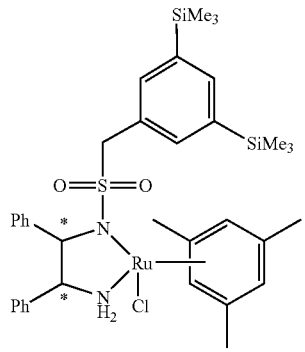
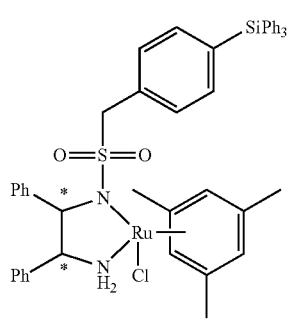
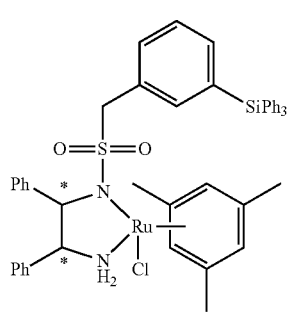
-continued
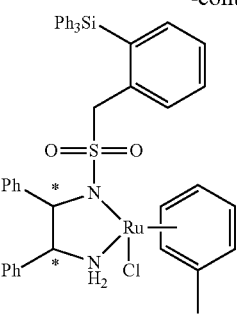
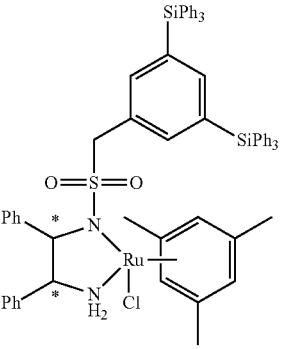
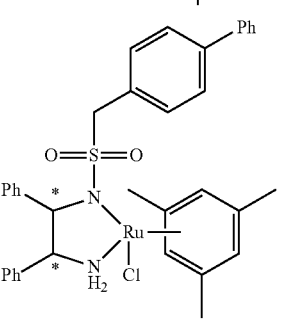
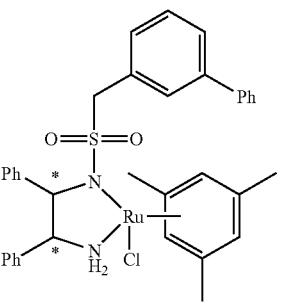
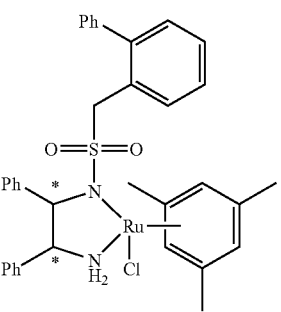

[Chem. 23]
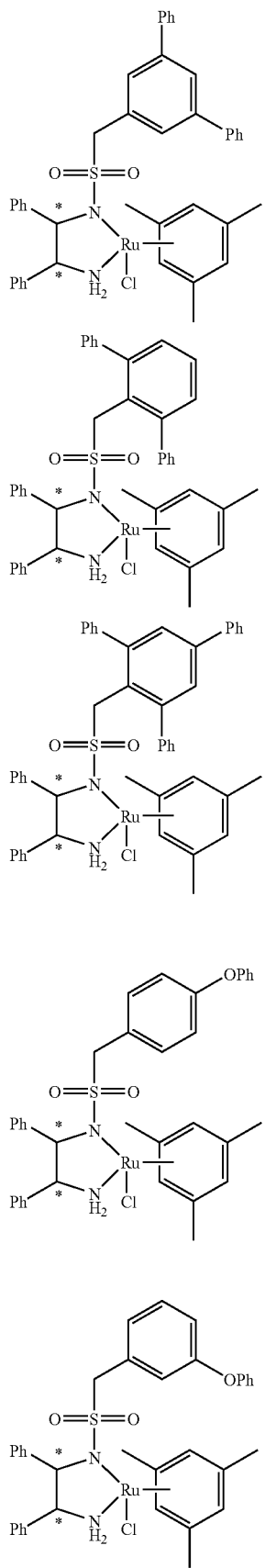
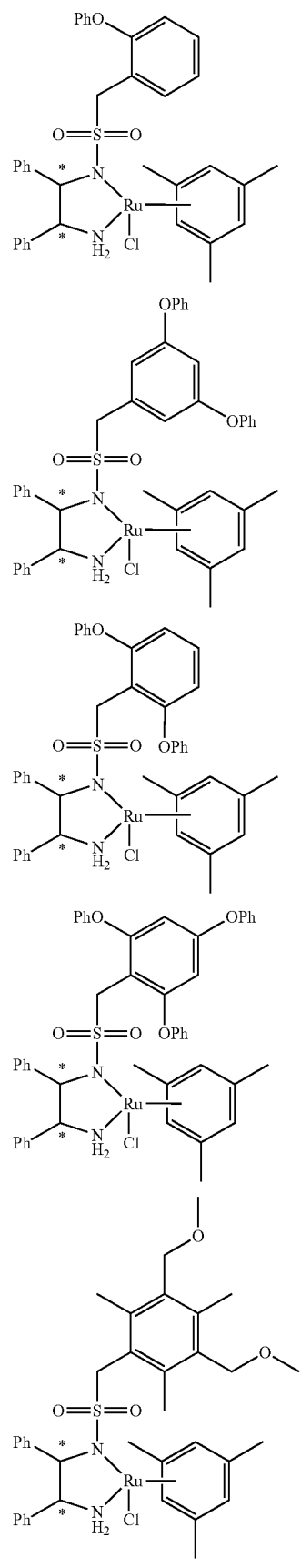

-continued
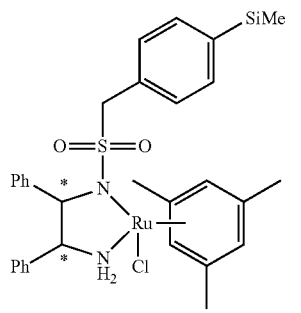
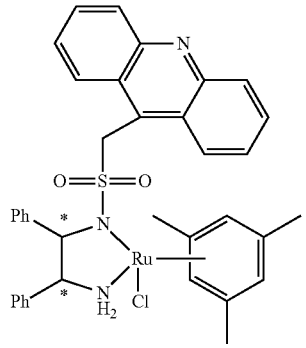
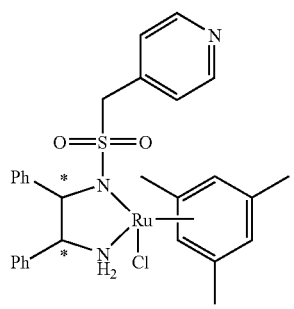
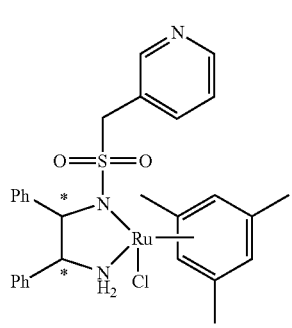
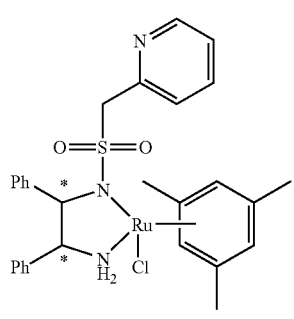
-continued
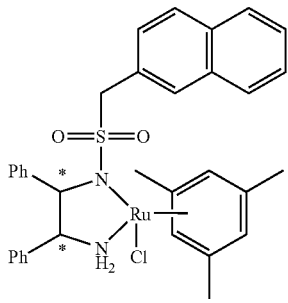
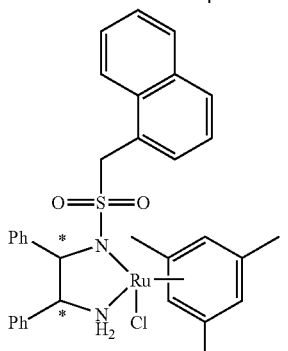
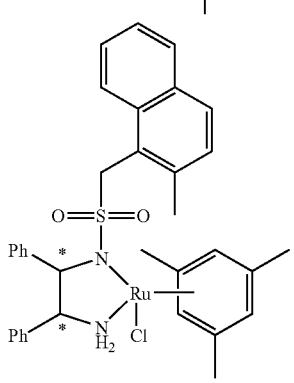
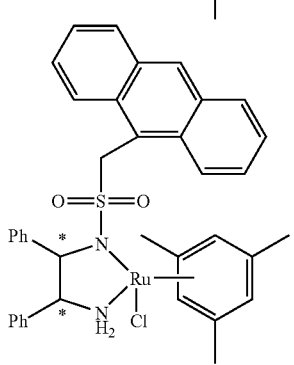
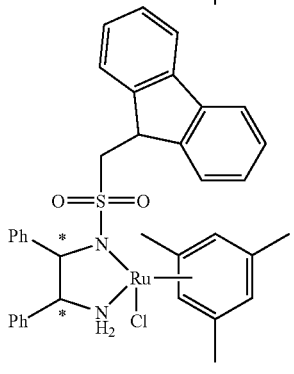
[Chem. 24]

73
-continued
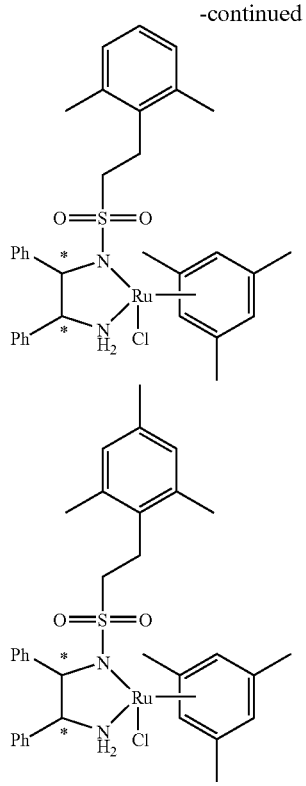
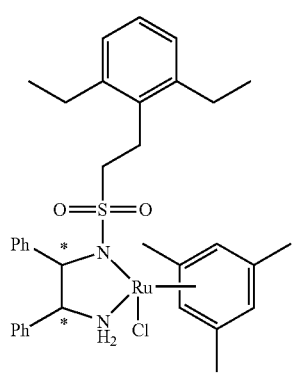
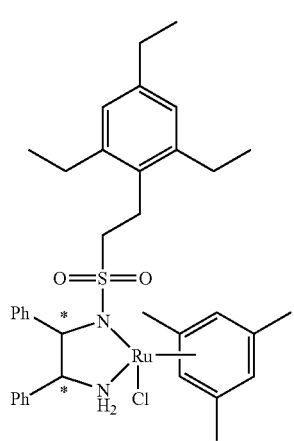
74
-continued
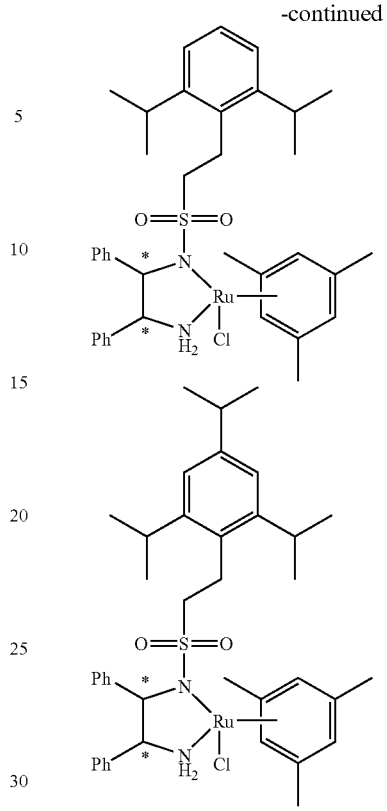
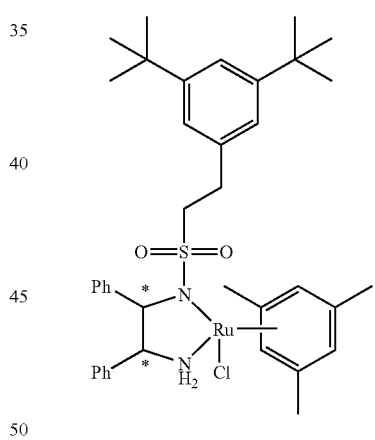
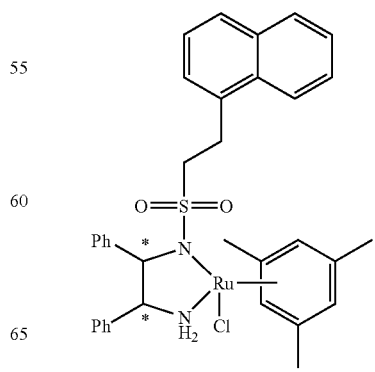

75
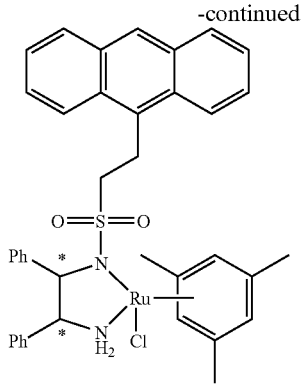
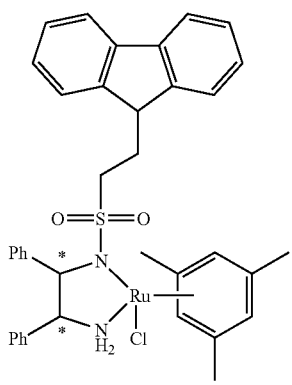
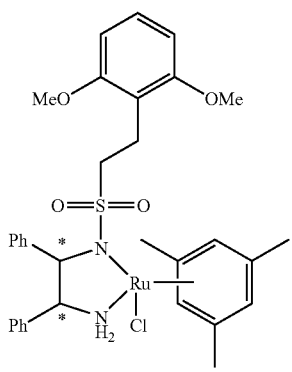
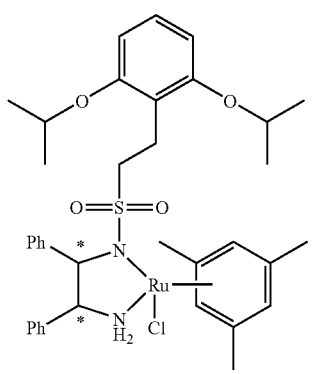
76
-continued
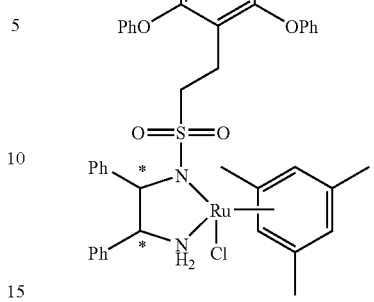
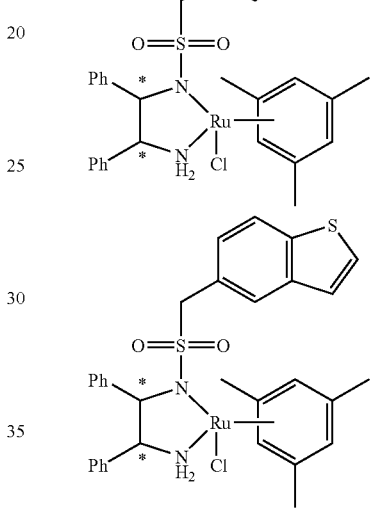
[Chem. 25]
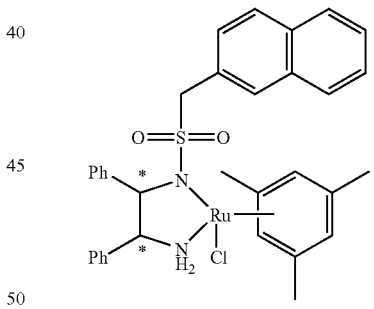
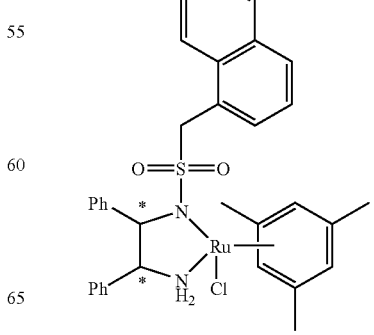

77
-continued
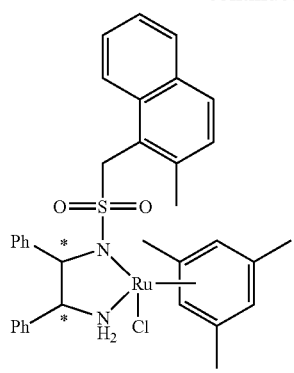
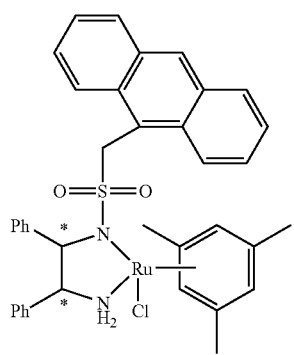
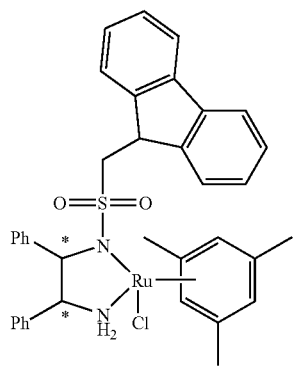
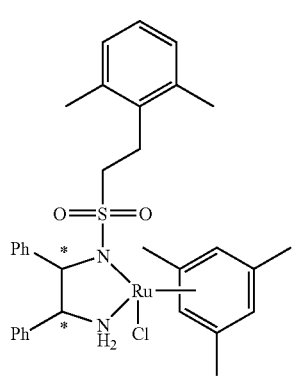
78
-continued
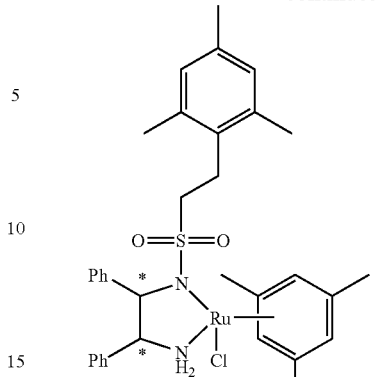
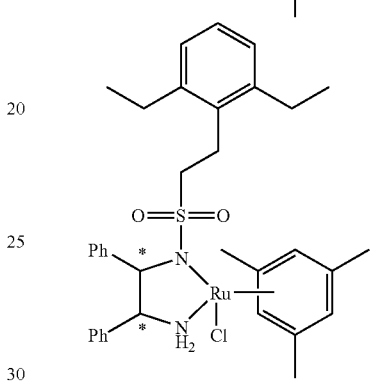
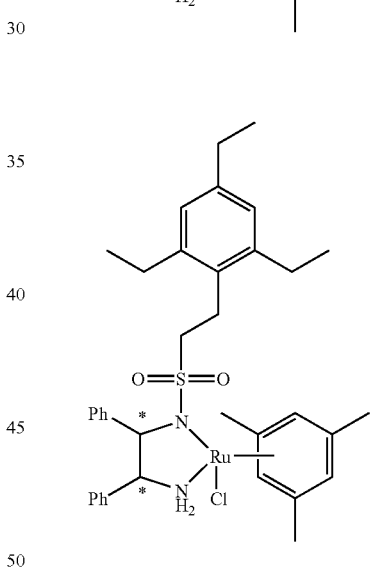
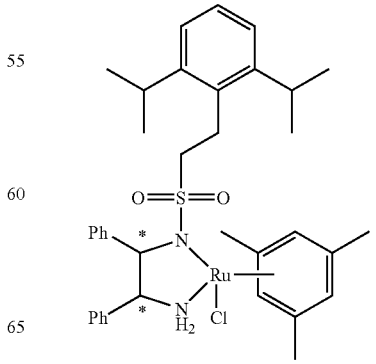

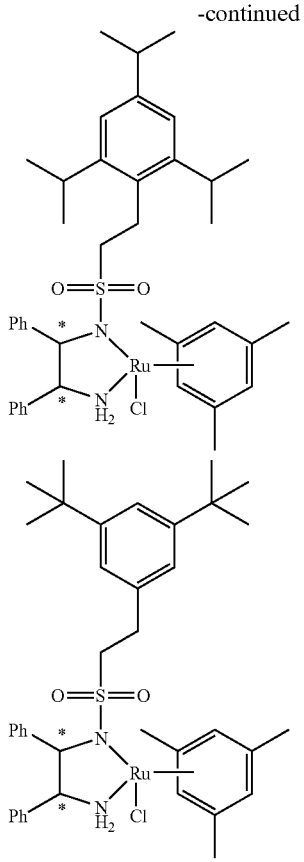
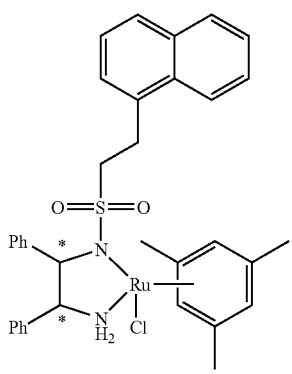
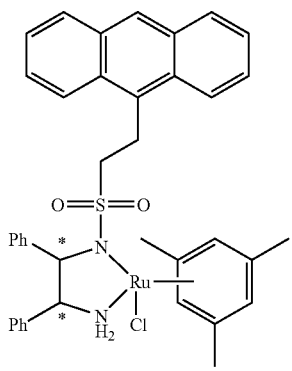
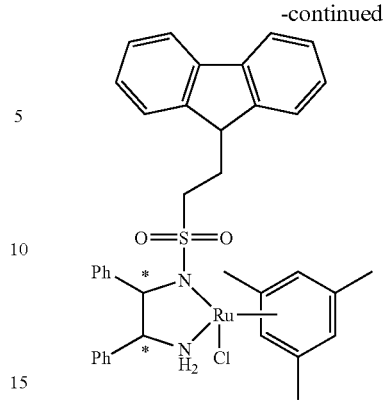
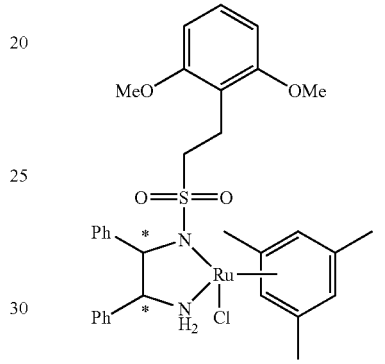
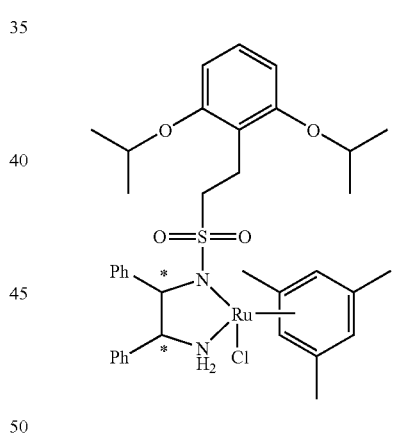
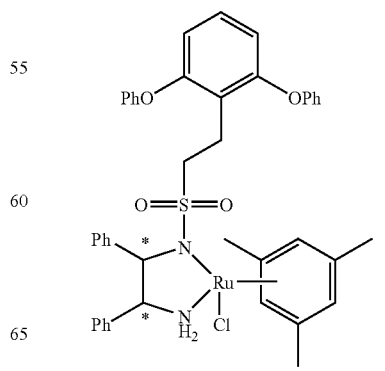

-continued
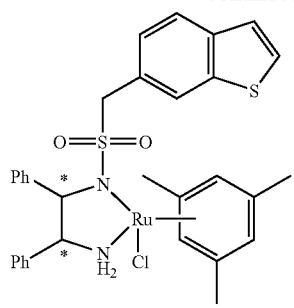
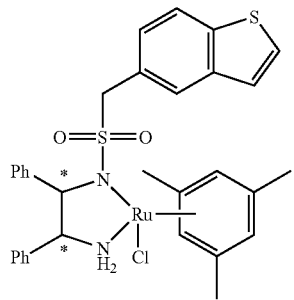
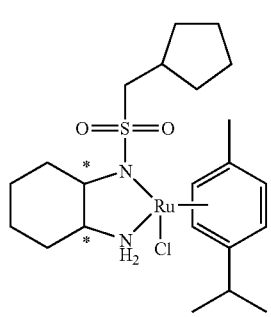
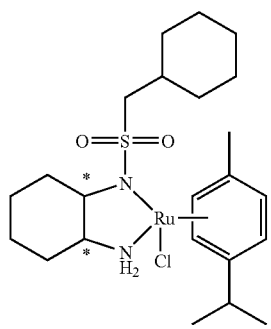
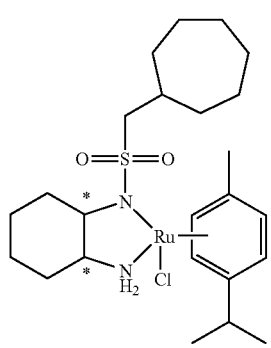
-continued
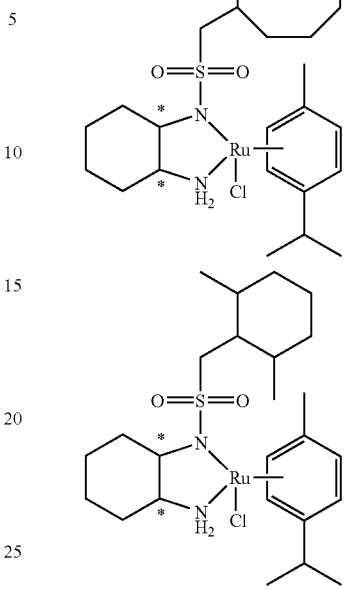
[Chem. 26]
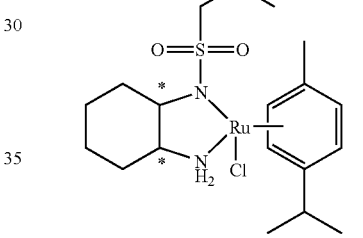
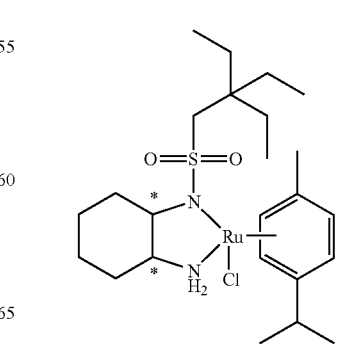
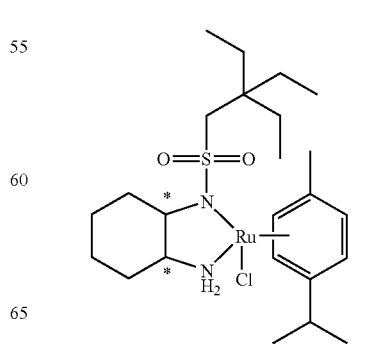

83
-continued
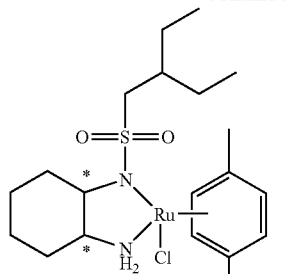
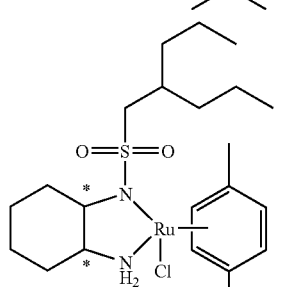
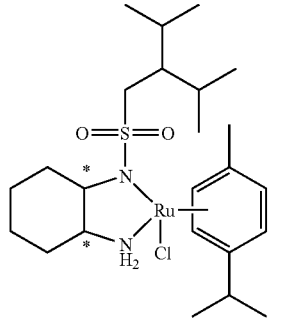
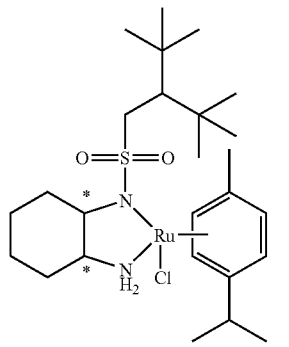
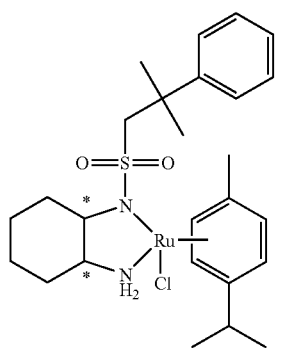
84
-continued
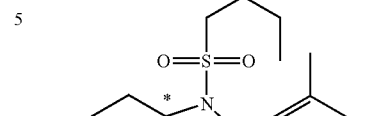
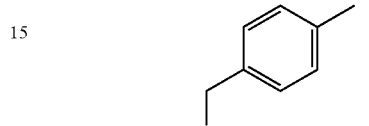
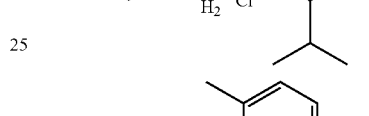
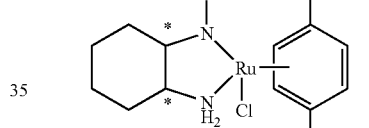
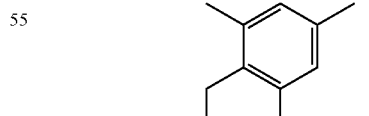
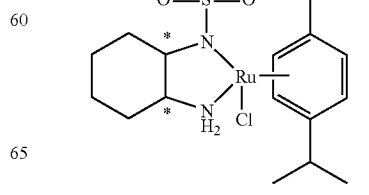

85
-continued
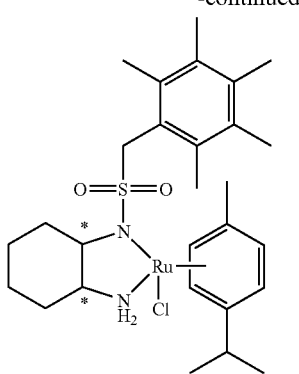
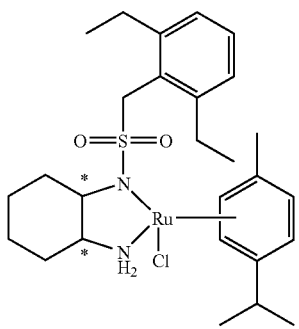
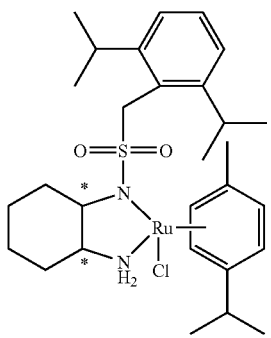
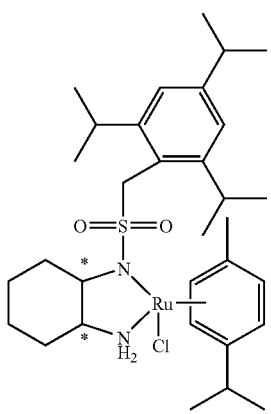
86
-continued
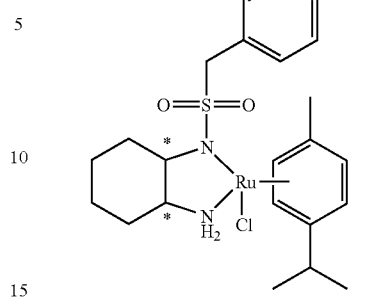
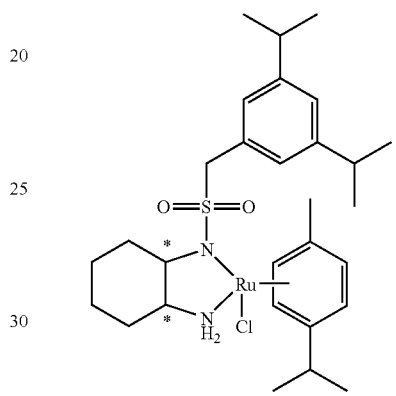
[Chem. 27]
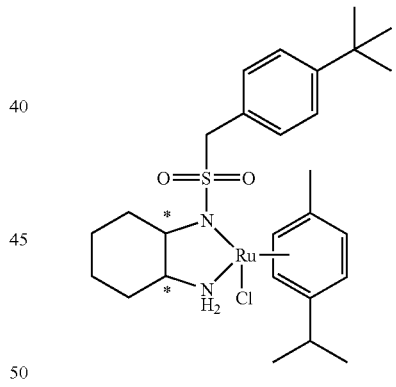
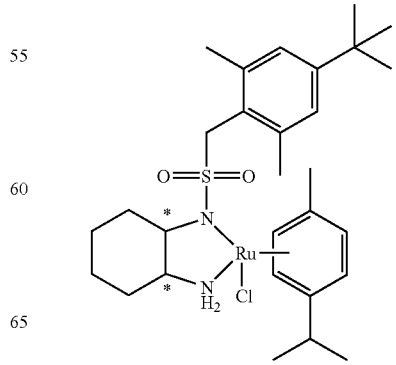

87
-continued
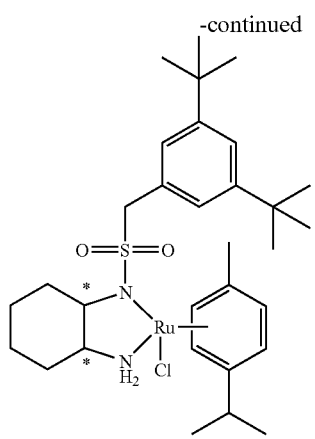
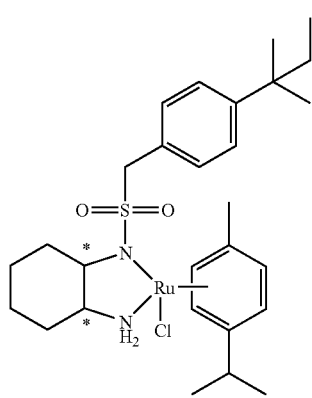
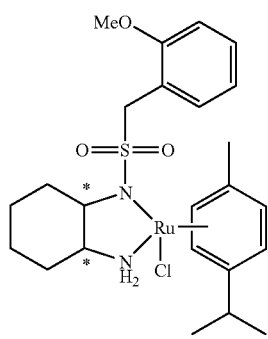
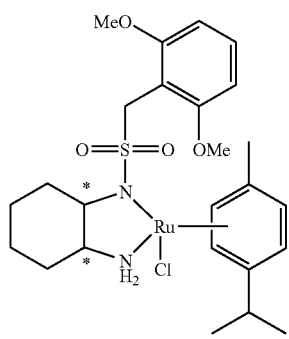
88
-continued
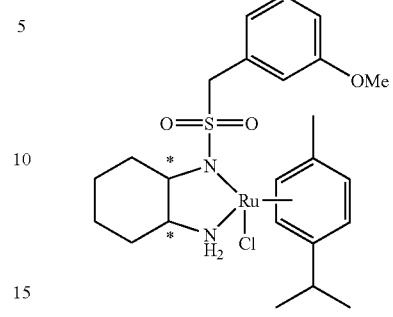
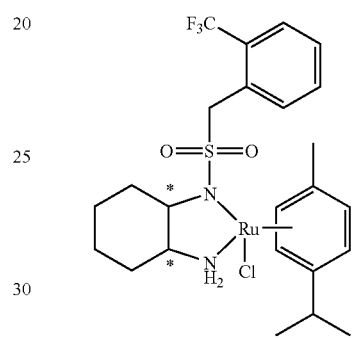
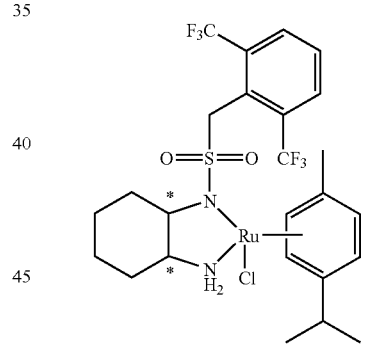
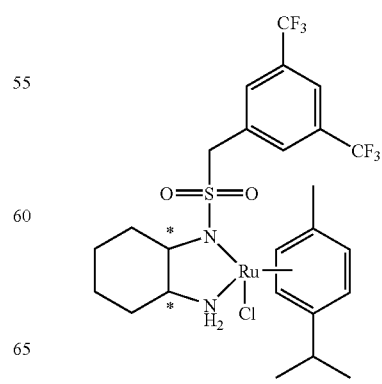

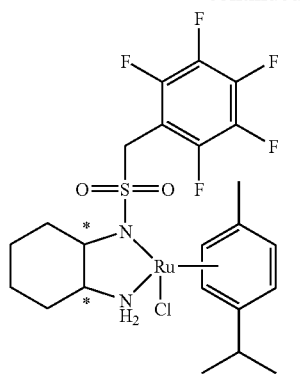
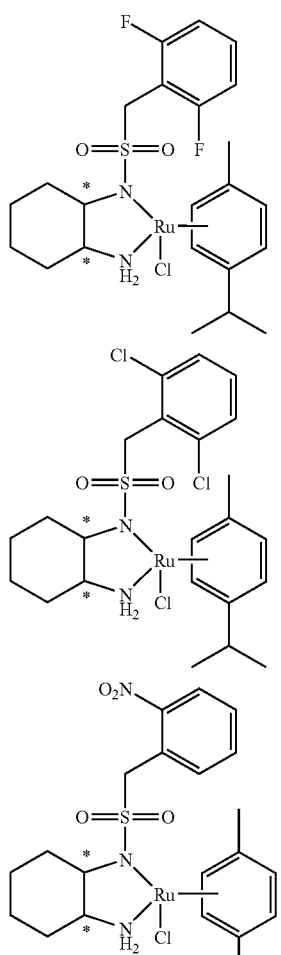
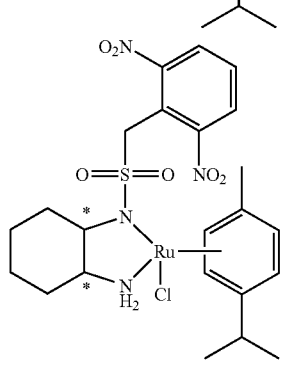
[Chem. 28]
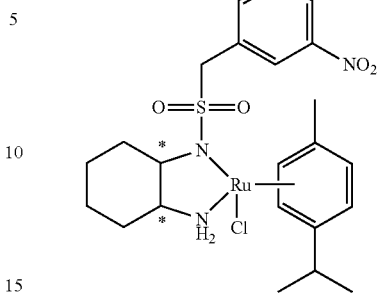
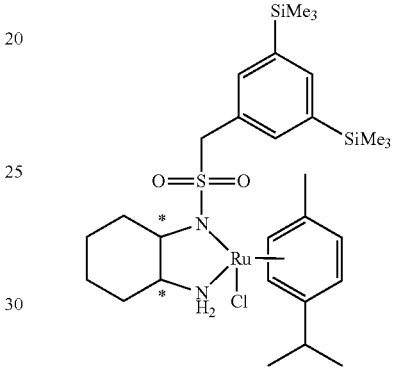
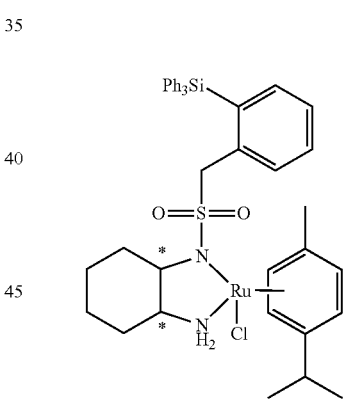
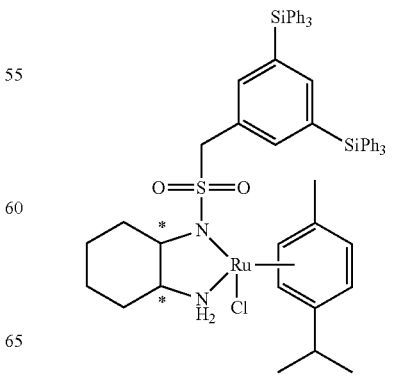

-continued
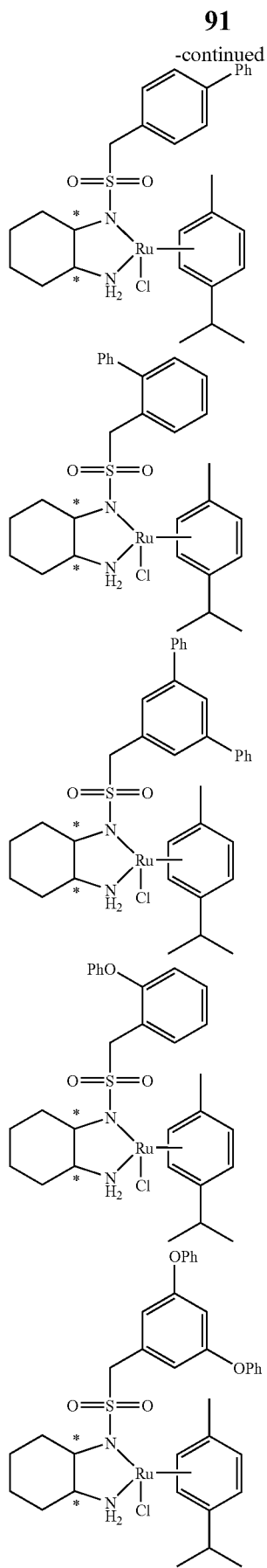
-continued
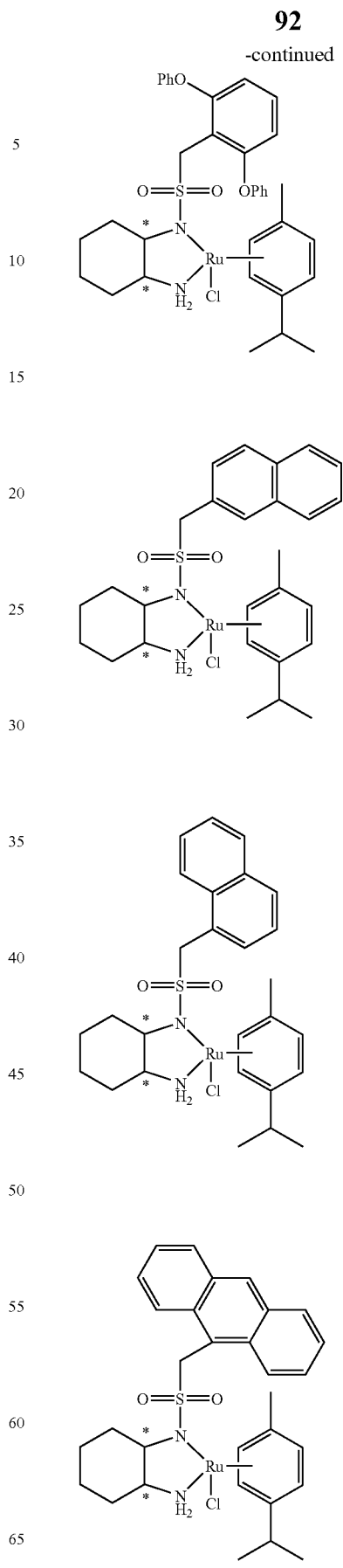

-continued
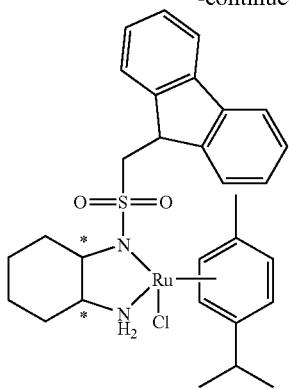
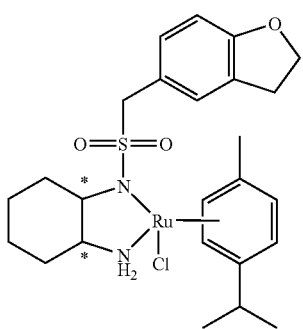
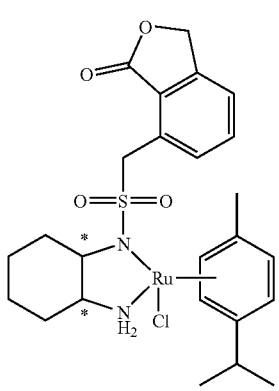
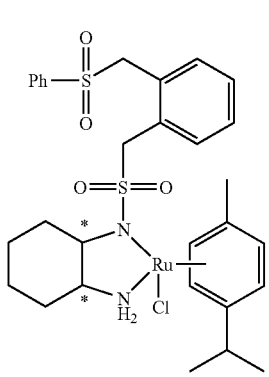
-continued
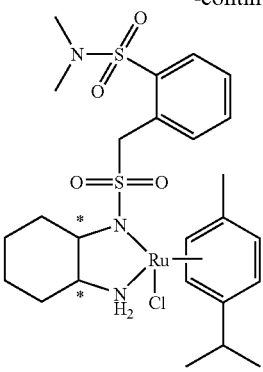
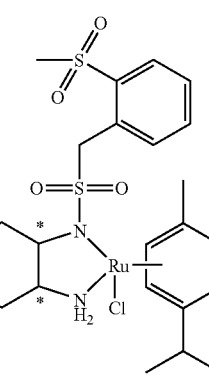
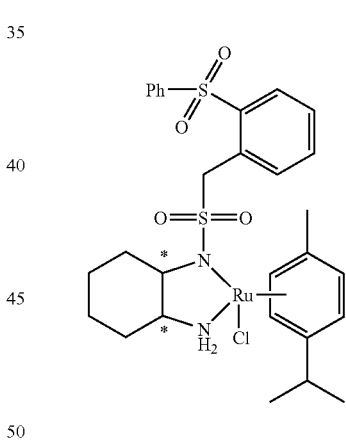
[Chem. 29]
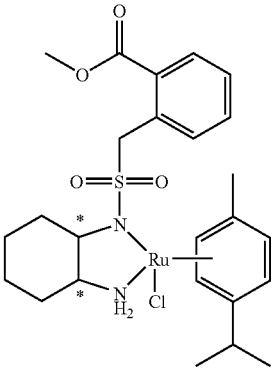

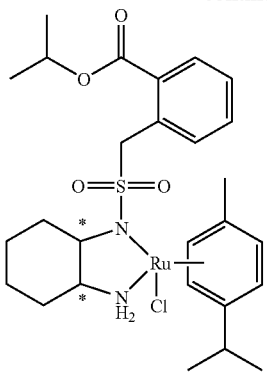
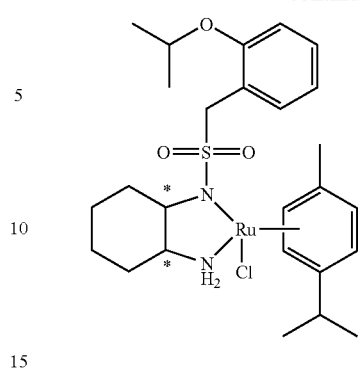
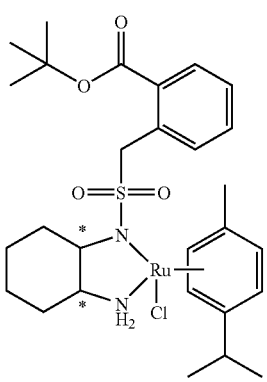
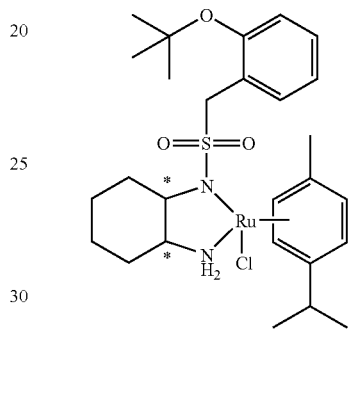
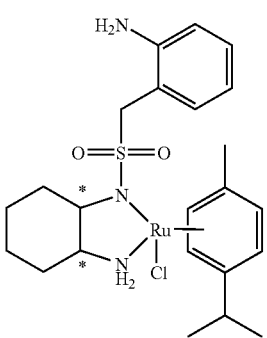
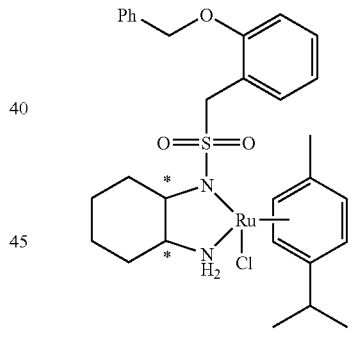
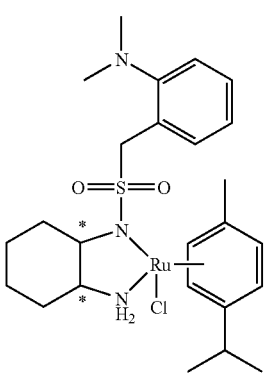
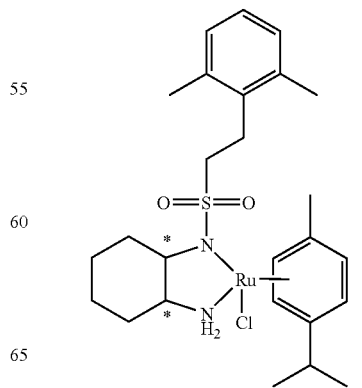

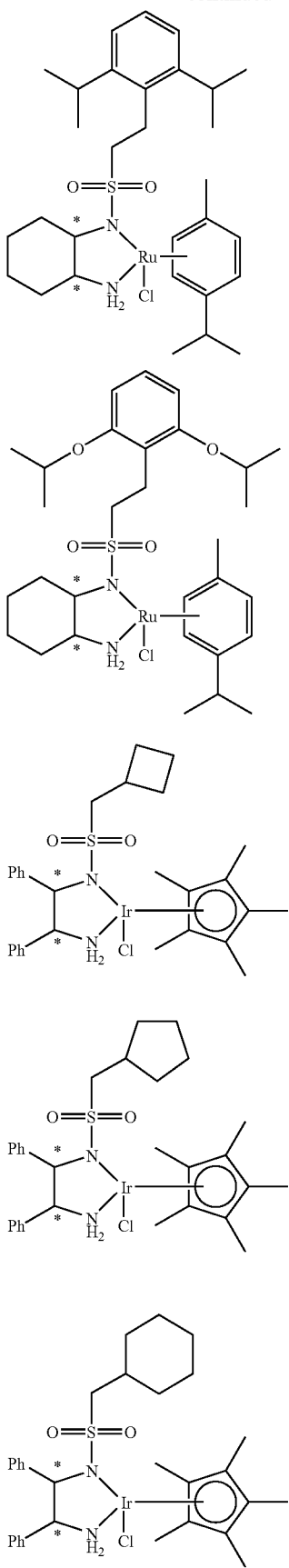
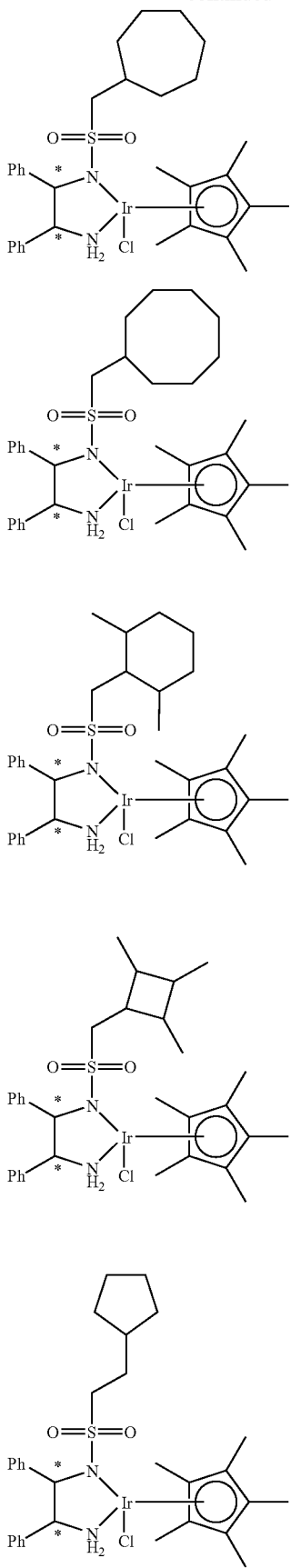

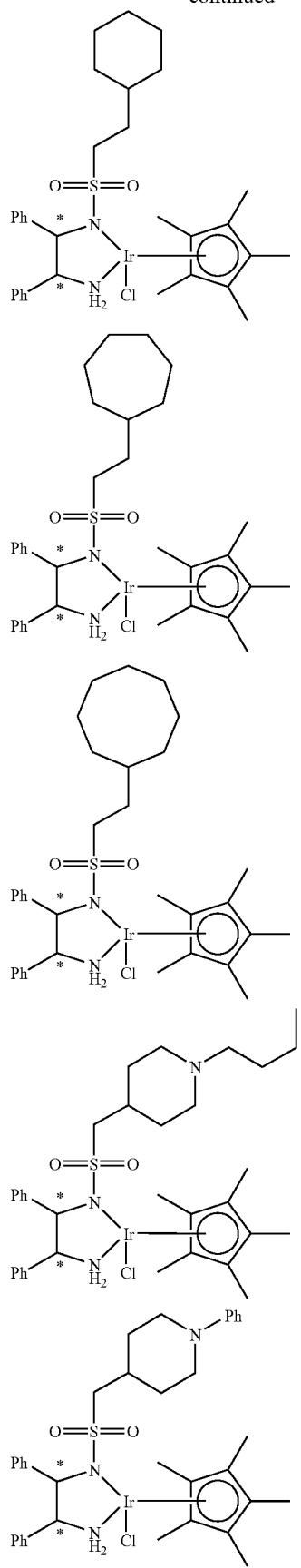
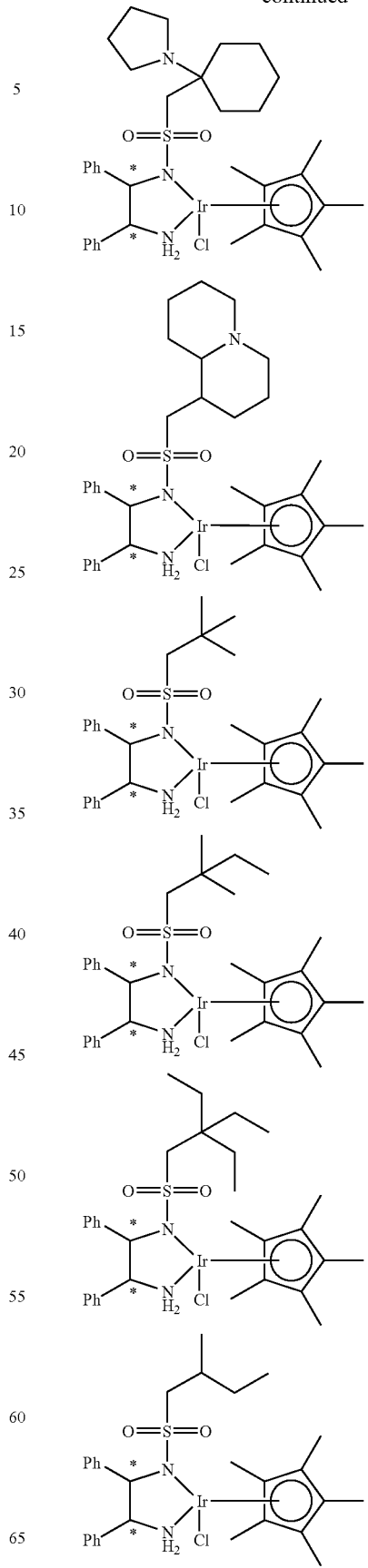

101
-continued
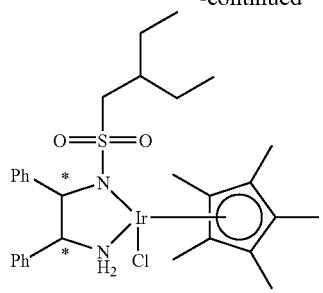
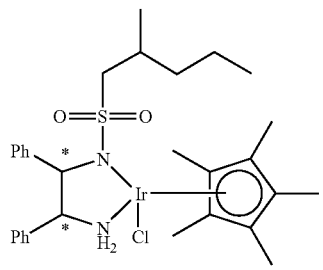
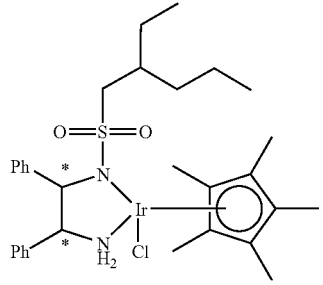
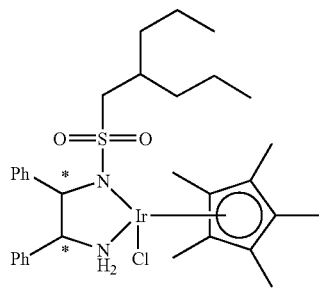
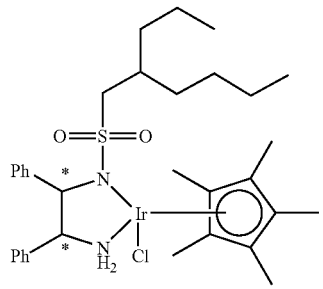
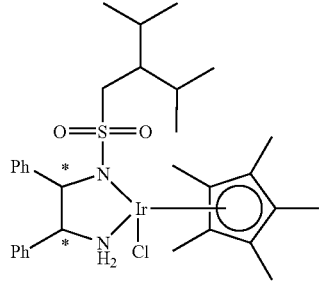
102
-continued
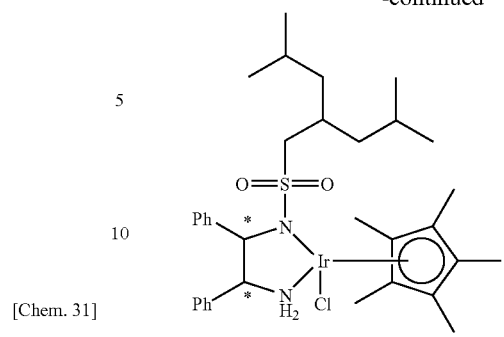
[Chem. 31]
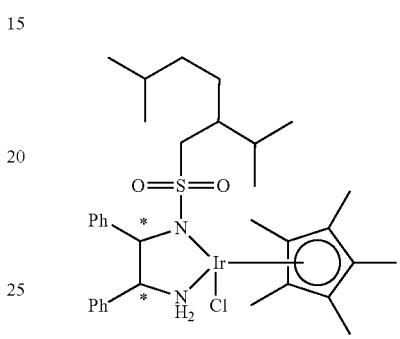
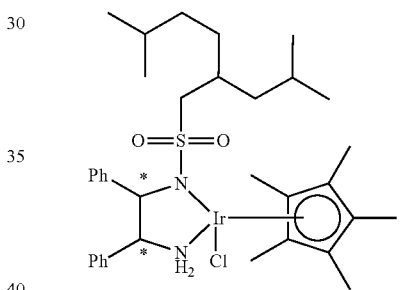
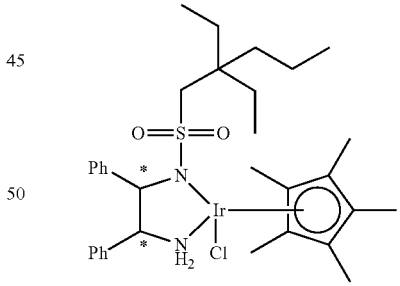
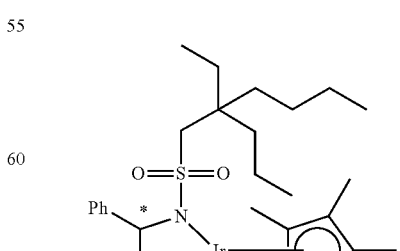

103
-continued
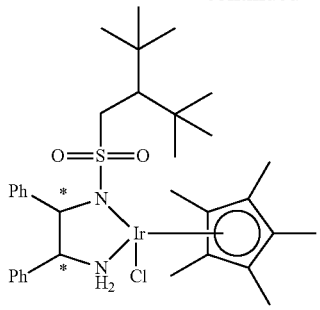
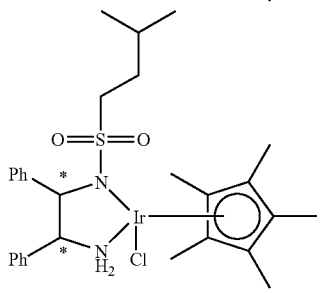
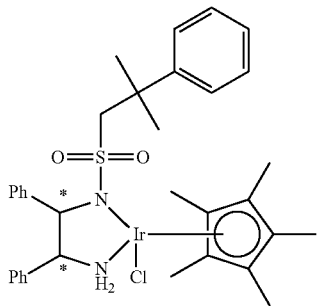
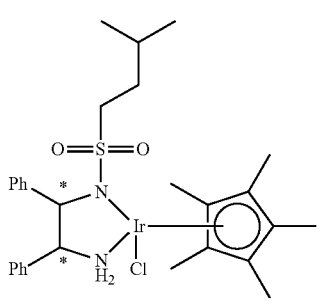
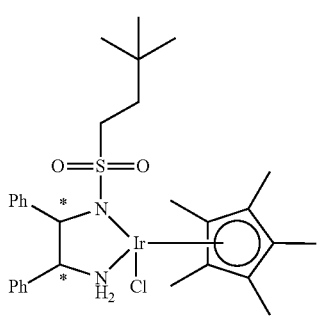
104
-continued
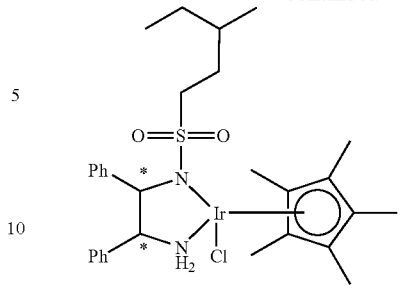
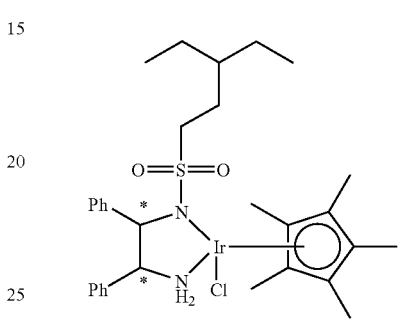
[Chem. 32]
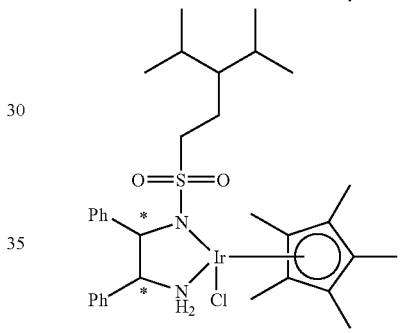
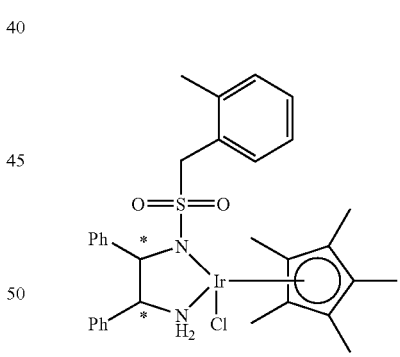
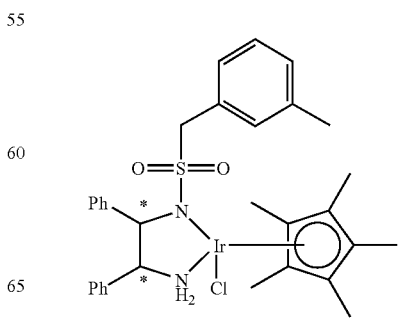

-continued
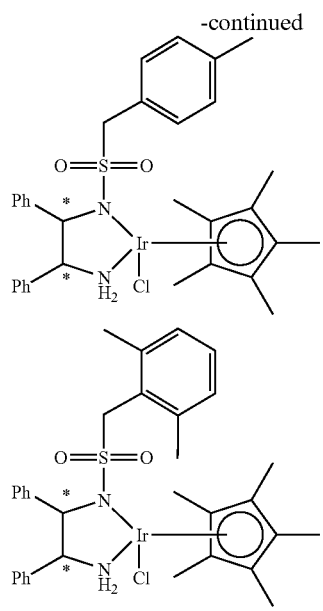
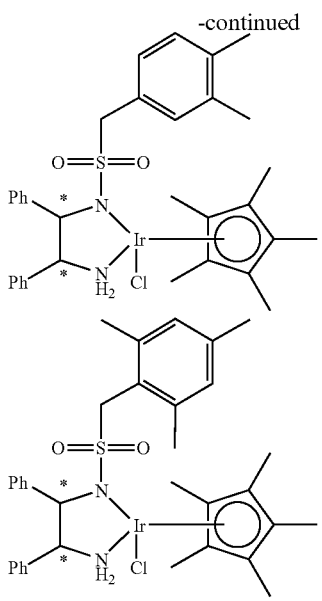
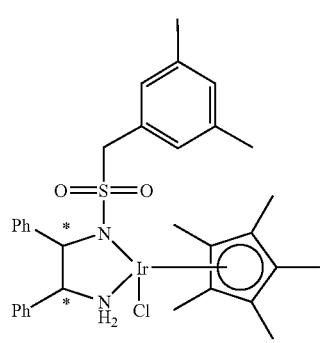
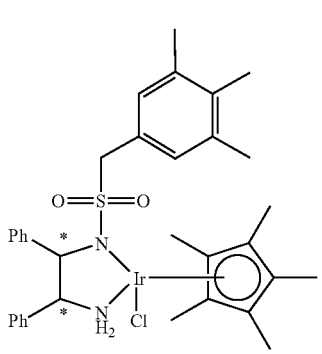
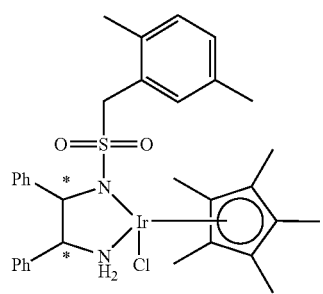
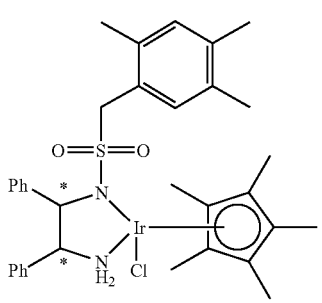
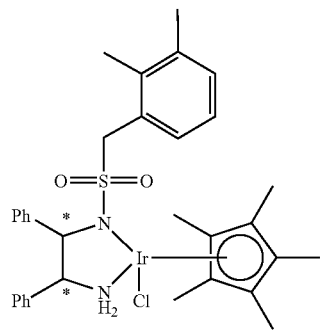
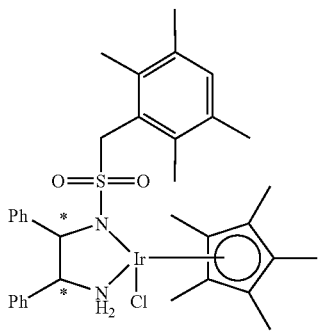

107
-continued
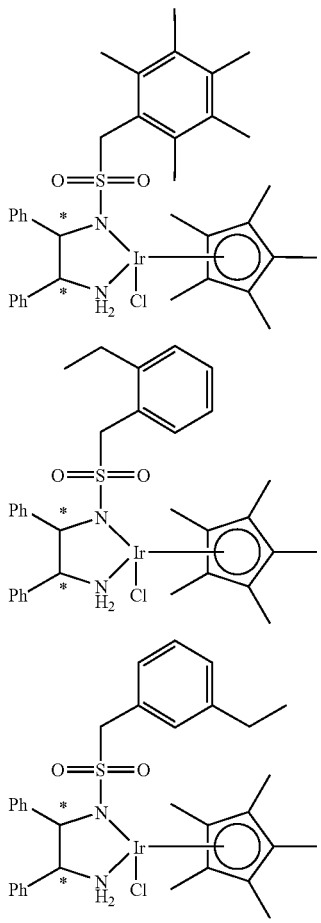
108
-continued
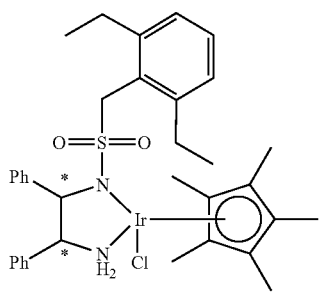
[Chem. 33]
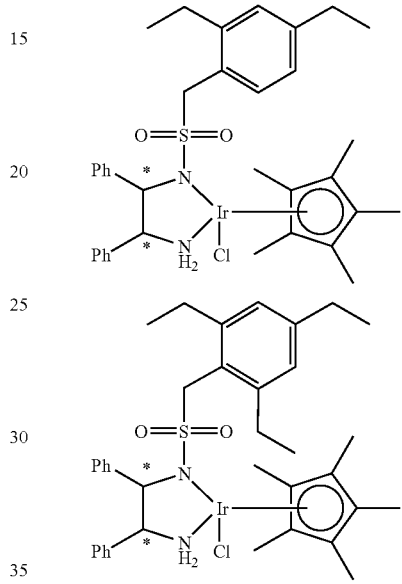

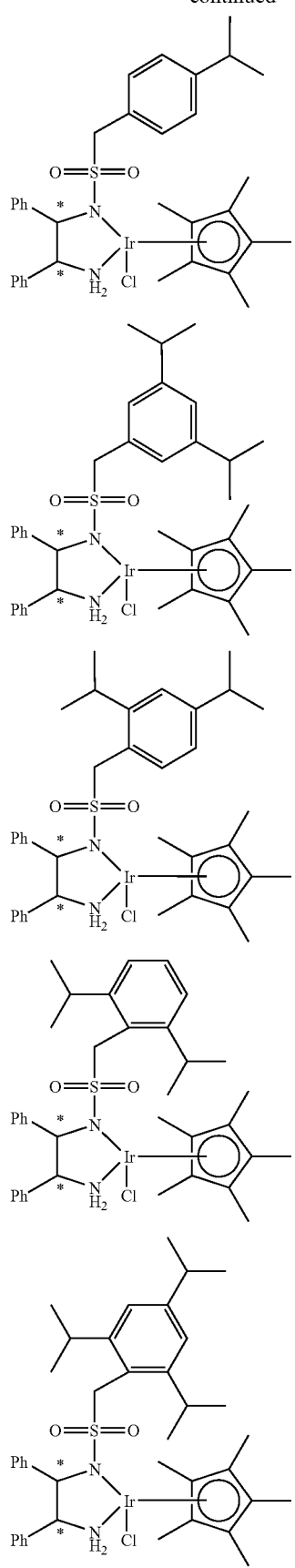
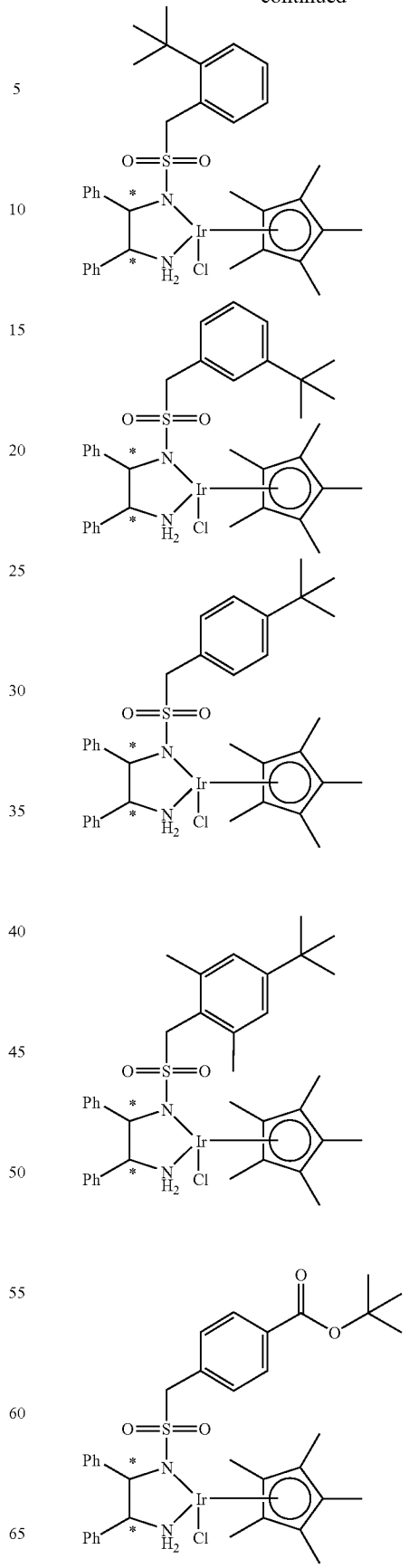

111
-continued
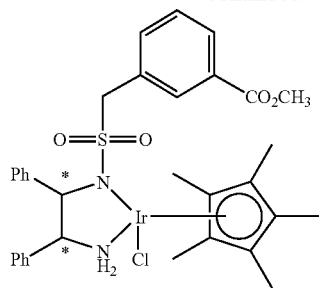
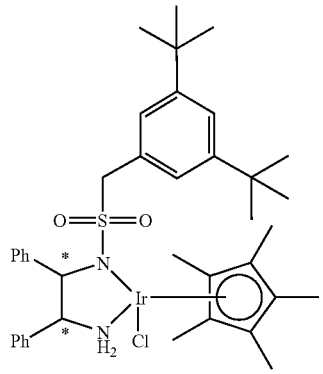
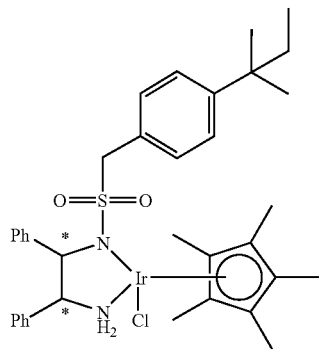
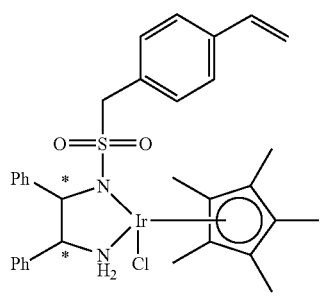
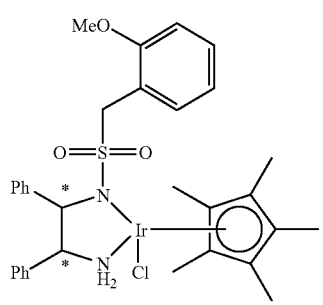
112
-continued
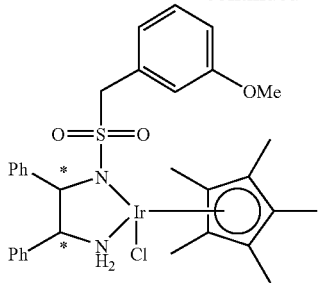
[Chem. 34]
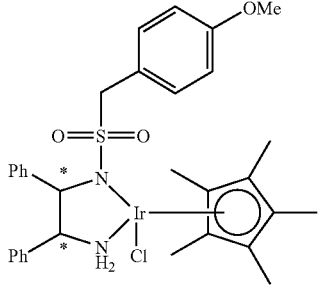
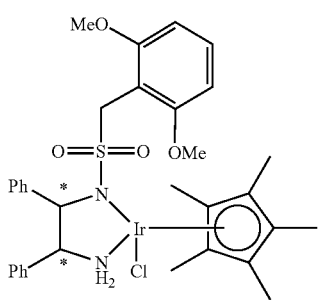
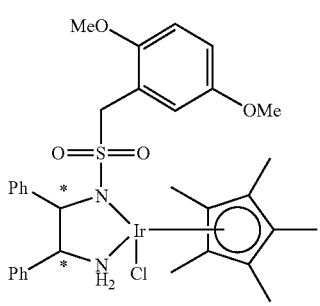
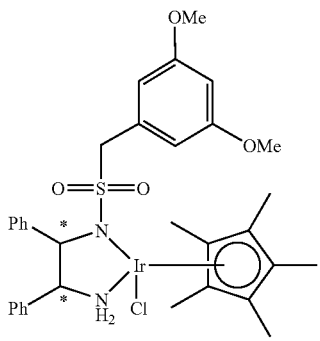

113
-continued
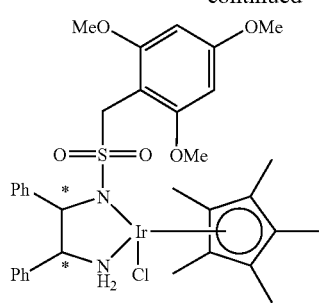
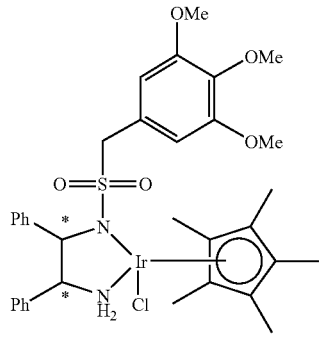
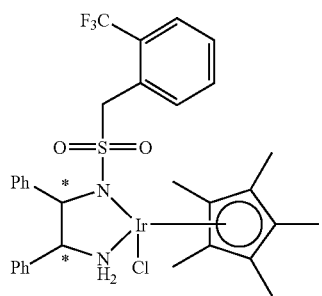
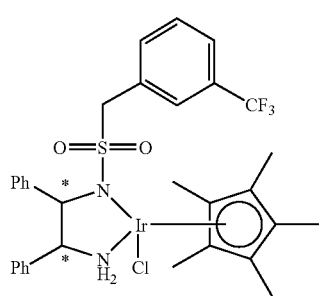
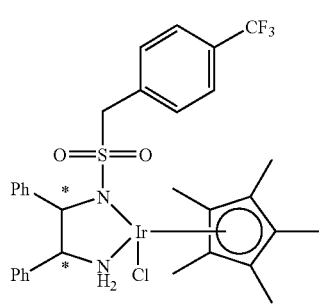
114
-continued
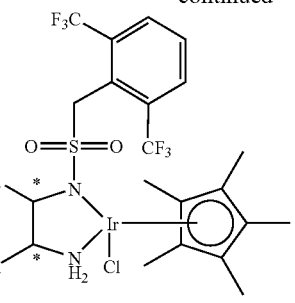
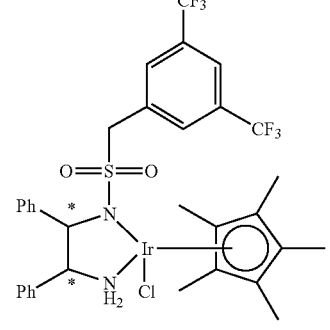
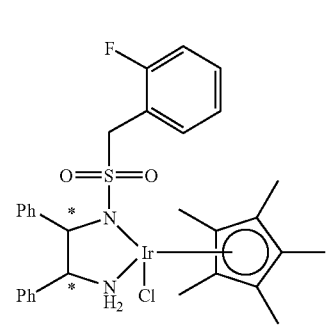
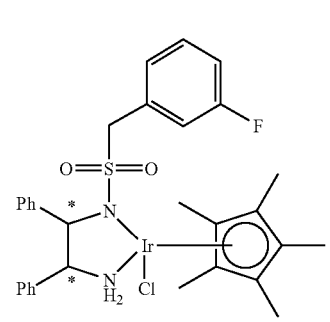
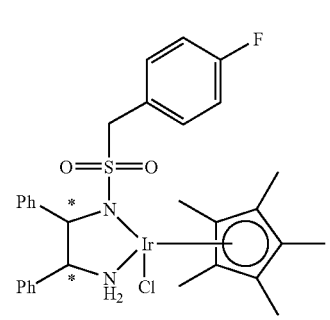

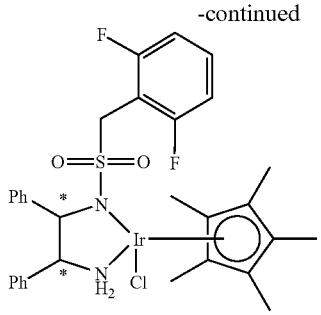
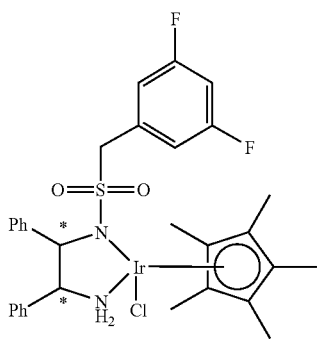
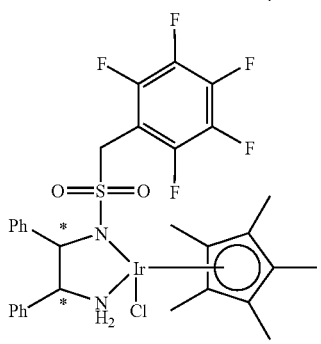
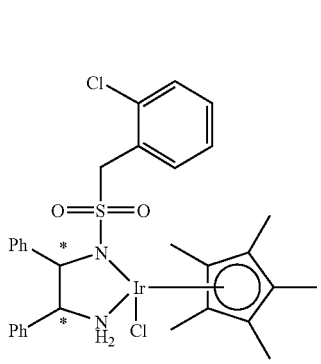
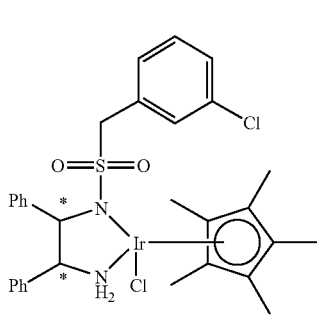
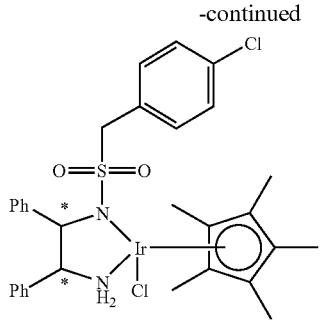
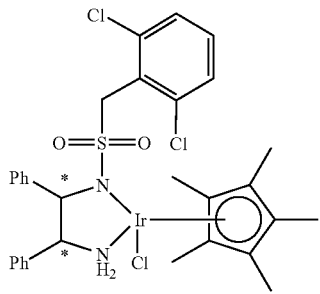
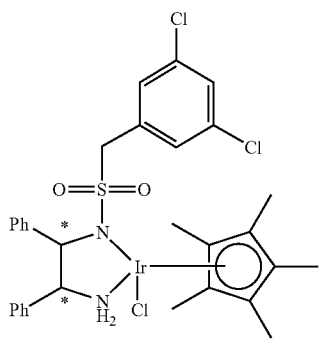
[Chem. 35]
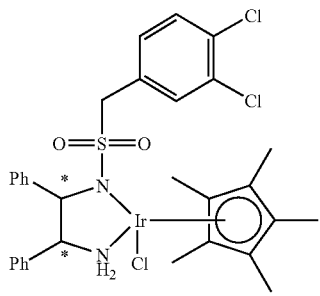
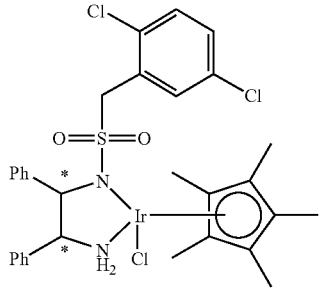

117
-continued
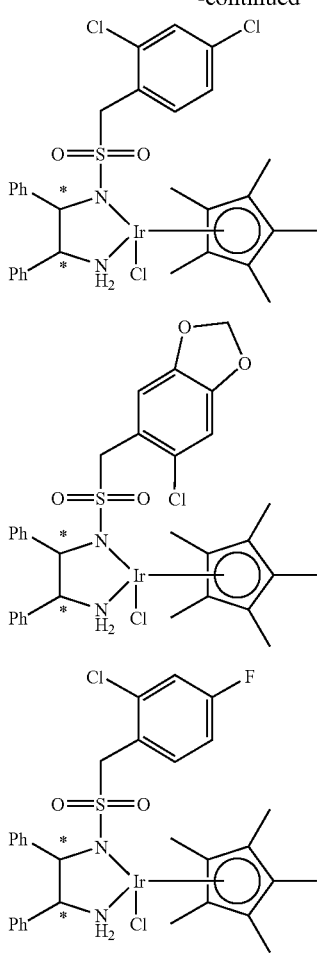
118
-continued
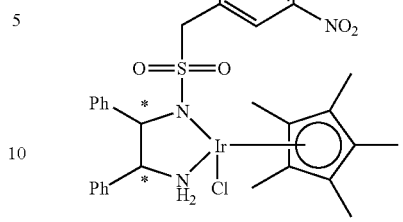
[Chem. 36]
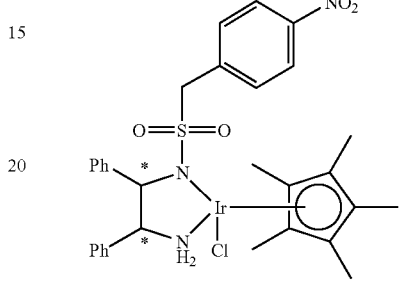
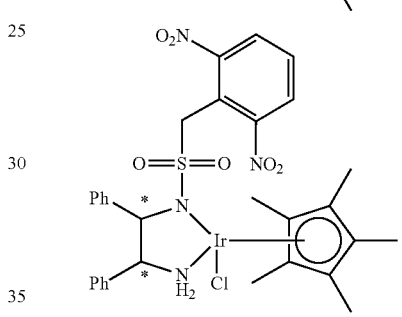
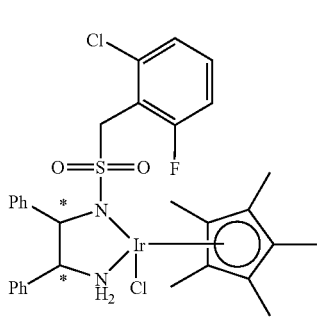
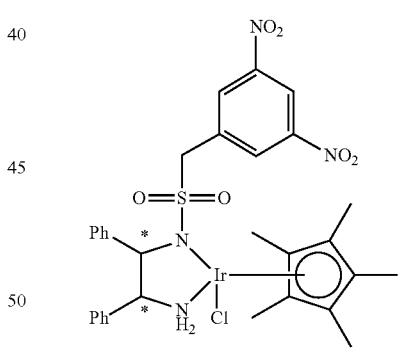
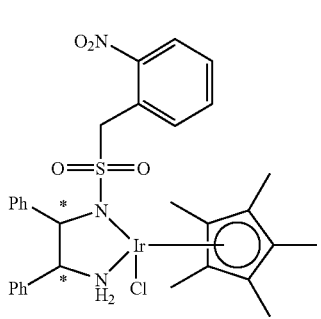
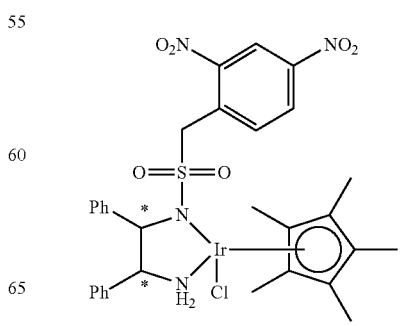

-continued
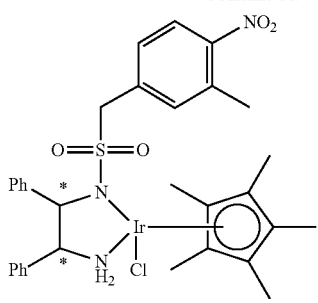
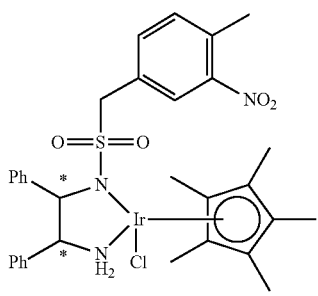
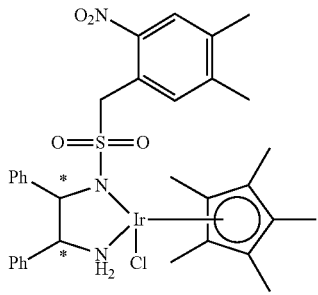
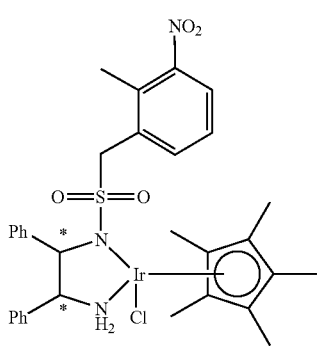
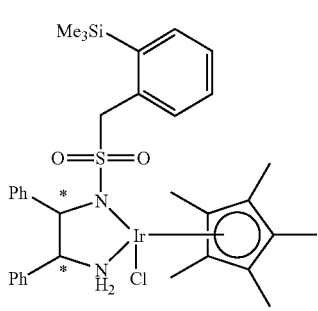
-continued
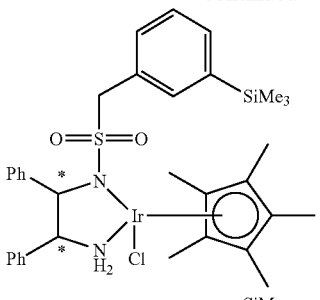
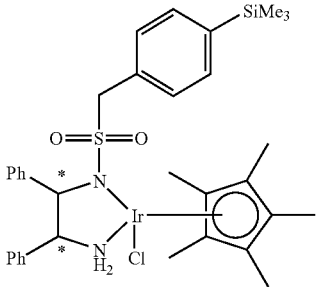
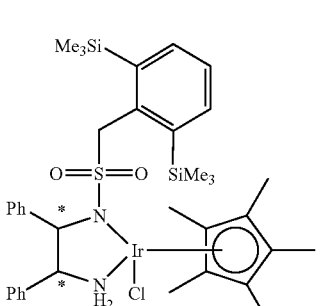
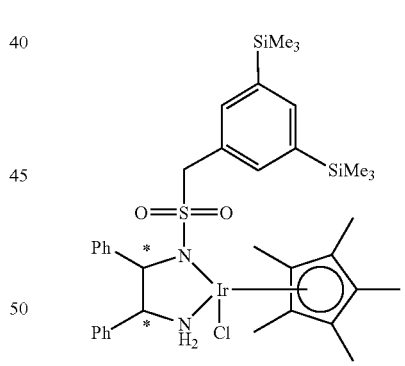
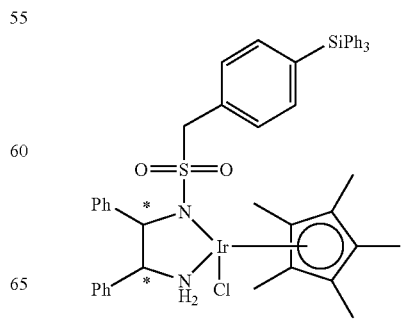

121
-continued
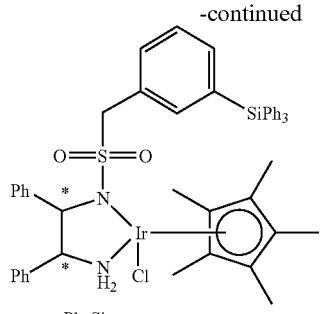
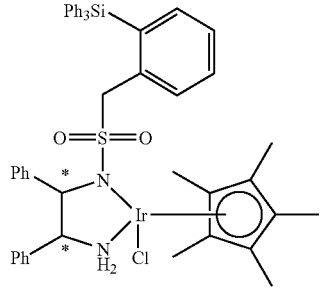
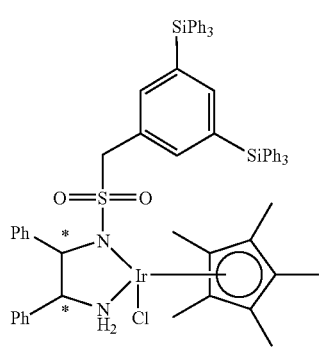
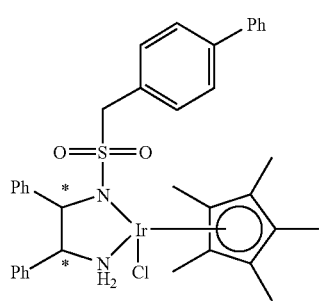
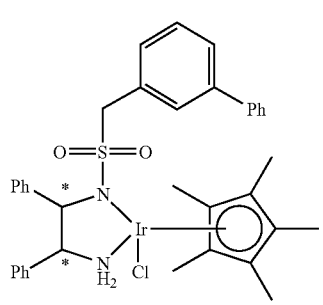
122
-continued
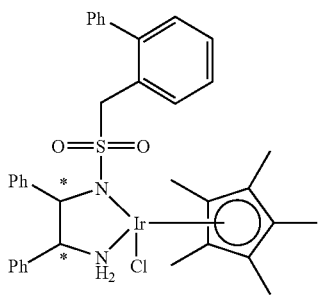
[Chem. 37]
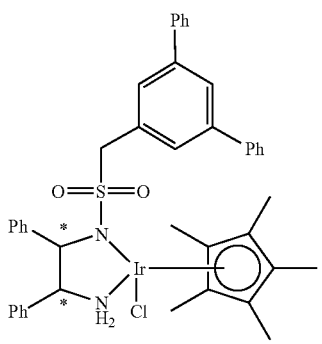
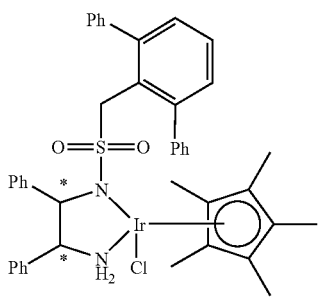
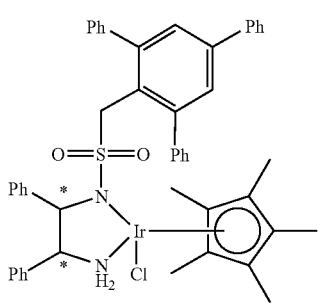
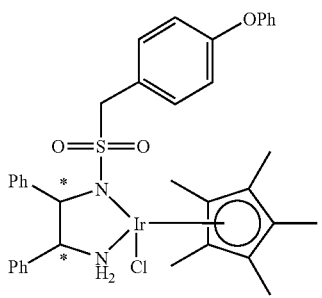

123
-continued
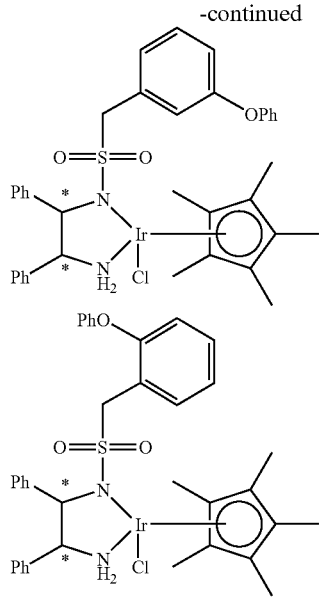
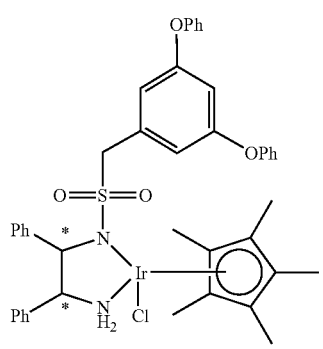
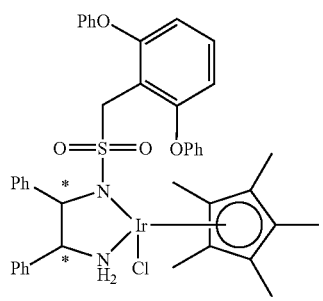
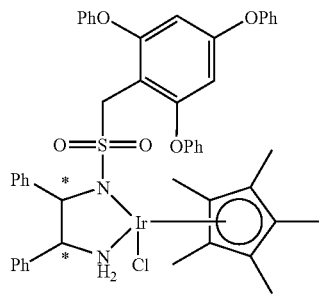
124
-continued
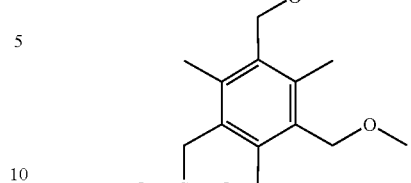
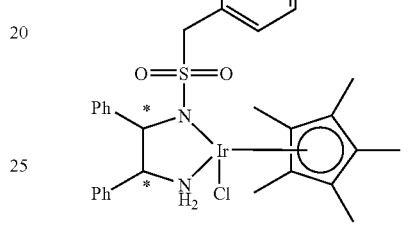
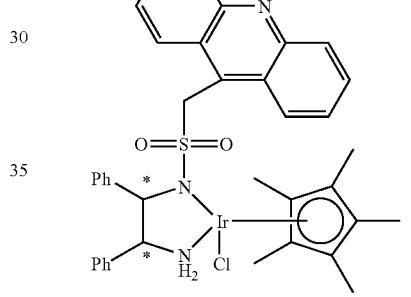
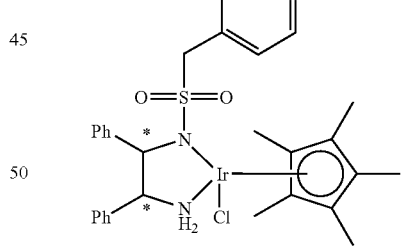
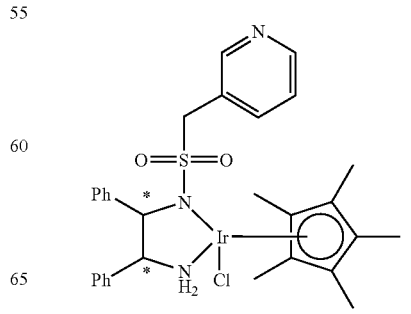

125
-continued
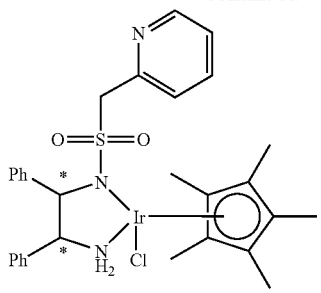
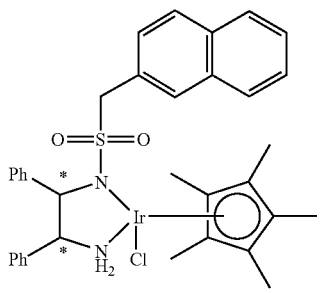
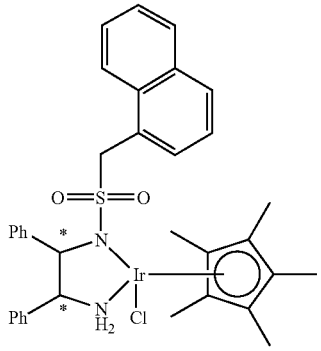
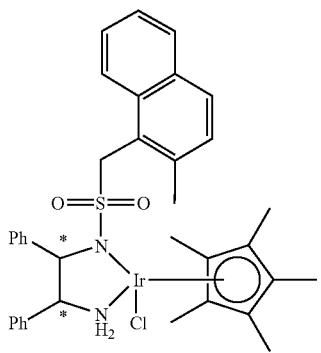
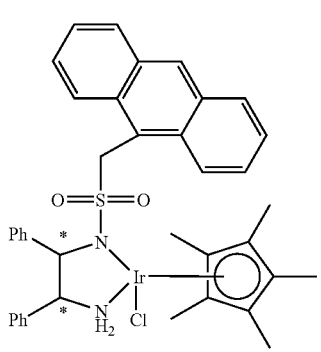
126
-continued
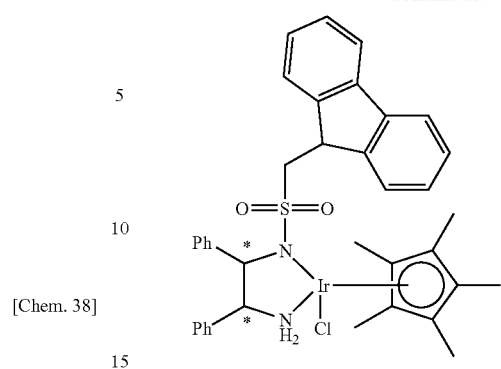
[Chem. 38]
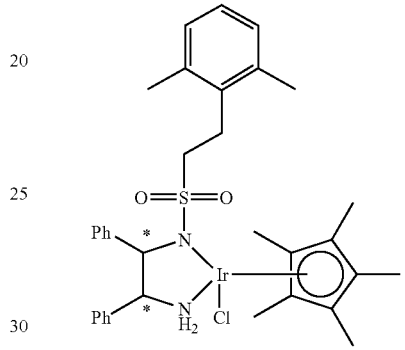
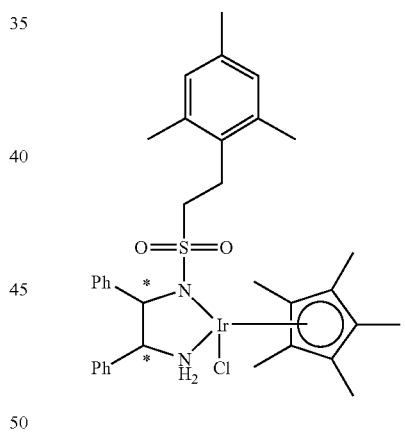
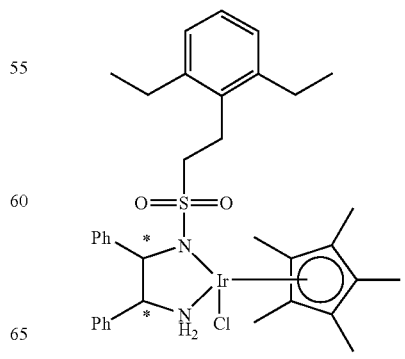

127
-continued
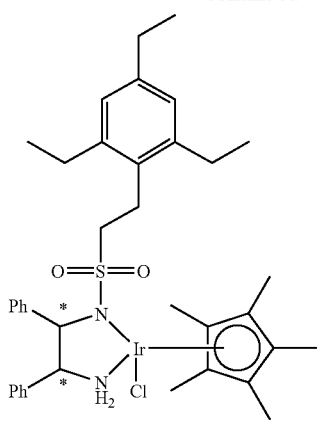
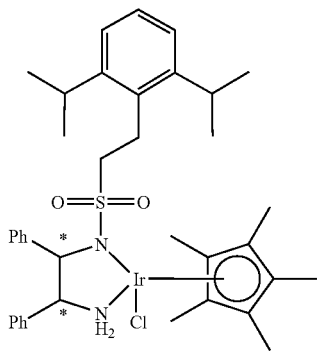
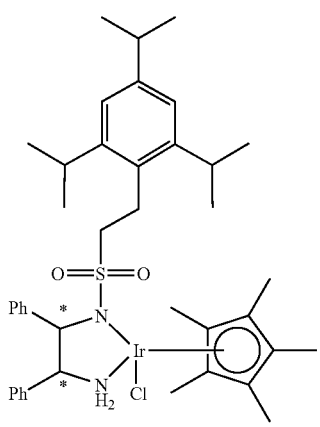
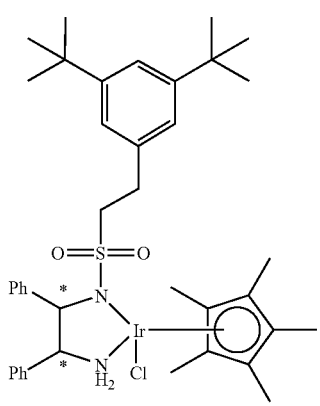
128
-continued
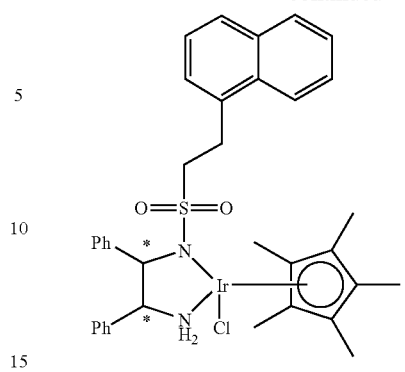
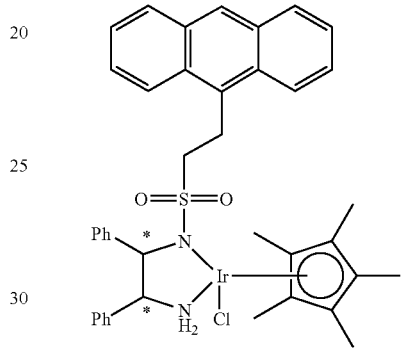
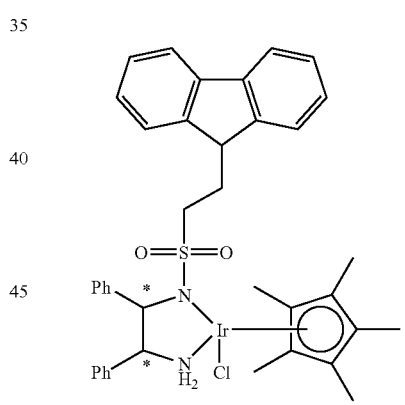
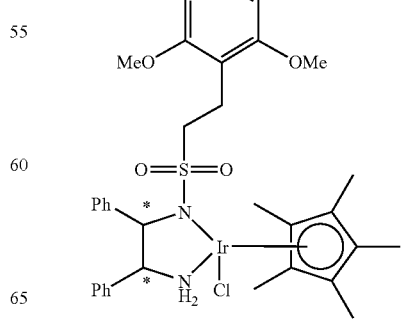

-continued
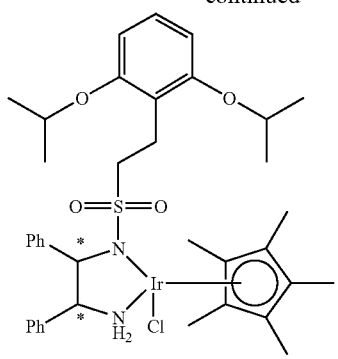
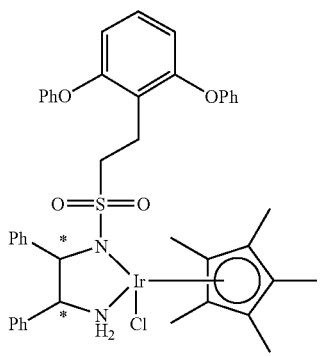
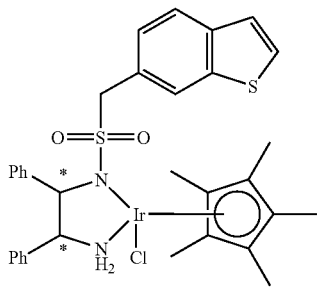
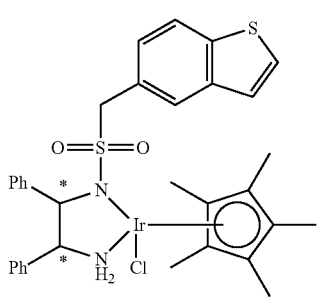
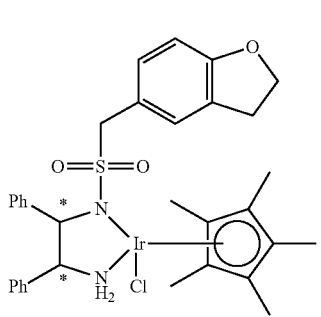
-continued
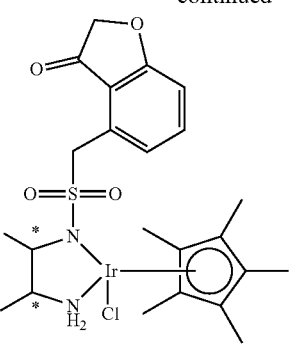
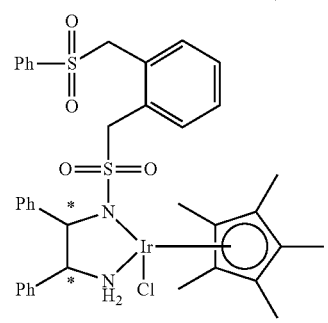
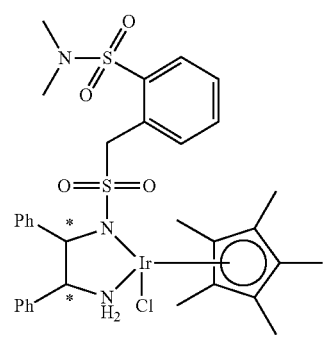
⊘ indicates text missing or illegible when filed
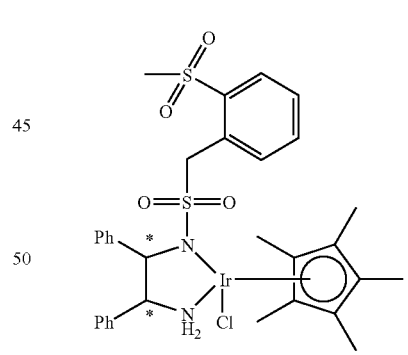
[Chem. 39]
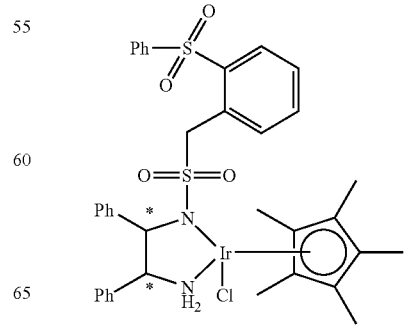

131
-continued
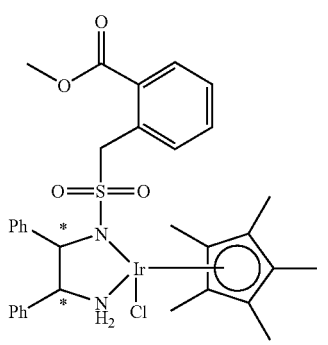
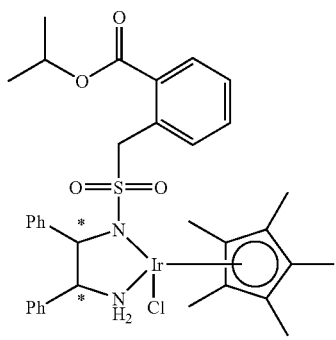
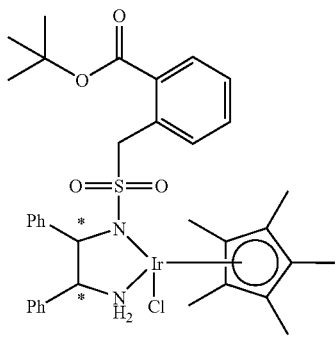
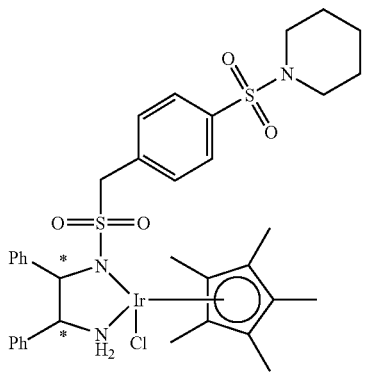
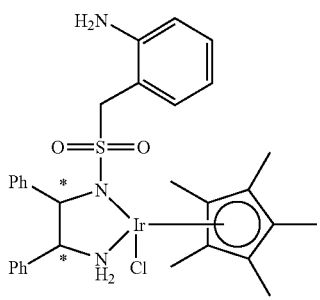
132
-continued
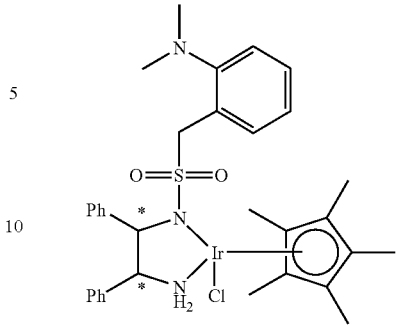
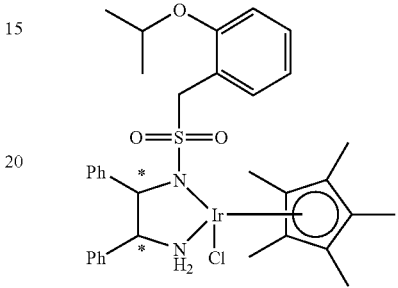
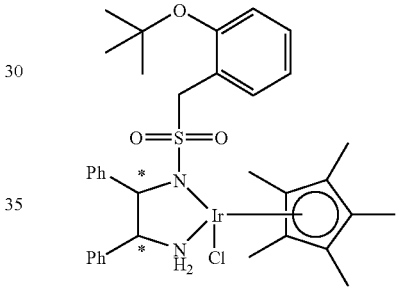
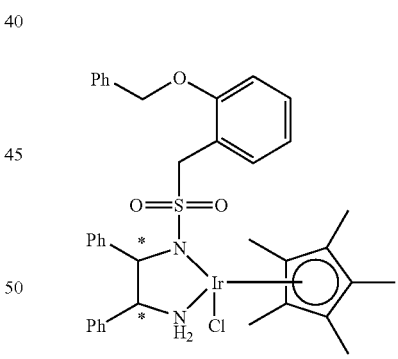
[Chem. 40]
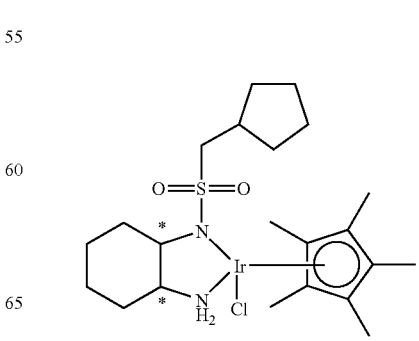

133
-continued
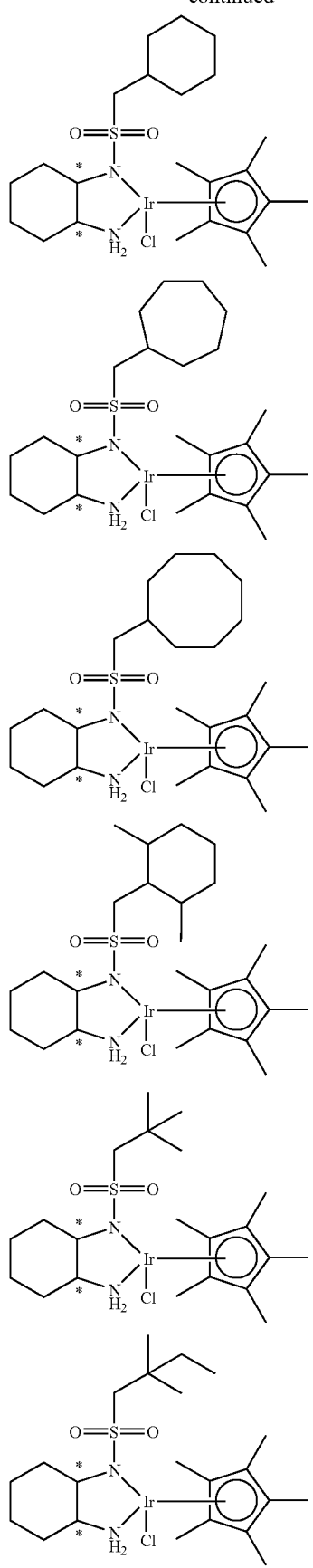
134
-continued
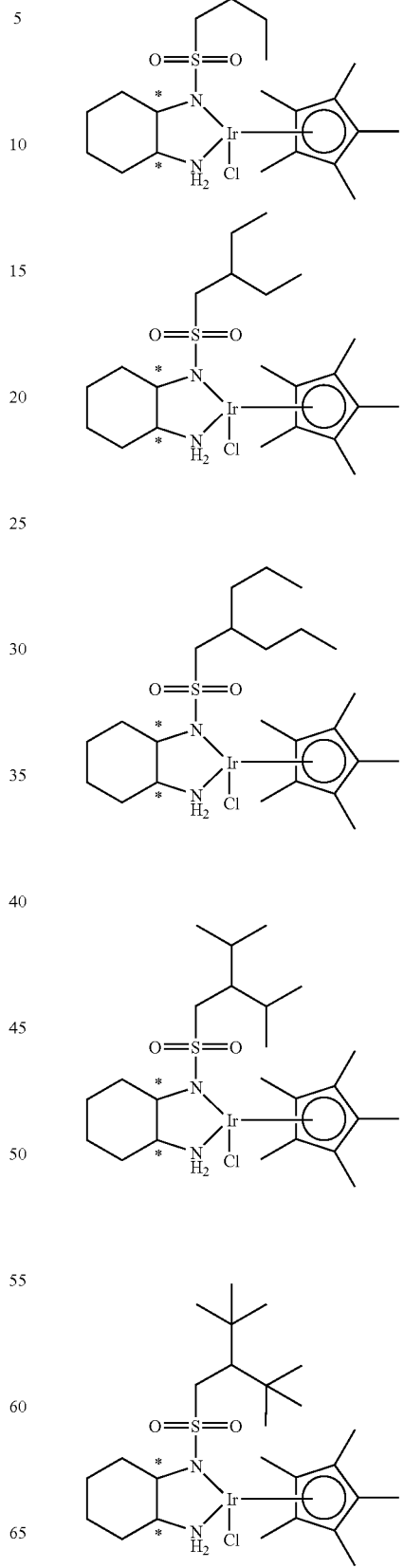

135
-continued
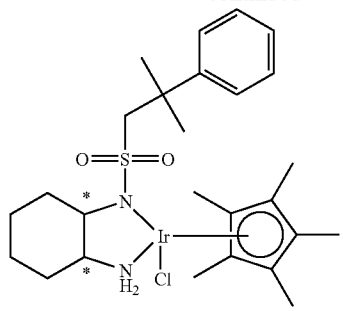
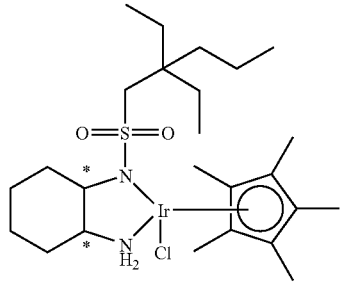
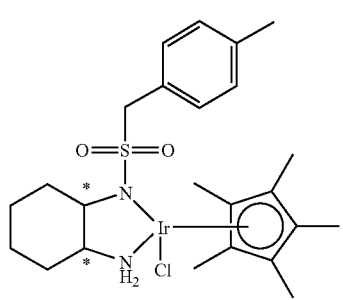
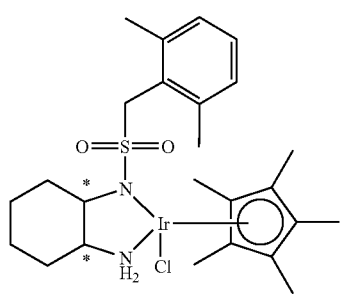
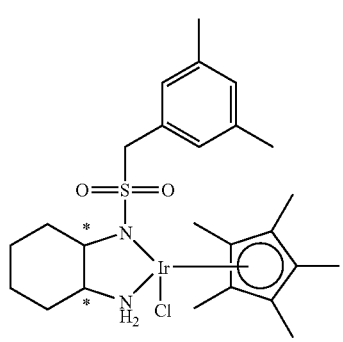
136
-continued
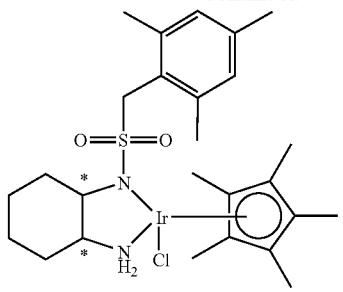
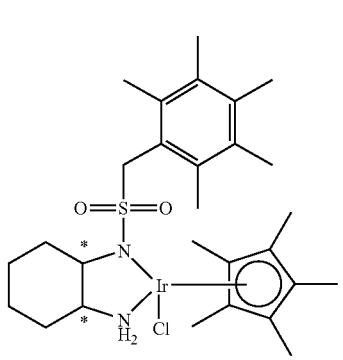
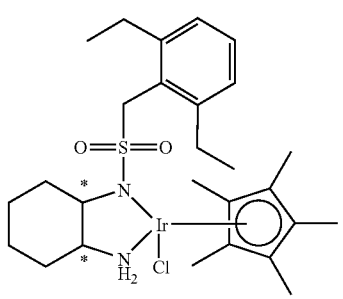
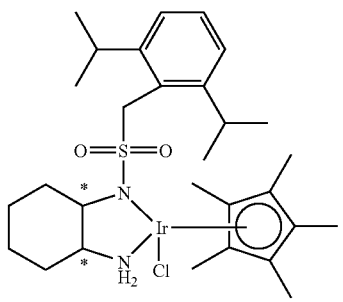
[Chem. 41]
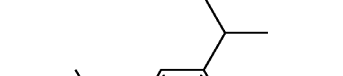
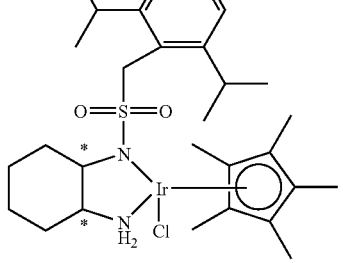

137
-continued
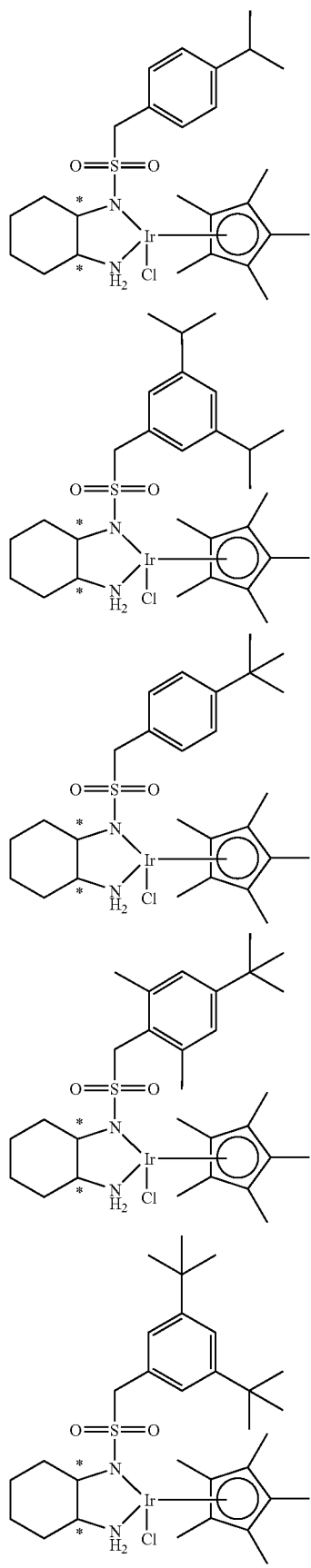
138
-continued
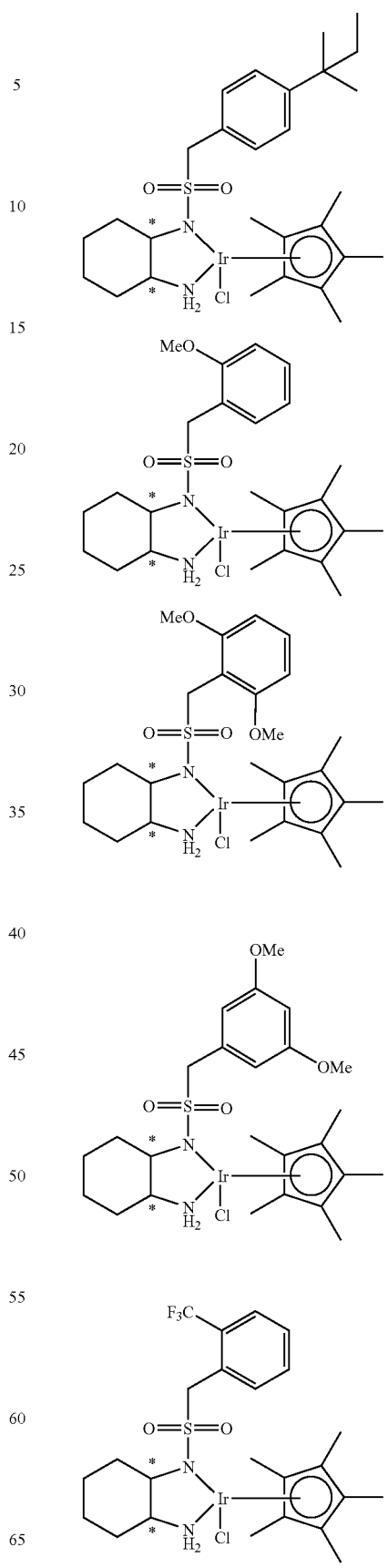

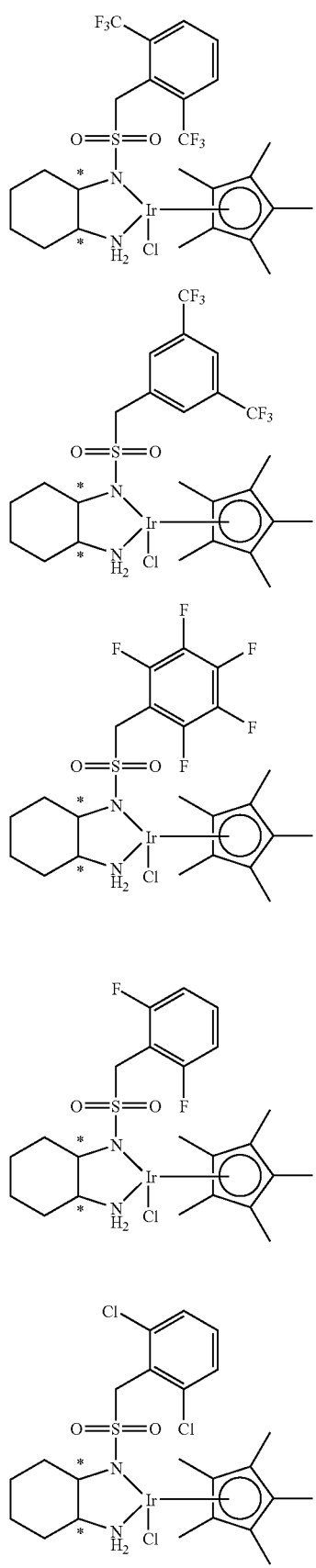
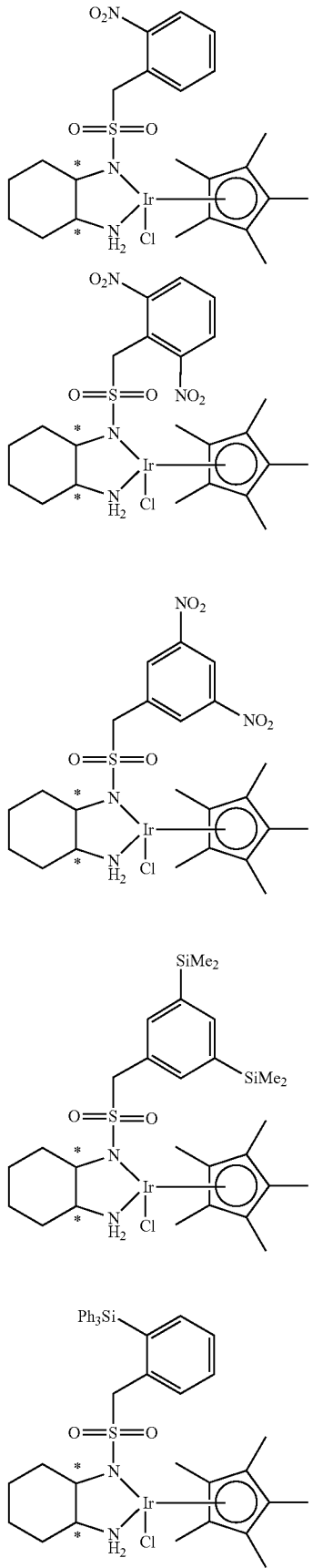
[Chem. 42]

141
-continued
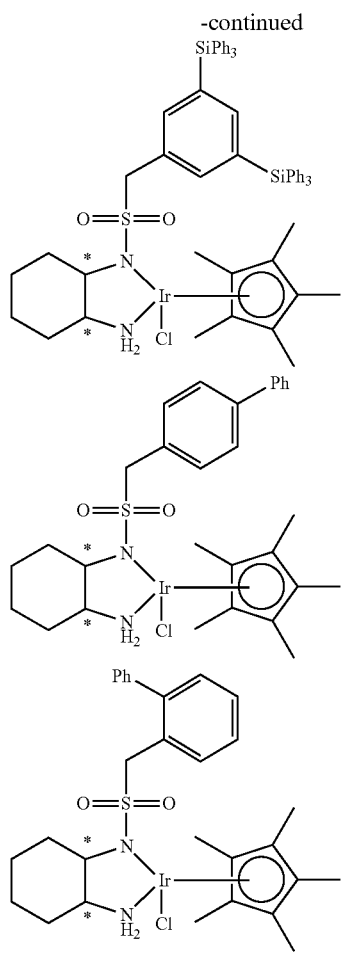
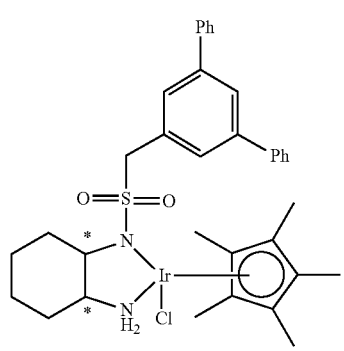
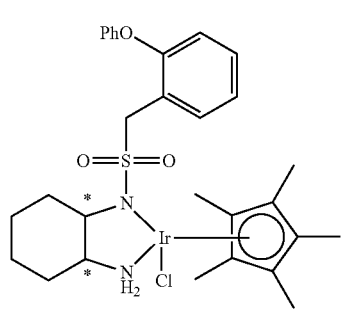
142
-continued
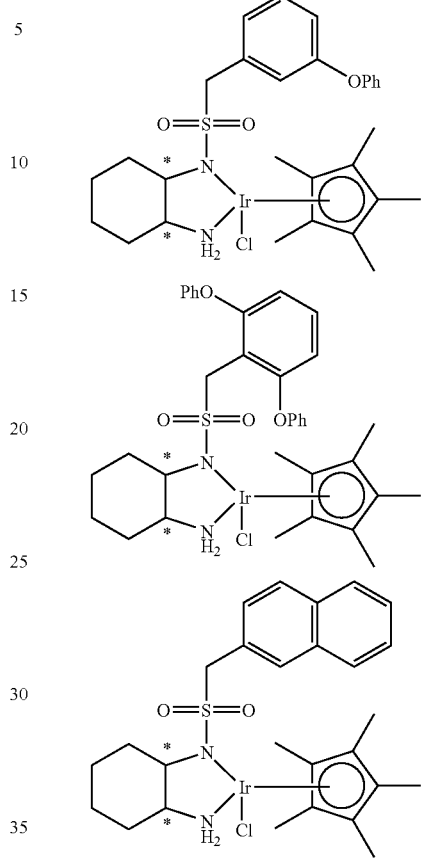
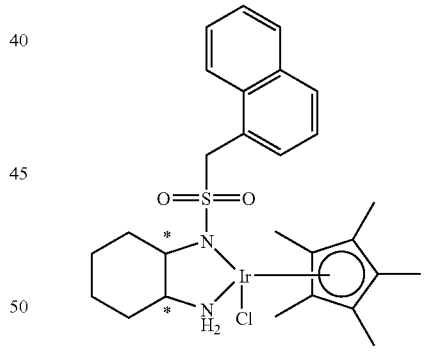
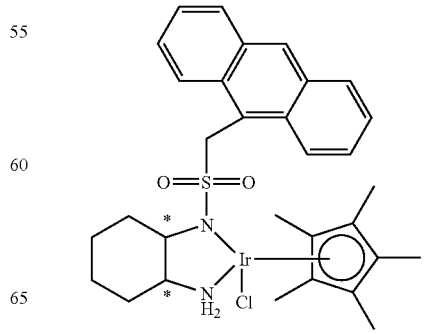

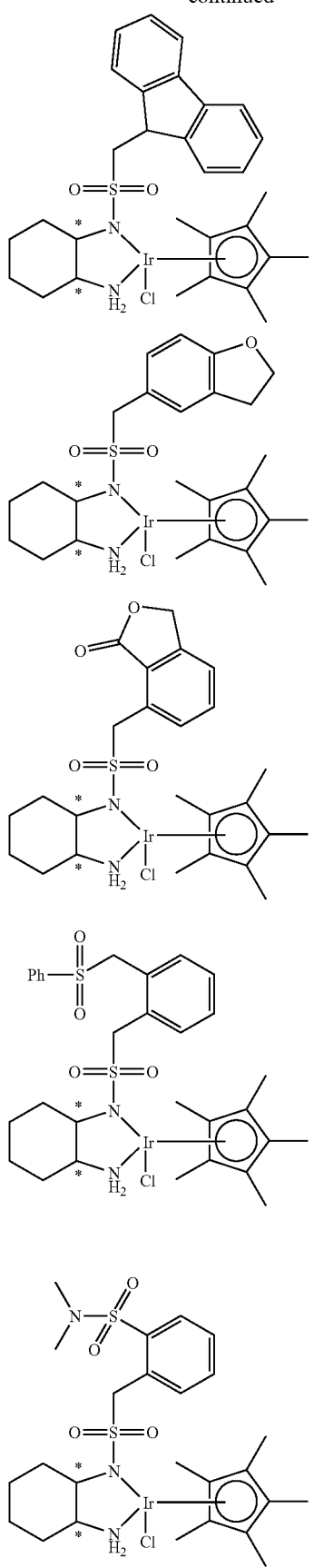
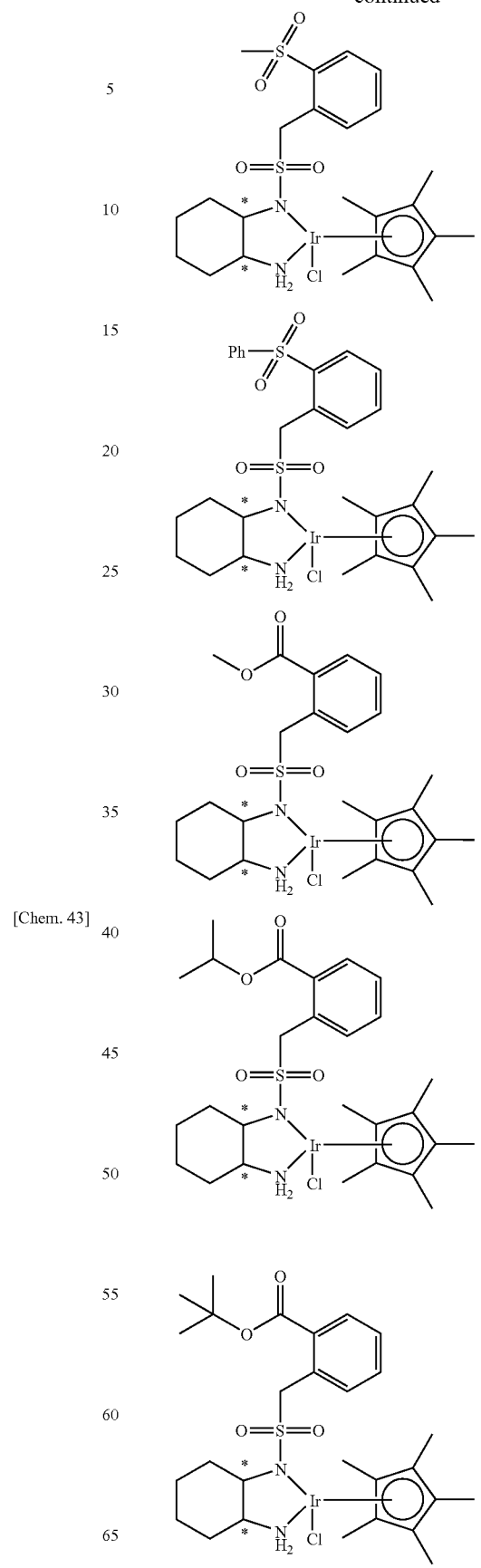

-continued

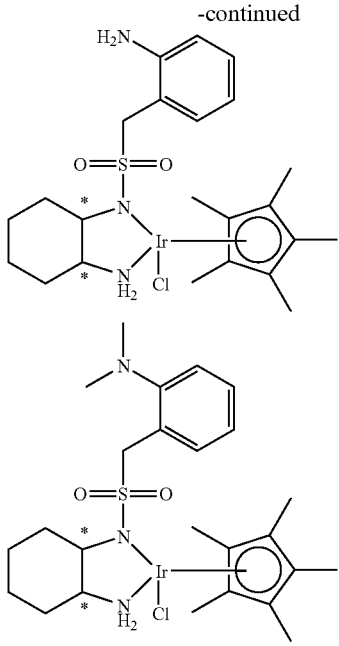

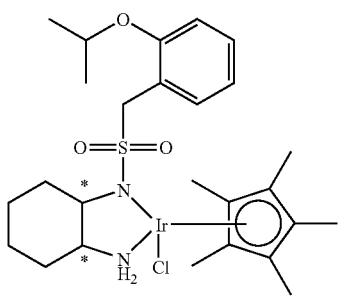

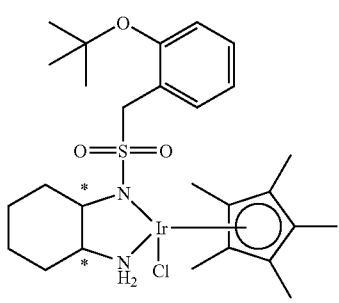

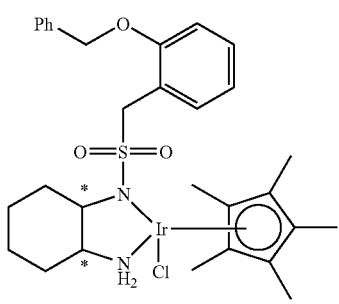

-continued

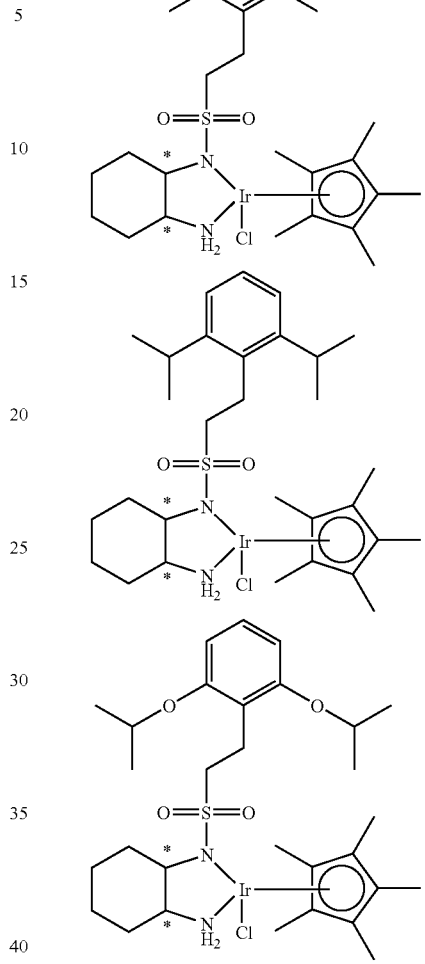

The above exemplary compounds of general formula (1) may be in a state wherein the above solvent molecules or water molecules are bound or coordinated.

Specific examples of the compounds of general formulae (2) and (3) are the same as the above specific examples of the compound of general formula (1). Namely, specific examples of the compounds of general formulae (2) and (3) include ethylenediamine compounds and organic metal compounds, respectively, that constitute each compound of the examples of the compound of general formula (1).

Preferable specific examples of the compound of general formula (1) include, as ruthenium complexes, for example, $RuCl[(S,S)—(C_2H_5)_2CHCH_2SO_2dpen](p\text{-cymene})$, $RuCl[(R,R)—(C_2H_5)_2CHCH_2SO_2dpen](p\text{-cymene})$, $RuCl[(S,S)—(C_2H_5)_2CHCH_2SO_2dpen](mesitylene)$, $RuCl[(R,R)—(C_2H_5)_2CHCH_2SO_2dpen](mesitylene)$, $RuCl[(S,S)\text{-}(n\text{-}C_3H_7)_2CHCH_2SO_2dpen](p\text{-cymene})$, $RuCl[(R,R)\text{-}(n\text{-}C_3H_7)_2CHCH_2SO_2dpen](p\text{-cymene})$, $RuCl[(S,S)\text{-}(n\text{-}C_3H_7)_2CHCH_2SO_2dpen](mesitylene)$, $RuCl[(R,R)\text{-}(n\text{-}C_3H_7)_2CHCH_2SO_2dpen](mesitylene)$, $RuCl[(S,S)\text{-}(c\text{-}C_6H_{11})CH_2SO_2dpen](p\text{-cymene})$, ("c" denotes "cyclo") $RuCl[(R,R)\text{-}(c\text{-}C_6H_{11})CH_2SO_2dpen](p\text{-cymene})$, $RuCl[(S,S)\text{-}(c\text{-}C_6H_{11})CH_2SO_2dpen](mesitylene)$, $RuCl[(R,R)\text{-}(c\text{-}C_6H_{11})CH_2SO_2dpen](mesitylene)$, $RuCl[(S,S)\text{-}2',6'\text{-}Me_2C_6H_3CH_2SO_2dpen](p\text{-cymene})$, $RuCl[(R,R)\text{-}2',6'\text{-}$ Me$_2$C$_6$H$_3$CH$_2$SO$_2$dpen](p-cymene), RuCl[(S,S)-2',6'-Me$_2$C$_6$H$_3$CH$_2$SO$_2$dpen](mesitylene), RuCl[(R,R)-2',6'-Me$_2$C$_6$H$_3$CH$_2$SO$_2$dpen](mesitylene), RuCl[(S,S)-3',5'-Me$_2$C$_6$H$_3$CH$_2$SO$_2$dpen](p-cymene), RuCl[(R,R)-3',5'-Me$_2$C$_6$H$_3$CH$_2$SO$_2$dpen](p-cymene), RuCl[(S,S)-3',5'-Me$_2$C$_6$H$_3$CH$_2$SO$_2$dpen](mesitylene), RuCl[(R,R)-3',5'-Me$_2$C$_6$H$_3$CH$_2$SO$_2$dpen](mesitylene), RuCl[(S,S)-3',5'-(MeO)$_2$C$_6$H$_3$CH$_2$SO$_2$dpen](p-cymene), RuCl[(R,R)-3',5'-(MeO)$_2$C$_6$H$_3$CH$_2$SO$_2$dpen](p-cymene), RuCl[(S,S)-3',5'-(MeO)$_2$C$_5$H$_3$CH$_2$SO$_2$dpen](mesitylene), and RuCl[(R,R)-3',5'-(MeO)$_2$C$_6$H$_3$CH$_2$SO$_2$dpen](mesitylene); as iridium complexes, for example, CP*IrCl[(S,S)—(C$_2$H$_5$)$_2$CHCH$_2$SO$_2$dpen], CP*IrCl[(R,R)—(C$_2$H$_5$)$_2$CHCH$_2$SO$_2$dpen], CP*IrCl[(S,S)-(n-C$_3$H$_7$)$_2$CHCH$_2$SO$_2$dpen], CP*IrCl[(R,R)-(n-C$_3$H$_7$)$_2$CHCH$_2$SO$_2$dpen], CP*IrCl[(S,S)-(c-C$_6$H$_{11}$)CH$_2$SO$_2$dpen], CP*IrCl[(R,R)-(c-C$_6$H$_{11}$)CH$_2$SO$_2$dpen], CP*IrCl[(S,S)-2',6'-Me$_2$C$_6$H$_3$CH$_2$SO$_2$dpen], CP*IrCl[(R,R)-2',6'-Me$_2$C$_6$H$_3$CH$_2$SO$_2$dpen], CP*IrCl[(S,S)-3',5'-Me$_2$C$_6$H$_3$CH$_2$SO$_2$dpen], CP*IrCl[(R,R)-3',5'-Me$_2$C$_6$H$_3$CH$_2$SO$_2$dpen], CP*IrCl[(S,S)-3',5'-(MeO)$_2$C$_6$H$_3$CH$_2$SO$_2$dpen], and CP*IrCl[(R,R)-3',5'-(MeO)$_2$C$_6$H$_3$CH$_2$SO$_2$dpen].

Specific preferable examples of the compound of general formula (2) include, for example, (S,S)—(C$_2$H$_5$)$_2$CHCH$_2$SO$_2$DPEN, (R,R)—(C$_2$H$_5$)$_2$CHCH$_2$SO$_2$DPEN, (S,S)-(n-C$_3$H$_7$)$_2$CHCH$_2$SO$_2$DPEN, (R,R)-(n-C$_3$H$_7$)$_2$CHCH$_2$SO$_2$DPEN, (S,S)-(c-C$_6$H$_{11}$)CH$_2$SO$_2$DPEN, ("c" denotes "cyclo"), (R,R)-(c-C$_6$H$_{11}$)CH$_2$SO$_2$DPEN, (S,S)-2',6'-Me$_2$C$_6$H$_3$CH$_2$SO$_2$DPEN, (R,R)-2',6'-Me$_2$C$_6$H$_3$CH$_2$SO$_2$DPEN, (S,S)-3',5'-Me$_2$C$_6$H$_3$CH$_2$SO$_2$DPEN, (R,R)-3',5'-Me$_2$C$_6$H$_3$CH$_2$SO$_2$DPEN, (S,S)-3',5'-(MeO)$_2$C$_6$H$_3$CH$_2$SO$_2$DPEN, (R,R)-3',5'-(MeO)$_2$C$_6$H$_3$CH$_2$SO$_2$DPEN.

Compounds of general formula (1) can be obtained by a preparation process described in, for example, Angew. Chem. Ind. Ed. Engl, Vol. 36, p. 285 (1997), but the process is not limited thereto.

With the process for preparing optically-active alcohols of the present invention, the alcohols are prepared by reacting a ketone substrate and a hydrogen donor under the presence of a catalyst comprising a ruthenium, iridium or rhodium complex of general formula (1), or that comprising a compound of general formula (2) and an organic metal compound of general formula (3). Since the catalyst comprising a compound of general formula (2) and an organic metal compound of general formula (3) has almost similar performance as the compound of general formula (1), it is considered that during the process of asymmetric reduction of ketones, an organic compound of general formula (2) reacts with an organic metal compound of general formula (3) in the system to produce at least partially, a corresponding organic metal compound of general formula (1). The compound of general formula (2) is not only useful as a precursor of the organic metal compound of general formula (1), but also effectively constructs a superior catalyst by being combined with the organic metal compound of general formula (3); thus it is extremely useful. In addition, among the compounds of general formula (1), even an amide complex which is a compound of general formula (1) wherein n=0 and X is absent can be used similar to an amine complex wherein n=1 and X is present.

As hydrogen donors used in the process of preparing optically-active alcohols, the following substances can be used alone, or a combination of a plurality of these substances can be used: hydrogen gas, formic acid/dimethylamine mixture, formic acid/trimethylamine mixture, formic acid/diethylamine mixture, formic acid/triethylamine mixture, methanol, ethanol, 1-propanol, 2-propanol, 1-butanol, sec-butyl alcohol, n-pentyl alcohol, cyclopentyl alcohol, n-hexyl alcohol, cyclohexyl alcohol, benzyl alcohol, HCOOK, HCOONa, HCOOLi, and HCOONH$_4$.

When hydrogen gas is used as a hydrogen donor, it is preferable to use the compound of general formula (1) as a catalyst, more preferably, the use of a compound wherein X in general formula (1) is a sulfonate group, and furthermore preferably, the use of a compound wherein X is a trifluoromethane sulfonate group. When hydrogen-transfer reduction is carried out using a mixture of formic acid and organic amine as a hydrogen donor, both the compound of general formula (1), and the catalyst comprising the compound of general formula (2) and the compound of general formula (3) can be suitably used as the catalyst. In addition, when hydrogen-transfer reduction is carried out using a formate as a hydrogen donor, both the compound of general formula (1), and the catalyst comprising the compound of general formula (2) and the compound of general formula (3) can be suitably used as the catalyst.

When hydrogen gas is used as a hydrogen donor, for example, a catalyst, a ketone compound and a solvent are mixed and stirred under a hydrogen-gas pressure. As the solvent, alcohol solvents such as methanol, ethanol, 1-propanol, 2-propanol, 1-butanol, sec-butyl alcohol, 2-methyl-2-propanol, n-pentyl alcohol, 2-methyl-2-butanol, cyclopentyl alcohol, n-hexyl alcohol, cyclohexyl alcohol, and benzyl alcohol may be suitably used, and particularly preferably methanol, ethanol or 2-propanol may be used. In addition, when a ketone substrate is solid, with the aim of promoting mixture of a ketone substrate and a catalyst, if necessary, ether solvents such as tetrahydrofuran (THF), diethyl ether, tert-butyl methyl ether (TBME), cyclopentylmethyl ether (CPME), etc., and heteroatom-containing solvents such as DMSO, DMF, acetonitrile, etc., aromatic hydrocarbon solvents such as benzene, toluene, xylene, etc., halogen-containing hydrocarbon solvents such as methylene chloride, etc., and ester solvents such as ethyl acetate, etc. may be used alone, or a combination of two or more of these may be used.

The pressure of hydrogen gas is not particularly limited; in general higher hydrogen pressure is preferable because this may possibly improve catalytic activity. From a practical standpoint, reaction is preferably carried out by adjusting the hydrogen pressure between 5-100 atm.

Reaction temperature is preferably between 0-70° C., and more preferably between 20-60° C. Reaction time varies depending on the reaction conditions such as kind of substrate, S/C (substrate/catalyst molar ratio), temperature, and hydrogen gas pressure, as well as kind of catalyst; therefore, these conditions may be set such that reaction is completed within 0.5 hr to several days. From a practical standpoint, these conditions may be set such that reaction is completed within 1-24 hr.

When a mixture of formic acid and organic amine is used as a hydrogen donor, for example, a hydrogen donor, a catalyst and a ketone compound are mixed and stirred. When a ketone substrate dissolves in a mixture of formic acid and organic amine, usually it is not necessary to add a solvent; however, with the aim of facilitating mixture of a ketone substrate and a catalyst, if necessary, a solvent may be added. As the solvent added, alcohol solvents such as methanol, ethanol, 1-propanol, 2-propanol, 1-butanol, sec-butyl alcohol, 2-methyl-2-propanol, n-pentyl alcohol, 2-methyl-2-butanol, cyclopentyl alcohol, n-hexyl alcohol, cyclohexyl alcohol, and benzyl alcohol, etc., ether solvents such as tetrahydrofuran (THF), diethyl ether, tert-butyl methyl ether (TBME), cyclopentyl methyl ether (CPME), etc., heteroatom-containing solvents such as DMSO, DMF, acetonitrile, etc., aromatic hydrocarbon solvents such as benzene, toluene, xylene, etc., and halogen-containing hydrocarbon solvents such as methylene chloride, etc. may be used alone, or a combination of two or more of these may be used.

The organic amine used by being mixed with formic acid is not particularly limited and various organic amines may be used. Triethylamine may be preferably used. The mixture molar ratio of organic amine to formic acid is preferably at formic acid:organic amine=approximately from 10:1 to 1:1, and more preferably at formic acid:organic amine=approximately from 2:1 to 1:1. The amount of a hydrogen donor in general is preferably from 1.5- to 5-fold moles relative to the substrate.

When a catalyst comprising a compound of general formula (2) and a compound of general formula (3) is used, in order to prepare a catalytic active species or a precursor of an active species in a system of reduction process, a slight amount of a base may be added. As the base, any of inorganic compounds and organic compounds may be used; sodium hydroxide, potassium hydroxide, potassium tert-butoxide, potassium carbonate, sodium carbonate, triethylamine, etc. may be suitably used. The amount of abase added is preferably 2-5 equivalents based on the compound of general formula (2). It is also preferable that the molar ratio of the compound of general formula (2) to the compound of general formula (3) is 2:1.

The reaction temperature is preferably in the range of 0-70° C. and more preferably in the range of 20-60° C. Since the reaction time varies depending on the reaction conditions such as kind of substrate, S/C, temperature, and equivalent value of hydrogen donor, as well as kind of catalyst; therefore, these conditions may be set such that reaction is completed within 0.5 hr to several days. From a practical standpoint, these conditions may be set such that reaction is completed within 1-24 hr.

When a formate is used as a hydrogen donor, for example, a hydrogen donor, a catalyst, a ketone compound and water are mixed and stirred. When a ketone substrate is liquid at the reaction temperature, usually it is not necessary to add a solvent. However, when a substrate is solid, with the aim of facilitating mixture of a ketone substrate and a catalyst, if necessary, a solvent may be added. As the solvent added, alcohol solvents such as methanol, ethanol, 2-propanol, 2-methyl-2-propanol, 2-methyl-2-butanol, etc., ether solvents such as tetrahydrofuran (THF), diethyl ether, tert-butyl methyl ether (TBME), cyclopentyl methyl ether (CPME), etc., heteroatom-containing solvents such as DMSO, DMF, acetonitrile, etc., aromatic hydrocarbon solvents such as benzene, toluene, xylene, etc., and halogen-containing hydrocarbon solvents such as methylene chloride, etc., ester solvents such as ethyl acetate, butyl acetate, etc. may be used alone, or a combination of two or more of these may be used.

The formate used as a hydrogen donor is a salt of a formic acid with an alkaline metal or an alkaline earth metal, and its specific examples include lithium formate, sodium formate, potassium formate, ammonium formate, cesium formate, magnesium formate, calcium formate, etc. Preferable examples include sodium formate or potassium formate. The concentration of a formate is suitably selected based on factors such as balance between an amount of ketone substrate reacted and a size of reaction apparatus, etc. The amount of water added is preferable 1.5-10 molar equivalents relative to the ketone substrate; because the rate of reduction reaction generally increases as the formate concentration increases, an amount that allows a saturated aqueous formate solution is preferred, provided that this amount does not affect inversely to the entire process. The amount of a hydrogen donor may be excess molar volumes relative to the substrate; in general it is preferably from 1.1- to 5-fold moles relative to the substrate.

When a catalyst comprising a compound of general formula (2) and a compound of general formula (3) is used, in order to prepare a catalytic active species or a precursor of an active species in a system of reduction process, a slight amount of a base may be added. As the base, any of inorganic compounds and organic compounds may be used; sodium hydroxide, potassium hydroxide, potassium tert-butoxide, potassium carbonate, sodium carbonate, triethylamine, etc. may be suitably used. The amount of abase added is preferably 2-5 equivalents based on the compound of general formula (2). It is also preferable that the molar ratio of the compound of general formula (2) to the compound of general formula (3) is 2:1.

The reaction temperature is preferably in the range of 0-70° C., and more preferably in the range of 20-60° C. Since the reaction time varies depending on the reaction conditions such as kind of substrate, S/C, temperature, and equivalent value of hydrogen donor, presence/absence of solvent, etc., as well as kind of catalyst; therefore, these conditions may be set such that reaction is completed within 0.5 hr to several days. From a practical standpoint, these conditions may be set such that reaction is completed within 1-24 hr.

The amount of a catalyst used may be expressed by a molar ratio of a ketone substrate to a ruthenium, iridium or rhodium catalyst as S/C (S denotes substrate and C denotes catalyst). In this case, the highest extent of S/C significantly varies depending on the structure of ketone substrate, kind of catalyst, and kind of hydrogen donor; from a practical standpoint, preferably, the S/C for the case of hydrogen gas as a hydrogen donor is set at around 3000-500,000, that for the case of mixture of formic acid and organic amine is set at around 300-5,000, and that for the case of formate is set at around 1,000-10,000.

When a formate is used as a hydrogen donor, the reaction may be carried out by adding a phase-transfer catalyst if necessary. By the addition of a phase-transfer catalyst, in many cases an increase in the rate of reduction reaction is observed. Examples of the phase-transfer catalyst used include tetrabutylammonium fluoride, tetrabutylammonium chloride, tetrabutylammonium bromide, tetrabutylammonium iodide, tetrabutylammonium hydroxide, tetramethylammonium fluoride, tetramethylammonium chloride, tetramethylammonium bromide, tetramethylammonium iodide, tetramethylammonium hydroxide, benzyltrimethylammonium fluoride, benzyltrimethylammonium chloride, benzyltrimethylammonium bromide, benzyltrimethylammonium iodide, benzyltrimethylammonium hydroxide, tetraethylammonium fluoride, tetraethylammonium chloride, tetraethylammonium bromide, tetraethylammonium iodide, tetraethylammonium hydroxide, tetrapropylammonium fluoride, tetrapropylammonium chloride, tetrapropylammonium bromide, tetrapropylammonium iodide, tetrapropylammonium hydroxide, hexadecyltrimethylammonium fluoride, hexadecyltrimethylammonium chloride, hexadecyltrimethylammonium bromide, hexadecyltrimethylammonium iodide, hexadecyltrimethylammonium hydroxide, phenyltrimethylammonium fluoride, phenyltrimethylammonium chloride, phenyltrimethylammonium bromide, phenyltrimethylammonium iodide, phenyltrimethylammonium hydroxide, dodecyltrimethylammonium fluoride, dodecyltrimethylammonium chloride, dodecyltrimethylammonium bromide, dodecyltrimethylammonium iodide, dodecyltrimethylammonium hydroxide, benzyltriethylammonium fluoride, benzyltriethylammonium chloride, benzyltriethylammonium bromide, benzyltriethylammonium iodide, benzyltriethylammonium hydroxide, etc.

The amount of a phase-transfer catalyst added is usually between 0.001-10 molar equivalents relative to the amount of ketone substrate, and preferably between 0.01-0.1 molar equivalents. Purification of reaction products is carried out by publicly known methods such as column chromatography, distillation and re-crystallization, etc., or a suitable combination thereof.

In the preparation process of alcohols of the present invention, addition of acid or base to a reaction system is not necessary; hydrogenation or reduction of ketone compounds rapidly progresses without addition of acid and base. However, this does not exclude the addition of acid or base; for example, depending on the structure of reaction substrates and purity of reagents used, a small amount of acid and base may be appropriately added, thereby possibly improving the rate of reduction reaction and enantioselectivity.

In the compound of general formula (1) or (2) of the invention, two chiral carbons must be either both (R) forms or both (S) forms in order to obtain optically-active alcohols. By selecting either (R) form or (S) form, optically-active alcohols with a desired absolute configuration can be obtained. Here, when racemic alcohols or achiral alcohols are to be prepared, these two chiral carbons are not necessarily both (R) forms or both (S) forms, and they may be any form independently of one another.

Using the catalyst of the present invention, it is possible to prepare an optically-active alcohol from an aromatic ketone having a substituent at 2' position of the benzene ring at a high yield and high enantioselectivity, to prepare an optically-active alcohol from an aromatic ketone having a plurality of substituents in the benzene ring at a high yield and high enantioselectivity, to prepare an optically-active alcohol having a halogen from a ketone having a halogen at α-position or β-position, and to prepare an optically-active diol from a ketone having a hydroxyl group at α-position or β-position. In particular, by using the catalyst of the invention, 3',5'-bis(trifluoromethyl)acetophenone which is important as a medicinal intermediate, etc. can be converted to a corresponding optically-active alcohol at a high yield and high enantioselectivity. Even in cases of substrates with which optically-active alcohols cannot be obtained at high yield and high enantioselectivity by conventional catalyst systems, for the first time many optically-active alcohols can be efficiently obtained by the inventive catalyst; thus, the method of the present invention is extremely useful. Hereinafter, representative examples of ketone compounds that can be applied to the preparation process of optically-active alcohols of the present invention are listed; however, the present invention is not limited to these ketone compounds.

[Chem. 44]

(c-1)

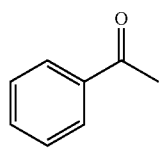

(c-2)

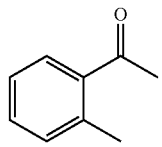

(c-3)

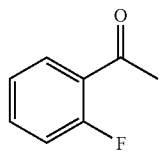

(c-4)

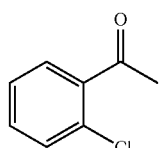

(c-5)

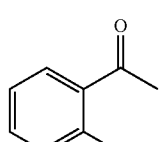

(c-6)

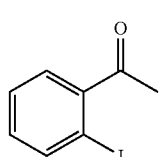

(c-7)

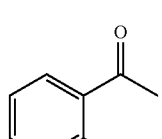

(c-8)

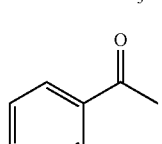

(c-9)

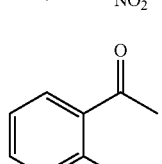

(c-10)

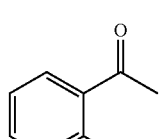

(c-11)

-continued
(c-12) 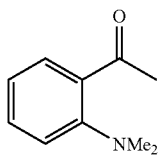
(c-13) 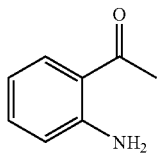
(c-14) 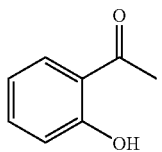
(c-15) 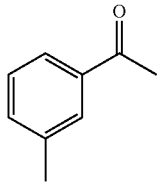
(c-16) 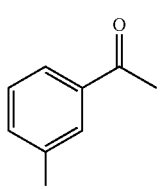
(c-17) 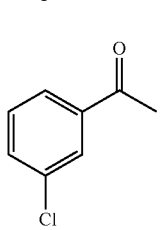
(c-18) 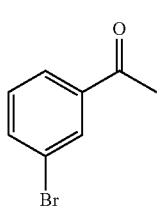
(c-19) 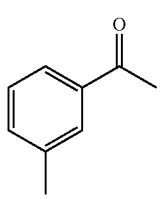
-continued
(c-20) 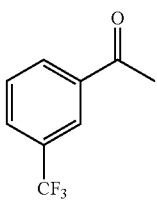
(c-21) 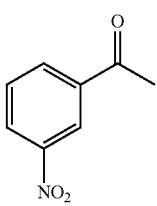
(c-22) 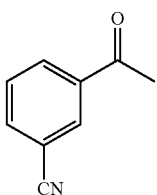
(c-23) 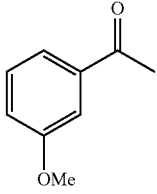
(c-24) 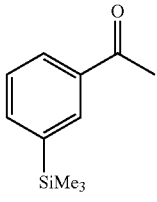
(c-25) 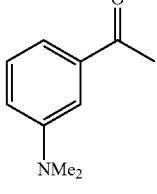
(c-26) 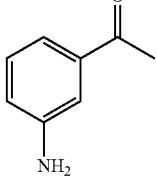
(c-27) 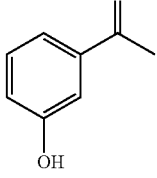

[Chem. 45]
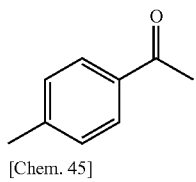 (c-28)
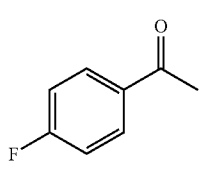 (c-29)
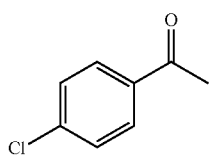 (c-30)
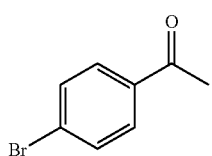 (c-31)
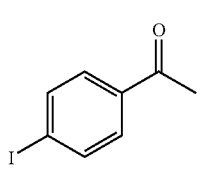 (c-32)
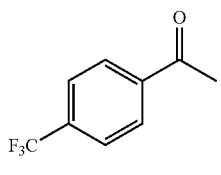 (c-33)
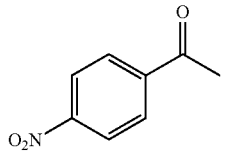 (c-34)
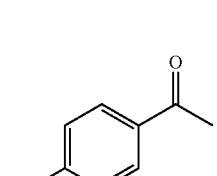 (c-35)
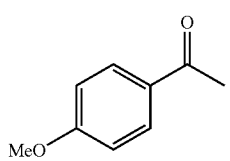 (c-36)
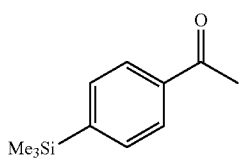 (c-37)
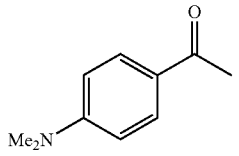 (c-38)
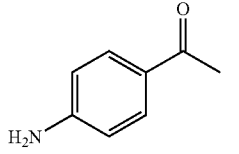 (c-39)
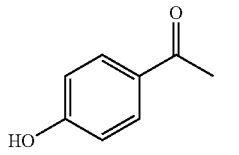 (c-40)
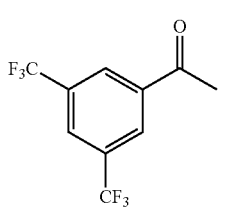 (c-41)
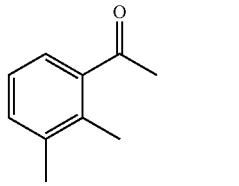 (c-42)
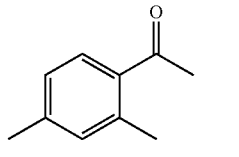 (c-43)
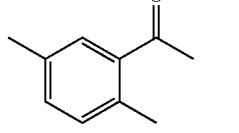 (c-44)
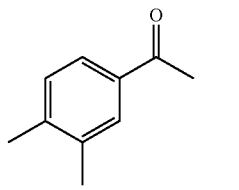 (c-45)

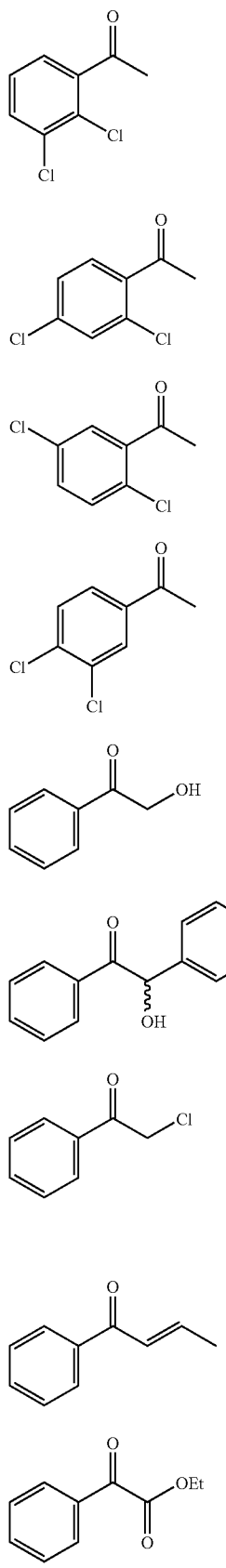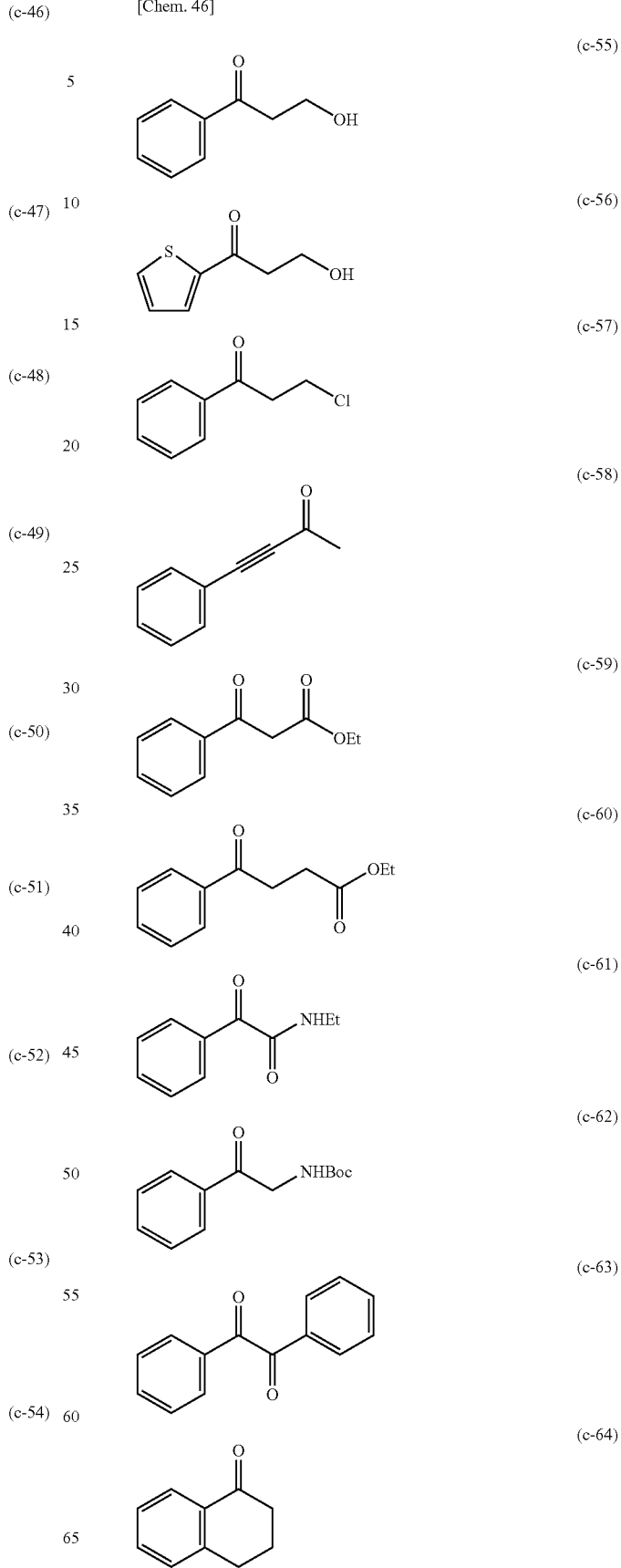

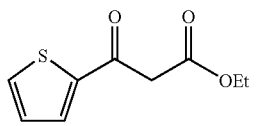
(c-65)

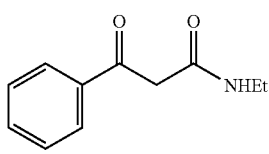
(c-66)

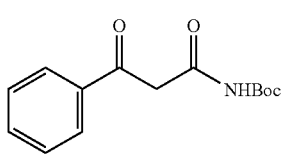
(c-67)

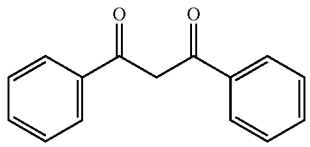
(c-68)

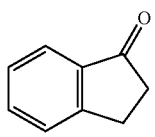
(c-69)

EXAMPLES

Hereinafter, the present invention is explained in more detail using examples and comparative examples; however, the present invention is not limited to these examples. Reactions described in each of the examples and comparative examples below were carried out under an inert-gas atmosphere of argon or nitrogen gas, etc. Water used in the reactions was that after treatment by ion-exchange resin. Ketone substrates described in Tables 1, 2 and 3 were commercially available reagents as they were. A nuclear magnetic resonance (NMR) apparatus was used for identification of ligand complexes and reaction products, with tetramethylsilane (TMS) as an internal standard substance and its signal as δ=0 (δ represents chemical shift). Conversion rates from ketone substrates to alcohol compounds and enantioselectivities were determined by analysis by gas chromatography (GC) using CHIRASIL DEX CB (Chrompack GC column; 0.25 mm×25 m, DF=0.25 μm). JNM-ECX-400P (JEOL Ltd.) was used as an NMR apparatus, and GC-17A (Shimadzu Corporation) was used as a GC apparatus.

[Synthesis of Ligand, Asymmetric Ruthenium Complex and Asymmetric Iridium Complex]

Example 1

Synthesis of (S,S)-(2'-nitrophenyl)methane-SO₂DPEN 2.25 g (10.61 mmol) of (S,S)-DPEN (MW: 212.3) was introduced into a 200-mL three-necked flask and subjected to argon-gas replacement. 100 mL of dehydrated methylene chloride and 1.55 mL (1.14 mmol) of triethylamine were added and cooled to 0° C. To this solution, a solution consisting of 2.50 g (10.61 mmol) of 2-nitro-α-toluenesulfonyl chloride (MW: 235.65) and 25 mL of dehydrated methylene chloride was slowly added dropwise, and stirred at 0° C. for one night. This solution was washed twice with water, the solvent in the organic layer was distilled away, and dried under reduced pressure to give 4.63 g of a crude product. The crude product was purified by silica-gel column chromatography (silica gel 60N, n-hexane:AcOEt=1:1, then AcOEt 100%) to give 1.88 g of (S,S)-(2-nitrophenyl)methane-SO₂DPEN (43% yield).

¹H NMR (400 MHz, CDCl₃, rt, δ/ppm): 4.13 (d, J=13.7 Hz, 1H, CH₂C₆H₄NO₂), 4.19 (d, J=13.7 Hz, 1H, CH₂C₆H₄NO₂), 4.33 (d, J=6.0 Hz, 1H, CHNH₂), 4.62 (d, J=6.0 Hz, 1H, CHNHSO₂), 6.98-7.04 (m, 1H, aromatic proton), 7.15-7.38 (m, 10H, aromatic proton), 7.38-7.50 (m, 2H, aromatic proton), 7.87-7.95 (m, 1H, aromatic proton).

Example 2

Synthesis of Ru(H₂O)(OTf)[(S,S)-(2'-nitrophenyl)methane-SO₂DPEN](p-cymene)

200 mg (0.486 mmol) of (S,S)-(2'-nitrophenyl)methane-SO₂DPEN (MW: 411.48), and 149 mg (0.243 mmol) of [RuCl₂ (p-cymene)]₂ (MW: 612.4) were introduced into a 20-mL Schlenk tube and subjected to argon-gas replacement. 5 mL of dehydrated methylene chloride and 1.44 mL of 1.0-N KOH solution were added and stirred at room temperature for 1 hr. This solution was washed 6 times with water, Na₂SO₄ was added and stirred for a while, then the supernatant was filtered through a glass filter and transferred to a 50-mL Schlenk tube. The methylene chloride was distilled away under reduced pressure to give Ru[(S,S)-(2'-nitrophenyl)methane-SO₂DPEN](p-cymene). 5 mL of dehydrated methylene chloride was added, and a solution consisting of 39 μL of trifluoromethane sulfonic acid (TfOH) and 5 mL of dehydrated methylene chloride was slowly added dropwise to this mixture, and stirred at room temperature for 1 hr. The resulting solution was concentrated to half or less, and 10 mL of dehydrated TBME was added to deposit crystal, the crystal was collected by filtration through a glass filter, washed with dehydrated TBME and dried under reduced pressure to give Ru(H₂O)(OTf)[(S,S)-(2'-nitrophenyl)methane-SO₂dpen](p-cymene) (hereinafter, abbreviated as Ru(H₂O)(OTf)[(S,S)-2'-NO₂PhCH₂SO₂dpen](p-cymene)).

¹H NMR (400 MHz, CDCl₃, rt, δ/ppm): 1.33 (d, J=6.4 Hz, 3H, CH(CH₃)₂), 1.40 (d, J=6.9 Hz, 3H, CH(CH₃)₂), 2.14 (s, 3H, C₆H₄CH₃), 2.72-2.92 (m, 1H, C₆H₄CH(CH₃)₂), 3.15-3.40 (m, 3H, SO₂CH₂Ar and H₂O), 3.60-3.75 (m, 1H, NHH), 3.75-3.90 (m, 1H, CHNH₂), 4.01 (d, J=11.0 Hz, 1H, CHNSO₂), 4.61 (d, J=13.3 Hz, 1H, SO₂CH₂Ar), 5.60 (d, J=6.0 Hz, 1H, C₆H₄CH₃), 5.64 (d, J=6.0 Hz, 1H, C₆H₄CH₃), 5.78 (d, J=5.5 Hz, 1H, C₆H₄CH₃), 5.90 (d, J=5.5 Hz, 1H, C₆H₄CH₃), 6.58 (br d, J=10.1 Hz, 1H, NHH), 6.85-7.35 (m, 11H, aromatic proton), 7.35-7.55 (m, 2H, aromatic proton), 7.91 (d, J=8.2 Hz, 1H, aromatic proton).

Example 3

Synthesis of (S,S)-(3',5'-dimethoxyphenyl)methane-SO₂DPEN 0.440 g (2.07 mmol) of (S,S)-DPEN (MW: 212.3) was introduced into a 100-mL three-necked flask and subjected to argon-gas replacement. 20 mL of dehydrated methylene chloride and 0.303 mL (2.17 mmol) of triethylamine were added and cooled to 0° C. To this solution, a solution consisting of 0.520 g (2.07 mmol) of 3',5'-dimethoxyphenyl methanesulfonyl chloride (MW: 250.70) and 5 mL of dehydrated methylene chloride was slowly added dropwise, and stirred at 0° C. for 3 hr. This solution was washed twice with water, the solvent in the organic layer was distilled away, and dried under reduced pressure to give a crude product. The crude product was purified by silica-gel column chromatography (silica gel 60N, n-hexane:AcOEt=1:1, then AcOEt 100%) to give 0.51 g of (S,S)-(3',5'-dimethoxyphenyl)methane-SO₂DPEN (58% yield).

$^1$H NMR (400 MHz, CDCl₃, rt, δ/ppm): 3.59 (d, J=13.7 Hz, 1H, SO₂CH₂C₆H₃), 3.64 (d, J=13.7 Hz, 1H, SO₂CH₂C₆H₃), 3.71 (s, 6H, (OCH₃)₂), 4.23 (d, J=6.4 Hz, 1H, CHNH₂), 4.59 (d, J=6.4 Hz, 1H, CHNHSO₂), 6.29 (d, J=2.3 Hz, 2H, C₆H₂H(OCH₃)₂), 6.36 (d, J=2.3 Hz, 1H, C₆H₂H(OCH₃)₂), 7.18-7.40 (m, 10H, aromatic proton).

Example 4

Synthesis of Ru(H₂O)(OTf)[(S,S)-(3',5'-dimethoxyphenyl)methane-SO₂dpen](p-cymene)

200 mg (0.47 mmol) of (S,S)-(3',5'-dimethoxyphenyl)methane-SO₂DPEN (MW: 426.53), and 143 mg (0.23 mmol) of [RuCl₂(p-cymene)]₂ (MW: 612.4) were introduced into a 20-mL Schlenk tube and subjected to argon-gas replacement. 5 mL of dehydrated methylene chloride and 1.4 mL of 1.0-N KOH solution were added and stirred at (room temperature for 1 hr. This solution was washed 6 times with water, Na₂SO₄ was added and stirred for a while, then the supernatant was filtered through a glass filter and transferred to a 50-mL Schlenk tube. The methylene chloride was distilled away under reduced pressure to give Ru[(S,S)-(3',5'-dimethoxyphenyl)methane-SO₂dpen](p-cymene). 5 mL of dehydrated methylene chloride was added, and a solution consisting of 37 µL of TfOH and 5 mL of dehydrated methylene chloride was slowly added dropwise to this mixture, and stirred at room temperature for 1 hr. The resulting solution was concentrated to a volume of approximately 5 mL, and 5 mL of dehydrated TBME was added to deposit crystal, the crystal was collected by filtration through a glass filter, washed with dehydrated TBME and dried under reduced pressure to give Ru(H₂O)(OTf)[(S,S)-(3',5'-dimethoxyphenyl)methane-SO₂dpen](p-cymene) (hereinafter, abbreviated as Ru(H₂O)(OTf)[(S,S)-3',5'-(MeO)₂PhCH₂SO₂dpen](p-cymene)).

$^1$H NMR (400 MHz, CDCl₃, rt, δ/ppm): 1.28 (d, J=6.9 Hz, 6H, CH(CH₃)₂), 2.05 (s, 3H, C₆H₄CH₃), 2.68 (sept, J=6.9 Hz, 1H, C₆H₄CH(CH₃)₂), 3.19 (d, J=13.7 Hz, 1H, SO₂CH₂Ar), 3.50 (d, J=13.7 Hz, 1H, SO₂CH₂Ar), 3.75-3.90 (m, 1H, CHNH₂), 3.70-3.90 (m, 8H, (OCH₃)₂, CHNH₂, and NHH), 4.10-4.25 (m, 3H, CHNSO₂ and H₂O), 5.29 (d, J=6.0 Hz, 1H, C₆H₄CH₃), 5.44-5.54 (m, 2H, C₆H₄CH₃), 5.56 (d, J=6.0 Hz, 1H, C₆H₄CH₃), 6.58 (br d, J=10.1 Hz, 1H, NHH), 6.35-6.55 (m, 4H, NHH and C₆H₃(OCH₃)₂), 6.95-7.30 (m, 10H, aromatic proton).

Example 5

Synthesis of (S,S)-2'-PhOPhCH₂SO₂DPEN 0.518 g (2.44 mmol) of (S,S)-DPEN (MW: 212.3) was introduced into a 50-mL three-necked flask and subjected to argon-gas replacement. 20 mL of dehydrated methylene chloride and 0.357 mL (2.56 mmol) of triethylamine were added and cooled to 0° C. To this solution, a solution consisting of 0.690 g (2.44 mmol) of 2'-phenoxyphenyl methanesulfonyl chloride (MW: 282.74) and 5 mL of dehydrated methylene chloride was slowly added dropwise, and stirred at 0° C. for one night. This solution was washed twice with water, then the solvent in the organic layer was distilled away, and dried under reduced pressure to give a crude product. The crude product was purified by silica-gel column chromatography (silica gel 60N, n-hexane:AcOEt=1:1, then AcOEt 100%) to give 0.615 g of (S,S)-2'-PhOPhCH₂SO₂DPEN (55% yield).

$^1$H NMR (400 MHz, CDCl₃, rt, δ/ppm): 3.57 (d, J=13.7 Hz, 1H, SO₂CH₂Ar), 3.65 (d, J=13.7 Hz, 1H, SO₂CH₂Ar), 4.20 (d, J=6.4 Hz, 1H, CHNH₂), 4.59 (d, J=6.4 Hz, 1H, CHNHSO₂), 6.75-6.80 (m, 1H, aromatic proton), 6.80-6.88 (m, 1H, aromatic proton), 6.88-6.94 (m, 1H, aromatic proton), 6.94-7.10 (m, 1H, aromatic proton), 7.07-7.15 (m, 1H, aromatic proton), 7.15-7.38 (m, 13H, aromatic proton).

Example 6

Synthesis of RuCl[(S,S)-2'-PhOPhCH₂SO₂dpen](p-cymene)

270 mg (0.589 mmol) of (S,S)-2'-PhOPhCH₂SO₂DPEN (MW: 458.57) and 180 mg (0.295 mmol) of [RuCl₂(p-cymene)]₂ (MW: 612.4) were introduced into a 20-mL Schlenk tube and subjected to argon-gas replacement. 20 mL of dehydrated 2-propanol and 164 µL (1.18 mmol) of triethylamine were added and stirred at 80° C. for 1 hr. The solvent was distilled away and ethylene chloride was added, washed with water, then the solvent was distilled away and dried under reduced pressure to give 412 mg of RuCl[(S,S)-2'-PhOPhCH₂SO₂dpen](p-cymene) (96% yield).

$^1$H NMR (400 MHz, CDCl₃, rt, δ/ppm): 1.29 (t, J=6.4 Hz, 6H, CH(CH₃)₂), 2.14 (s, 3H, CH₃C₆H₄CH(CH₃)₂), 2.75-2.96 (m, 1H, CH(CH₃)₂), 3.27 (d, J=13.3 Hz, 1H, SO₂CH₂Ar), 3.40-3.60 (m, 1H, NHH), 3.57 (d, J=13.3 Hz, 1H, SO₂CH₂Ar), 3.62-3.76 (m, 1H, CHNH₂), 3.88 (d, J=11.4 Hz, 1H, CHNSO₂), 5.27 (d, J=6.0 Hz, 1H, CH₃C₆H₄CH(CH₃)₂), 5.34 (d, J=5.0 Hz, 1H, CH₃C₆H₄CH(CH₃)₂), 5.39 (d, J=6.0 Hz, 1H, CH₃C₆H₄CH(CH₃)₂), 5.81 (brs, 1H, NHH), 6.75-7.40 (m, 19H, aromatic proton).

Example 7

Synthesis of (S,S)—(C₂H₅)₂CHCH₂SO₂DPEN 0.592 g (2.79 mmol) of (S,S)-DPEN (MW: 212.3) was introduced into a 50-mL three-necked flask and subjected to argon-gas replacement. 25 mL of dehydrated methylene chloride and 0.41 mL (2.93 mmol) of triethylamine were added and cooled to 0° C. To this solution, a solution consisting of 0.515 g (2.79 mmol) of isohexyl sulfonyl chloride (MW: 184.68) and 25 mL of dehydrated methylene chloride was slowly added dropwise, and stirred at 0° C. for one night. This solution was washed twice with water, then the solvent in the organic layer was distilled away, and dried under reduced pressure to give 1.656 g of a crude product. The crude product was purified by silica-gel column chromatography (silica gel 60N, n-hexane:AcOEt=1:1, then AcOEt 100%) to give 0.306 g of (S,S)—(C₂H₅)₂CHCH₂SO₂DPEN (30% yield).

$^1$H NMR (400 MHz, CDCl₃, rt, δ/ppm): 0.67 (q, J=7.3 Hz, 6H, (CH₃CH₂)₂CH), 1.10-1.38 (m, 4H, (CH₃CH₂)₂CH), 1.62-1.76 (m, 1H, (CH₃CH₂)₂CH), 2.22 (d, J=6.4 Hz, 2H, CH₂SO₂), 4.29 (d, J=5.5 Hz, 1H, C₆H₅CHNH₂), 4.56 (d, J=5.5 Hz, 1H, C₆H₅CHNHSO₂), 7.15-7.45 (m, 10H, aromatic proton).

Example 8

Synthesis of RuCl[(S,S)—(C$_2$H$_5$)$_2$CHCH$_2$SO$_2$dpen] (p-cymene)

108 mg (0.30 mmol) of (S,S)—(C$_2$H$_5$)$_2$CHCH$_2$SO$_2$DPEN (MW: 360.51) and 92 mg (0.15 mmol) of [RuCl$_2$(p-cymene)]$_2$ (MW: 612.4) were introduced into a 20-mL Schlenk tube and subjected to argon-gas replacement. 10 mL of dehydrated 2-propanol and 84 μL (0.60 mmol) of triethylamine were added and stirred at 80° C. for 2 hr. The solvent was distilled away, ethylene chloride was added, washed with water, then the solvent was distilled away, and dried under reduced pressure to give 180 mg of RuCl[(S,S)—(C$_2$H$_5$)$_2$CHCH$_2$SO$_2$dpen](p-cymene) (95% yield).

$^1$H NMR (400 MHz, CDCl$_3$, rt, δ/ppm): 0.64 (t, J=7.8 Hz, 3H, (CH$_3$CH$_2$)$_2$CH), 0.71 (t, J=7.8 Hz, 3H, (CH$_3$CH$_2$)$_2$CH), 1.13-1.35 (m, 4H, (CH$_3$CH$_2$)$_2$CH), 1.38 (d, J=6.9 Hz, 6H, C$_6$H$_4$CH(CH$_3$)$_2$) 1.65-1.82 (m, 1H, (CH$_3$CH$_2$)$_2$CH), 2.33 (m, 5H, (CH$_3$CH$_2$)$_2$CHCH$_2$ and C$_6$H$_4$CH$_3$), 2.98-3.12 (m, 1H, C$_6$H$_4$CH(CH$_3$)$_2$), 3.47-3.62 (m, 1H, NHH), 3.62-3.75 (m, 1H, CHNH$_2$), 3.81 (d, J=11.0 Hz, 1H, CHNSO$_2$), 5.69 (d, J=5.5 Hz, 1H, C$_6$H$_4$CH$_3$), 5.62 (d, J=6.0 Hz, 2H, C$_6$H$_4$CH$_3$), 5.57 (d, J=5.0 Hz, 1H, C$_6$H$_4$CH$_3$), 5.91 (brs, 1H, NHH), 6.72-6.94 (m, 4H, aromatic proton), 6.94-7.10 (m, 6H, aromatic proton).

Example 9

Synthesis of (S,S)-2',6'-Me$_2$PhCH$_2$SO$_2$DPEN 0.254 g (1.20mmol) of (S,S)-DPEN (MW: 212.3) was introduced into a 50-mL three-necked flask and subjected to argon-gas replacement. 10 mL of dehydrated methylene chloride and 0.200 mL (1.44 mmol) of triethylamine were added and cooled to 0° C. To this solution, a solution consisting of 0.262 g (1.20-mmol) of 2',6'-dimethylphenyl methanesulfonyl chloride (MW: 218.70) and 5 mL of dehydrated methylene chloride was slowly added dropwise, and stirred at 0° C. for one night. This solution was washed twice with water, then the solvent in the organic layer was distilled away, and dried under reduced pressure to give a crude product. The crude product was purified by silica-gel column chromatography (silica gel 60N, n-hexane:AcOEt=1:1, then AcOEt 100%) to give 0.255 g of (S,S)-2',6'-Me$_2$PhCH$_2$SO$_2$DPEN (54% yield).

$^1$H NMR (400 MHz, CDCl$_3$, rt, δ/ppm): 2.20 (s, 6H, C$_6$H$_3$(CH$_3$)$_2$), 3.59 (d, J=14.2 Hz, 1H, SO$_2$CH$_2$Ar), 3.79 (d, J=14.2 Hz, 1H, SO$_2$CH$_2$Ar), 4.25 (d, J=6.4 Hz, 1H, CHNH$_2$), 4.63 (d, J=6.4 Hz, 1H, CHNHSO$_2$), 6.93 (d, J=7.8 Hz, 2H, C$_6$H$_3$(CH$_3$)$_2$), 7.03 (d, J=7.8 Hz, 1H, C$_6$H$_3$(CH$_3$)$_2$), 7.15-7.45 (m, 10H, aromatic proton).

Example 10

Synthesis of RuCl[(S,S)-2',6'-Me$_2$PhCH$_2$SO$_2$dpen] (p-cymene)

86 mg (0.218 mmol) of (S,S)-2',6'-Me$_2$PhCH$_2$SO$_2$DPEN (MW: 394.53) and 67 mg (0.109 mmol) of [RuCl$_2$(p-cymene)]$_2$ (MW: 612.4) were introduced into a 20-mL Schlenk tube and subjected to argon-gas replacement. 5 mL of dehydrated 2-propanol and 61 μL (0.436 mmol) of triethylamine were added and stirred at 80° C. for 1 hr. The solvent was distilled away, ethylene chloride was added, washed with water, then the solvent was distilled away, and dried under reduced pressure to give 139 mg of RuCl[(S,S)-2',6'-Me$_2$PhCH$_2$SO$_2$dpen](p-cymene) (96% yield).

$^1$H NMR (400 MHz, CDCl$_3$, rt, δ/ppm): 1.10-1.30 (m, 3H, C$_6$H$_4$CH(CH$_3$)$_2$), 1.34 (d, J=6.9 Hz, 3H, C$_6$H$_4$CH(CH$_3$)$_2$), 2.00-2.35 (m, 9H, C$_6$H$_4$CH$_3$ and C$_6$H$_3$(CH$_3$)$_2$), 2.90-3.08 (m, 1H, C$_6$H$_4$CH(CH$_3$)$_2$), 3.32-3.86 (m, 5H, SO$_2$CH$_2$Ar, CHNSO$_2$, CHNH$_2$ and NHH), 5.45-5.61 (m, 2H, C$_6$H$_4$CH$_3$), 5.61-5.80 (m, 2H, C$_6$H$_4$CH$_3$), 6.60-7.15 (m, 13H, aromatic proton).

Example 11

Synthesis of (S,S)-(2-(1-naphtyl)-ethane)SO$_2$DPEN 0.833 g (3.93 mmol) of (S,S)-DPEN (MW: 212.3) was introduced into a 100-mL three-necked flask and subjected to argon-gas replacement. 40 mL of dehydrated methylene chloride and 0.58 mL (4.13 mmol) of triethylamine were added and cooled to 0° C. To this solution, a solution consisting of 1.0 g (3.93 mmol) of 2-(1-naphtyl)-ethanesulfonyl chloride (MW: 254.73) and 10 mL of dehydrated methylene chloride was slowly added dropwise, and stirred at 0° C. for 3 hr. This solution was washed twice with water, then the solvent in the organic layer was distilled away, and dried under reduced pressure to give a crude product. The crude product was purified by silica-gel column chromatography (silica gel 60N, n-hexane:AcOEt=1:1, then AcOEt 100%) to give 1.13 g of (S,S)-(2-(1-naphtyl)-ethane)SO$_2$DPEN (67% yield).

$^1$H NMR (400 MHz, CDCl$_3$, rt, δ/ppm): 2.67 (ddd, J=14.2, 11.9, 5.0 Hz, 1H, SO$_2$CH$_2$CH$_2$), 2.79 (ddd, J=14.2, 11.9, 5.0 Hz, 1H, SO$_2$CH$_2$CH$_2$), 3.24 (ddd, J=14.2, 11.9, 5.0 Hz, 1H, SO$_2$CH$_2$CH$_2$), 3.32 (ddd, J=14.2, 11.9, 5.0Hz, 1H, SO$_2$CH$_2$CH$_2$), 4.27 (d, J=5.5 Hz, 1H, CHNH$_2$), 4.63 (d, J=5.5 Hz, 1H, CHNSO$_2$), 6.97-7.05 (m, 2H, aromatic proton), 7.11-7.20 (m, 2H, aromatic proton), 7.22-7.38 (m, 8H, aromatic proton), 7.42-7.51 (m, 2H, aromatic proton), 7.65-7.74 (m, 2H, aromatic proton), 7.79-7.87 (m, 1H, aromatic proton).

Example 12

Synthesis of Ru(H$_2$O)(OTf)[(S,S)-(2-(1-naphtyl)-ethane)SO$_2$dpen](p-cymene)

200 mg (0.47 mmol) of (S,S)-(2-(1-naphtyl)-ethane) SO$_2$DPEN (MW: 430.56) and 142 mg (0.23 mmol) of [RuCl$_2$(p-cymene)]$_2$ (MW: 612.4) were introduced into a 20-mL Schlenk tube and subjected to argon-gas replacement. 5 mL of dehydrated methylene chloride and 1.4 mL of 1.0-N KOH solution were added and stirred at room temperature for 1 hr. This solution was washed 6 times with water, Na$_2$SO$_4$ was added and stirred for a while, then the supernatant was filtered through a glass filter and transferred to a 50-mL Schlenk tube. The methylene chloride was distilled away under reduced pressure to give Ru[(S,S)—(CH$_3$)$_2$CHCH$_2$SO$_2$dpen](p-cymene). 10 mL of dehydrated methylene chloride was added, and while a solution consisting of 37 μL of TfOH and 5 mL of dehydrated methylene chloride was slowly added dropwise, the mixture was stirred at room temperature for 1 hr. Since the resulting solution was concentrated to deposit crystal, it is stirred with addition of dehydrated TBME, the crystal was collected by filtration through a glass filter, washed with a small amount of dehydrated TBME, dried under reduced pressure to give 269 mg of Ru(H$_2$O)(OTf)[(S,S)-(2-(1-naphtyl)-ethane)SO$_2$dpen](p-cymene) (hereinafter, abbreviated as Ru(H$_2$O)(OTf)[(S,S)-(1-naphtyl)CH$_2$CH$_2$SO$_2$dpen](p-cymene)) (70% yield).

$^1$H NMR (400 MHz, CDCl$_3$, rt, δ/ppm): 1.36 (d, J=6.9 Hz, 3H, CH(CH$_3$)$_2$), 1.40 (d, J=6.9 Hz, 3H,), 2.17 (s, 3H, C$_6$H$_4$CH$_3$), 2.48-2.61 (m, 1H, SO$_2$CH$_2$CH$_2$), 2.61-2.72 (m, 1H, SO$_2$CH$_2$CH$_2$), 2.80-2.95 (m, 1H, CH(CH$_3$)$_2$), 3.15-3.55 (m, 4H, SO$_2$CH$_2$CH$_2$ and H$_2$O), 3.74-3.85 (m, 1H, NHH), 3.85-3.98 (m, 1H, CHNH$_2$), 4.01 (d, J=10.5 Hz, 1H, CHNSO$_2$), 5.47 (d, J=5.5 Hz, 1H, C$_6$H$_4$CH$_3$) 5.73 (d, J=6.0 Hz, 1H, C$_6$H$_4$CH$_3$), 5.85 (brs, 1H, C$_6$H$_4$CH$_3$), 5.97 (d, J=5.5 Hz, 1H, C$_6$H$_4$CH$_3$), 6.46 (brd, J=10.5 Hz, 1H, NHH), 6.90 (d, J=6.9 Hz, 1H, aromatic proton), 6.95-7.35 (m, 11H, aromatic proton), 7.40-7.51 (m, 2H, aromatic proton), 7.67 (d, J=8.2 Hz, 1H, aromatic proton), 7.73-7.86 (m, 2H, aromatic proton).

Example 13

Synthesis of Cp*IrCl[(S,S)-(C$_2$H$_5$)$_2$CHCH$_2$SO$_2$dpen]

102 mg (0.283 mmol) of (S,S)-(C$_2$H$_5$)$_2$CHCH$_2$SO$_2$DPEN (MW: 360.51) and 103 mg (0.129 mmol) of [Cp*IrCl$_2$]$_2$ (MW: 796.67) were introduced into a 20-mL Schlenk tube and subjected to argon-gas replacement. 5 mL of dehydrated 2-propanol and 76 µL of triethylamine were added and stirred at room temperature for 2 hr. The deposited yellow crystal was collected by filtration, then the crystal was sequentially washed with a small amount of 2-propanol, water, and a small amount of 2-propanol, and dried under reduced pressure to give 117 mg of Cp*IrCl[(S S)—(C$_2$H$_5$)$_2$CHCH$_2$SO$_2$dpen] (63% yield).

$^1$H NMR (400 MHz, CDCl$_3$, rt, δ/ppm): 0.57 (t, J=7.3 Hz, 3H, CH$_2$CH$_3$), 0.85 (d, J=6.9 Hz, 3H, CH$_2$CH$_3$), 1.10-1.45 (m, 4H, CH(CH$_2$CH$_3$)$_2$), 1.70-1.85 (m, 1H, CH(CH$_2$CH$_3$)$_2$), 2.21 (dd, J=13.7, 6.0 Hz, 1H, SO$_2$CH$_2$CH), 2.33 (dd, J=13.7, 6.0 Hz, 1H, SO$_2$CH$_2$CH), 3.77 (m, 1H, CHNH$_2$), 4.06 (brd, J=10.1 Hz, 1H, NHH), 4.58 (1H, NHH), 4.60 (d, J=10.5 Hz, 1H, CHNSO$_2$), 6.96-7.03 (m, 2H, aromatic proton), 7.04-7.24 (m, 8H, aromatic proton).

[Asymmetric Reduction]

Tables 1 and 2 show results of the use of ruthenium catalysts of the examples and comparative examples for asymmetric reduction of ketone substrates, and Table 3 shows results of the use of iridium catalysts. In these tables, S/C represents a ratio of substrate/catalyst, and "yield, %" and "ee, %" represent a yield and an enantiometric excess in percentage of a product, respectively. Here, inmost of the reaction examples, the yields did not reach 100%; this is because S/C values were set for the comparison of catalyst performance. Accordingly, these expressed yields do not necessarily show a maximum yield. For cases wherein reaction is not completed, the reaction can be completed by decreasing S/C values.

TABLE 1

| | | Substrate | | | | | | | | |
|---|---|---|---|---|---|---|---|---|---|---|
| | | A | | B | | C | | D | | E |
| | | \[2'-methoxyacetophenone\] | | \[4'-methylacetophenone\] | | \[3',5'-bis(trifluoromethyl)acetophenone\] | | \[2',5'-dimethylacetophenone\] | | \[3'-(trifluoromethyl)acetophenone\] |
| | | S/C | | | | | | | | |
| | | 3.000 | | 5.000 | | 5.000 | | 1.000 | | 5.000 |
| | | HCOOK (eq.) | | | | | | | | |
| Cat- | | 1.2 | | 2.0 | | 2.0 | | 2.0 | | 2.0 |
| alyst No. | Ruthenium catalyst | Yield. % | ee. % | Yield. % | ee. % | Yield. % | ee. % | Yield. % | ee. % | Yield. % | ee. % |
| 1 | Ru(OTf)[(S,S)-Tsdpen](p-cymene) | 61 | 76.0 | 90 | 92.9 | — | — | 95 | 72.9 | 100 | 90.0 |
| 2 | Ru(OTF)[(R)-Cs-(R,R)-dpen](p-cymene) | 88 | 76.6 | 51 | 89.6 | 60 | 75.2 | 95 | 73.2 | 100 | 93.4 |
| 3 | Ru(H$_2$O)(OTf)[(S,S)-2'-NO$_2$PhCH$_2$SO$_2$dpen](p-cymene) | — | — | 18 | 95.5 | — | — | — | — | — | — |
| 4 | Ru(H$_2$O)(OTf)[(S,S)-3',5'-(MeO)$_2$PhCH$_2$SO$_2$dpen](p-cymene) | — | — | 80 | 94.2 | — | — | — | — | — | — |
| 5 | RuCl[(S,S)-2'-PhOPhCH$_2$SO$_2$dpen](p-cymene) | — | — | 90 | 93.6 | — | — | — | — | — | — |
| 6 | RuCl[(S,S)-(C$_2$H$_5$)$_2$CHCH$_2$SO$_2$dpen](p-cymene) | 99 | 88.1 | 97 | 93.9 | 70 | 91.1 | 100 | 91.8 | 99 | 93.5 |
| 7 | RuCl[(S,S)-2',6'-Me$_2$PhCH$_2$SO$_2$dpen](p-cymene) | 86 | 82.4 | — | — | 88 | 94.8 | 100 | 92.9 | 100 | 93.7 |
| 8 | Ru(H$_2$O)(OTf)[(S,S)-(1-naphthyl)CH$_2$CH$_2$SO$_2$dpen](p-cymene) | — | — | 46 | 94.6 | — | — | — | — | — | — |

TABLE 2

| | | Substrate | | | | | | | | |
|---|---|---|---|---|---|---|---|---|---|---|
| | | F | | G | | H | | I | | J |
| | | 4-CF3-acetophenone | | 3,4-diCl-acetophenone | | 2-NO2-acetophenone | | 1-(3-NO2-phenyl)ethanol | | 4-CN-acetophenone |
| | | S/C | | | | | | | | |
| | | 7,000 | | 7,000 | | 5,000 | | 5,000 | | 5,000 |
| | | HCOOK (eq.) | | | | | | | | |
| Cat- | | 2.0 | | 2.0 | | 2.0 | | 2.0 | | 2.0 |
| alyst No. | Ruthenium catalyst | Yield. % | ee. % | Yield. % | ee. % | Yield. % | ee. % | Yield. % | ee. % | Yield. % | ee. % |
| 1 | Ru(OTf)[(S,S)-Tsdpen](p-cymene) | 94 | 91.9 | 100 | 87.8 | 46 | 86.7 | 64 | 75.8 | 100 | 84.5 |
| 2 | Ru(OTF)[(R)-Cs-(R,R)-dpen](p-cymene) | 68 | 94.8 | 94 | 92.9 | 37 | 93.0 | 68 | 84.5 | 71 | 90.7 |
| 3 | Ru(H2O)(OTf)[(S,S)-2'-NO2PhCH2SO2dpen](p-cymene) | — | — | — | — | — | — | — | — | — | — |
| 4 | Ru(H2O)(OTf)[(S,S)-3',5'-(MeO)2PhCH2SO2dpen](p-cymene) | — | — | — | — | — | — | — | — | — | — |
| 5 | RuCl[(S,S)-2'-PhOPhCH2SO2dpen](p-cymene) | — | — | — | — | — | — | — | — | — | — |
| 6 | RuCl[(S,S)-(C2H5)2CHCH2SO2dpen](p-cymene) | 61 | 94.9 | 100 | 92.5 | 48 | 93.0 | 65 | 85.4 | 100 | 89.4 |
| 7 | RuCl[(S,S)-2',6'-Me2PhCH2SO2dpen](p-cymene) | 100 | 94.6 | — | — | — | — | — | — | — | — |
| 8 | Ru(H2O)(OTf)[(S,S)-(1-naphthyl)CH2CH2SO2dpen](p-cymene) | — | — | — | — | — | — | — | — | — | — |

TABLE 3

| | | Substrate | | | | | | | |
|---|---|---|---|---|---|---|---|---|---|
| | | A | | C | | E | | F | |
| | | 2-OMe-acetophenone | | 3,5-bis(CF3)-acetophenone | | 3-CF3-acetophenone | | 4-CF3-acetophenone | |
| | | S/C | | | | | | | |
| | | 3,000 | | 5,000 | | 5,000 | | 7,000 | |
| Cat- | | HCOOK (eq.) | | | | | | | |
| alyst | | 1.2 | | 2.0 | | 2.0 | | 2.0 | |
| No. | Iridium catalyst | Yield. % | ee. % | Yield. % | ee. % | Yield. % | ee. % | Yield. % | ee. % |
| 9 | Cp*Ir(OTf)[(S)-Cs-(S,S)-dpen] | 70 | 81.4 | 100 | 68.4 | 100 | 92.0 | 100 | 93.6 |
| 10 | Cp*IrCl[(S,S)-(C2H5)2CHCH2SO2dpen] | 58 | 86.9 | 100 | 84.2 | 100 | 94.3 | 100 | 95.9 |

Comparative Example A-1

Asymmetric Reduction of 2'-methoxyacetophenone by Ru(OTf)[(S,S)-Tsdpen](p-cymene) Complex Using Potassium Formate Solution as Hydrogen Source (Comparison of Catalyst)

In a 20-mL Schlenk tube, 1.01 g (12.0 mmol) of HCOOK as a hydrogen source, 32.2 mg (100 μmol) of tetra-n-butylammonium bromide as a phase-transfer catalyst, and 2.50 mg (3.33 μmol) of Ru(OTf)[(S,S)-Tsdpen](p-cymene) as a catalyst were introduced, and subjected to argon-gas replacement. 1.38 mL (10.0 mmol) of 2'-methoxyactophenone and 2 mL of water were added, and stirred at 50° C. for 24 hr. The organic phase was washed 3 times with 3 mL of water to give an optically-active alcohol. GC analysis of the reaction product confirmed that 1-(2'-methoxyphenyl)ethanol with 76.0% ee optical purity was produced at 61% yield.

Comparative Example A-2

Asymmetric Reduction of 2'-methoxyacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example A-1, except that 2.69 mg (3.33 μmol) of Ru(OTf)[(R)—Cs—(R,R)-dpen](p-cymene) was used as the catalyst. GC analysis of the reaction product confirmed that 1-(2'-methoxyphenyl)ethanol with 76.6% ee optical purity was produced at 88% yield.

Example A-6

Asymmetric Reduction of 2'-methoxyacetophenone by RuCl[(S,S)—(C$_2$H$_5$)$_2$CHCH$_2$SO$_2$dpen](p-cymene) Complex Using Potassium Formate Solution as Hydrogen Source The reaction was carried out with the same conditions as in Comparative example A-1, except that 2.10 mg (3.33 μmol) of RuCl[(S,S)—(C$_2$H$_5$)$_2$CHCH$_2$SO$_2$dpen](p-cymene) was used as the catalyst. GC analysis of the reaction product confirmed that 1-(2'-methoxyphenyl)ethanol with 88.1% ee optical purity was produced at 99% yield. Comparison with Comparative examples A-1 and A-2 indicated the superiority of this complex.

Example A-7

Asymmetric Reduction of 2'-methoxyacetophenone by RuCl[(S,S)-2',6'-Me$_2$PhCH$_2$SO$_2$dpen](p-cymene) Complex Using Potassium Formate Solution as Hydrogen Source The reaction was carried out with the same conditions as in Comparative example A-1, except that 2.21 mg (3.33 μmol) of RuCl[(S,S)-2',6'-Me$_2$PhCH$_2$SO$_2$dpen](p-cymene) was used as the catalyst. GC analysis of the reaction product confirmed that 1-(2'-methoxyphenyl)ethanol with 82.4% ee optical purity was produced at 86% yield. Comparison with Comparative examples A-1 and A-2 indicated the superiority of this complex.

Comparative Example A-9

Asymmetric Reduction of 2'-methoxyacetophenone by Cp*Ir(OTf)[(S)—Cs—(S,S)-dpen] Complex Using Potassium Formate Solution as Hydrogen Source (Comparison of Catalyst)

In a 20-mL Schlenk tube, 1.01 g (12.0 mmol) of HCOOK as a hydrogen source, 32.2 mg (100 μmol) of tetra-n-butylammonium bromide as a phase-transfer catalyst, and 3.05 mg (3.33 μmol) of Cp*Ir(OTf)[(S)—Cs—(S,S)-dpen] as a catalyst are introduced, and subjected to argon-gas replacement. 1.38 mL (10.0 mmol) of 2'-methoxyactophenone and 2 mL of water are added, and stirred at 50° C. for 24 hr. The organic phase was washed 3 times with 3 mL of water to give an optically-active alcohol. GC analysis of the reaction product confirmed that 1-(2'-methoxyphenyl)ethanol with 81.4% ee optical purity was produced at 70% yield.

Example A-10

Asymmetric Reduction of 2'-methoxyacetophenone by Cp*IrCl[(S,S)—(C$_2$H$_5$)$_2$CHCH$_2$SO$_2$dpen] Complex Using Potassium Formate Solution as Hydrogen Source The reaction was carried out with the same conditions as in Comparative example A-9, except that 2.41 mg (3.33 μmol) of Cp*IrCl[(S,S)—(C$_2$H$_5$)$_2$CHCH$_2$SO$_2$dpen] was used as the catalyst. GC analysis of the reaction product confirmed that 1-(2'-methoxyphenyl)ethanol with 86.9% ee optical purity was produced at 58% yield. Comparison with Comparative example A-9 indicated the superiority of this complex.

Comparative Example B-1

Asymmetric Reduction of 4'-methylacetophenone by Ru(OTf)[(S,S)-Tsdpen](p-cymene) Complex Using Potassium Formate Solution as Hydrogen Source (Comparison of Catalyst)

In a 20-mL Schlenk tube, 1.68 g (20.0 mmol) of HCOOK as a hydrogen source, 32.2 mg (100 μmol) of tetra-n-butylammonium bromide as a phase-transfer catalyst, and 1.50 mg (2.0 μmol) of Ru(OTf)[(S,S)-Tsdpen](p-cymene) as a catalyst were introduced and subjected to argon-gas replacement. 1.34 mL (10.0 mmol) of 4'-methylacetophenone and 2 mL of water were added and stirred at 50° C. for 24 hr. The organic phase was washed 3 times with 3 mL of water to give an optically-active alcohol. GC analysis of the reaction product confirmed that 1-(4'-methylphenyl)ethanol with 92.9% ee optical purity was produced at 90% yield.

Comparative Example B-2

Asymmetric Reduction of 4'-methylacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example B-1, except that 1.62 mg (2.0 μmol) of Ru(OTf)[(R)—Cs—(R,R)-dpen](p-cymene) was used as the catalyst. GC analysis of the reaction product confirmed that 1-(4'-methylphenyl)ethanol with 89.6% ee optical purity was produced at 51% yield.

Example B-3

Asymmetric Reduction of 4'-methylacetophenone by Ru(H$_2$O)(OTf)[(S,S)-2'-NO$_2$PhCH$_2$SO$_2$dpen](p-cymene) Complex Using Potassium Formate Solution as Hydrogen Source The reaction was carried out with the same conditions as in Comparative example B-1, except that 1.59 mg (2.0 μmol) of Ru(H$_2$O)(OTf)[(S,S)-2'-NO$_2$PhCH$_2$SO$_2$dpen](p-cymene) was used as the catalyst. GC analysis of the reaction product confirmed that 1-(4'-methylphenyl)ethanol with 95.5% ee optical purity was produced at 18% yield. Comparison with Comparative examples B-1 and B-2 indicated the superiority of this complex.

Example B-4

Asymmetric Reduction of 4'-methylacetophenone by Ru(H$_2$O)(OTf)[(S,S)-3',5'-(MeO)$_2$PhCH$_2$SO$_2$dpen](p-cymene) Complex Using Potassium Formate Solution as Hydrogen Source The reaction was carried out with the same conditions as in Comparative example B-1, except that 1.62 mg (2.0 μmol) of Ru(H$_2$O)(OTf)[(S,S)-3',5'-(MeO)$_2$PhCH$_2$SO$_2$dpen](p-cymene) was used as the catalyst. GC analysis of the reaction product confirmed that 1-(4'-methylphenyl)ethanol with 94.2% ee optical purity was produced at 80% yield. Comparison with Comparative examples B-1 and B-2 indicated the superiority of this complex.

Example B-5

Asymmetric Reduction of 4'-methylacetophenone by RuCl[(S,S)-2'-PhOPhCH$_2$SO$_2$dpen](p-cymene) Complex Using Potassium Formate Solution as Hydrogen Source The reaction was carried out with the same conditions as in Comparative example B-1, except that 1.46 mg (2.0 μmol) of RuCl[(S,S)-2'-PhOPhCH$_2$SO$_2$dpen](p-cymene) was used as the catalyst. GC analysis of the reaction product confirmed that 1-(4'-methylphenyl)ethanol with 93.6% ee optical purity was produced at 90% yield. Comparison with Comparative examples B-1 and B-2 indicated the superiority of this complex.

Example B-6

Asymmetric Reduction of 4'-methylacetophenone by RuCl[(S,S)-(C$_2$H$_5$)$_2$CHCH$_2$SO$_2$dpen](p-cymene) Complex Using Potassium Formate Solution as Hydrogen Source The reaction was carried out with the same conditions as in Comparative example B-1, except that 1.26 mg (2.0 μmol) of RuCl[(S,S)—(C$_2$H$_5$)$_2$CHCH$_2$SO$_2$dpen](p-cymene) was used as the catalyst. GC analysis of the reaction product confirmed that 1-(4'-methylphenyl)ethanol with 93.9% ee optical purity was produced at 97% yield. Comparison with Comparative examples B-1 and B-2 indicated the superiority of this complex.

Example B-8

Asymmetric Reduction of 4'-methylacetophenone by Ru(OTf)[(S,S)-(1-naphtyl)CH$_2$CH$_2$SO$_2$dpen](p-cymene) Complex Using Potassium Formate Solution as Hydrogen Source The reaction was carried out with the same conditions as in Comparative example B-1, except that 1.63 mg (2.0 μmol) of Ru(OTf)[(S,S)-(1-naphtyl)CH$_2$CH$_2$SO$_2$dpen](p-cymene) was used as the catalyst. GC analysis of the reaction product confirmed that 1-(4'-methylphenyl)ethanol with 94.6% ee optical purity was produced at 46% yield. Comparison with Comparative examples B-1 and B-2 indicated the superiority of this complex.

Comparative Example C-2

Asymmetric Reduction of 3',5'-bis(trifluoromethyl)acetophenone by Ru(OTf)[(R)—Cs—(R,R)-dpen](p-cymene) Complex Using Potassium Formate Solution as Hydrogen Source (Comparison of Catalyst)

In a 20-mL Schlenk tube, 841 mg (10.0 mmol) of HCOOK as a hydrogen source, 16.1 mg (50 μmol) of tetra-n-butylammonium bromide as a phase-transfer catalyst, and 0.81 mg (1.0 μmol) of Ru(OTf)[(R)—Cs—(R,R)-dpen](p-cymene) as a catalyst were introduced and subjected to argon-gas replacement. 902 in (5.0 mmol) of 3',5'-bis(trifluoromethyl)acetophenone and 1 mL of water were added and stirred at 50° C. for 24 hr. The organic phase was washed 3 times with 3 mL of water to give an optically-active alcohol. GC analysis of the reaction product confirmed that 1-(3',5'-bis(trifluoromethyl)phenyl)ethanol with 75.2% ee optical purity was produced at 60% yield.

Example C-6

Asymmetric Reduction of 3',5'-bis(trifluoromethyl)acetophenone by RuCl[(S,S)—(C$_2$H$_5$)$_2$CHCH$_2$SO$_2$dpen](p-cymene) Complex Using Potassium Formate Solution as Hydrogen Source The reaction was carried out with the same conditions as in Comparative example C-2, except that 0.63 mg (1.0 μmol) of RuCl[(S,S)—(C$_2$H$_5$)$_2$CHCH$_2$SO$_2$dpen](p-cymene) was used as the catalyst. GC analysis of the reaction product confirmed that that 1-(3',5'-bis(trifluoromethyl)phenyl)ethanol with 91.1% ee optical purity was produced at 70% yield. Comparison with Comparative example C-2 indicated the superiority of this complex.

Example C-7

Asymmetric Reduction of 3',5'-bis(trifluoromethyl)acetophenone by RuCl[(S,S)-2',6'-Me$_2$PhCH$_2$SO$_2$dpen](p-cymene) Complex Using Potassium Formate Solution as Hydrogen Source The reaction was carried out with the same conditions as in Comparative example C-2, except that 0.66 mg (1.0 μmol) of RuCl[(S,S)-2',6'-Me$_2$PhCH$_2$SO$_2$dpen](p-cymene) was used as the catalyst. GC analysis of the reaction product confirmed that 1-(3',5'-bis(trifluoromethyl)phenyl)ethanol with 94.8% ee optical purity was produced at 88% yield. Comparison with Comparative example C-2 indicated the superiority of this complex.

Comparative Example C-9

Asymmetric Reduction of 3',5'-bis(trifluoromethyl) acetophenone by Cp*Ir(OTf)[(S)—Cs—(S,S)-dpen] Complex Using Potassium Formate Solution as Hydrogen Source (Comparison of Catalyst)

In a 20-mL Schlenk tube, 841 mg (10.0 mmol) of HCOOK as a hydrogen source, 16.1 mg (50 µmol) of tetra-n-butylammonium bromide as a phase-transfer catalyst, and 0.92 mg (1.0 µmol) of Cp*Ir(OTf)[(S)—Cs—(S,S)-dpen] as a catalyst were introduced and subjected to argon-gas replacement. 902 µL (5.0 mmol) of 3',5'-bis(trifluoromethyl)acetophenone and 1 mL of water were added and stirred at 50° C. for 24 hr. The organic phase was washed 3 times with 3 mL of water to give an optically-active alcohol. GC analysis of the reaction product confirmed that 1-(3',5'-bis(trifluoromethyl)phenyl)ethanol with 68.4% ee optical purity was produced at 100% yield.

Example C-10

Asymmetric Reduction of 3',5'-bis(trifluoromethyl) acetophenone by Cp*IrCl[(S,S)—($C_2H_5$)$_2$CHCH$_2$SO$_2$dpen] Complex Using Potassium Formate Solution as Hydrogen Source The reaction was carried out with the same conditions as in Comparative example C-9, except that 0.72 mg (1.0 µmol) of Cp*IrCl[(S,S)-($C_2H_5$)$_2$CHCH$_2$SO$_2$dpen] was used as the catalyst. GC analysis of the reaction product confirmed that 1-(3',5'-bis(trifluoromethyl)phenyl)ethanol with 84.2% ee optical purity was produced at 100% yield. Comparison with Comparative example C-9 indicated the superiority of this complex.

Comparative Example C-102

Asymmetric Reduction of 3',5'-bis(trifluoromethyl) acetophenone by Catalyst Comprising (R)—Cs—(R,R)-DPEN and [RuCl$_2$(p-cymene)]$_2$ Using Potassium Formate Solution as Hydrogen Source The reaction was carried out with the same conditions as in Comparative example C-2, except that 0.86 mg (2.0 µmol) of (R)—Cs—(R,R)-DPEN and 0.61 mg (1.0 µmol) of [RuCl$_2$(p-cymene)]$_2$ as the catalyst, 1.68 g (20.0 mmol) of HCOOK, and 32.2 mg (100 µmol) of tetra-n-butylammonium bromide, 1.80 mL (10.0 mmol) of 3',5'-bis(trifluoromethyl)acetophenone and 2 mL of water were used. GC analysis of the reaction product confirmed that 1-(3',5'-bis(trifluoromethyl)phenyl)ethanol with 74.0% ee optical purity was produced at 100% yield.

Example C-106

Asymmetric Reduction of 3',5'-bis(trifluoromethyl) acetophenone by Catalyst Comprising (S,S)—($C_2H_5$)$_2$CHCH$_2$SO$_2$DPEN and [RuCl$_2$(p-cymene)]$_2$ Using Potassium Formate Solution as Hydrogen Source The reaction was carried out with the same conditions as in Comparative example C-102, except that 0.72 mg (2.0 µmol) of (S,S)—($C_2H_5$)$_2$CHCH$_2$SO$_2$DPEN and 0.61 mg (1.0 µmol) of [RuCl$_2$(p-cymene)]$_2$ were used as the catalyst. GC analysis of the reaction product confirmed that 1-(3',5'-bis(trifluoromethyl)phenyl)ethanol with 91.5% ee optical purity was produced at 100% yield. Comparison with Comparative example C-102 indicated the superiority of this complex. In addition, superiority of (S,S)—($C_2H_5$)$_2$CHCH$_2$SO$_2$DPEN was also confirmed.

Example C-107

Asymmetric Reduction of 3',5'-bis(trifluoromethyl) acetophenone by Catalyst Comprising (S,S)-2',6'-Me$_2$PhCH$_2$SO$_2$DPEN and [RuCl$_2$(p-cymene)]$_2$ Using Potassium Formate Solution as Hydrogen Source The reaction was carried out with the same conditions as in Comparative example C-102, except that 0.78 mg (2.0 µmol) of (S,S)-2',6'-Me$_2$PhCH$_2$SO$_2$DPEN and 0.61 mg (1.0 µmol) of [RuCl$_2$(p-cymene)]$_2$ were used as the catalyst. GC analysis of the reaction product confirmed that 1-(3',5'-bis(trifluoromethyl)phenyl)ethanol with 93.7% ee optical purity was produced at 100% yield. Comparison with Comparative example C-102 indicated the superiority of this complex. In addition, superiority of (S,S)-2',6'-Me$_2$PhCH$_2$SO$_2$DPEN was also confirmed.

Comparative Example D-1

Asymmetric Reduction of 2',5'-dimethylacetophenone by Ru(OTf)[(S,S)-Tsdpen](p-cymene) Complex Using Potassium Formate Solution as Hydrogen Source (Comparison of Catalyst)

In a 20-mL Schlenk tube, 505 mg (6.0 mmol) of HCOOK as a hydrogen source, 9.66 mg (30 µmol) of tetra-n-butylammonium bromide as a phase-transfer catalyst, and 2.25 mg (3.0 µmol) of Ru(OTf)[(S,S)-Tsdpen](p-cymene) as a catalyst were introduced and subjected to argon-gas replacement. 445 µL (3.0 mmol) of 2',5'-dimethylacetophenone and 0.6 mL of water were added and stirred at 50° C. for 24 hr. The organic phase was washed 3 times with 3 mL of water to give an optically-active alcohol. GC analysis of the reaction product confirmed that 1-(2',5'-dimethylphenyl)ethanol with 72.9% ee optical purity was produced at 95% yield.

Comparative Example D-2

Asymmetric Reduction of 2',5'-dimethylacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example D-1, except that 2.43 mg (3.0 µmol) of Ru(OTf)[(R)—Cs—(R,R)-dpen](p-cymene) was used as the catalyst. GC analysis of the reaction product confirmed that 1-(2',5'-dimethylphenyl)ethanol with 73.2% ee optical purity was produced at 95% yield.

Example D-6

Asymmetric Reduction of 2',5'-dimethylacetophenone by RuCl[(S,S)—($C_2H_5$)$_2$CHCH$_2$SO$_2$dpen](p-cymene) Complex Using Potassium Formate Solution as Hydrogen Source The reaction was carried out with the same conditions as in Comparative example D-1, except that 1.89 mg (3.0 µmol) of RuCl[(S,S)—($C_2H_5$)$_2$CHCH$_2$SO$_2$dpen](p-cymene) was used as the catalyst. GC analysis of the reaction product confirmed that 1-(2',5'-dimethylphenyl)ethanol with 91.8% ee optical purity was produced at 100% yield. Comparison with Comparative examples D-1 and D-2 indicated the superiority of this complex.

Example D-7

Asymmetric Reduction of 2',5'-dimethylacetophenone by RuCl[(S,S)-2',6'-Me$_2$PhCH$_2$SO$_2$dpen](p-cymene) Complex Using Potassium Formate Solution as Hydrogen Source The reaction was carried out with the same conditions as in Comparative example D-1, except that 1.99 mg (3.0 µmol) of RuCl[(S,S)-2',6'-Me$_2$PhCH$_2$SO$_2$dpen](p-cymene) was used as the catalyst. GC analysis of the reaction product confirmed that 1-(2',5'-dimethylphenyl)ethanol with 92.9% ee optical purity was produced at 100% yield. Comparison with Comparative examples D-1 and D-2 indicated the superiority of this complex.

Comparative Example D-102

Asymmetric Reduction of 2',5'-dimethylacetophenone by Catalyst Comprising (R)—Cs—(R,R)-DPEN and [RuCl$_2$(p-cymene)]$_2$ Using Mixture of Formic Acid/Triethylamine as Hydrogen Source The reaction was carried out with the same conditions as in Comparative example D-1, except that 1.28 mg (3.0 µmol) of (R)—Cs—(R,R)-DPEN and 0.92 mg (1.5 µmol) of [RuCl$_2$(p-cymene)]$_2$ were used as the catalyst, and 351 µL (9.3 mmol) of formic acid and 1.09 mL (7.8 mmol) of triethylamine were used as the hydrogen source. GC analysis of the reaction product confirmed that 1-(2',5'-dimethylphenyl)ethanol with 73.7% ee optical purity was produced at 38% yield.

Example D-107

Asymmetric Reduction of 2',5'-dimethylacetophenone by Catalyst Comprising (S,S)-2',6'-Me$_2$PhCH$_2$SO$_2$DPEN and [RuCl$_2$(p-cymene)]$_2$ Using Mixture of Formic Acid/Triethylamine as Hydrogen Source The reaction was carried out with the same conditions as in Comparative example D-102, except that 1.18 mg (3.0 µmol) of (S,S)-2',6'-Me$_2$PhCH$_2$SO$_2$DPEN and 0.92 mg (1.5 µmol) of [RuCl$_2$(p-cymene)]$_2$ were used as, the catalyst. GC analysis of the reaction product confirmed that 1-(2',5'-dimethylphenyl)ethanol with 93.3% ee optical purity was produced at 61% yield. Comparison with Comparative example C-102 indicated the superiority of this complex. In addition, superiority of (S,S)-2',6'-Me$_2$PhCH$_2$SO$_2$DPEN was also confirmed.

Comparative Example E-1

Asymmetric Reduction of 3'-trifluoromethylacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 µmol) of tetra-n-butylammonium bromide as a phase-transfer catalyst, and 0.75 mg (1.0 µmol) of (Ru(OTf)[(S,S)-Tsdpen](p-cymene) as a catalyst were introduced and subjected to argon-gas replacement. 747 µL (5.0 mmol) of 3'-trifluoromethylacetophenone and 1 mL of water were added and stirred at 50° C. for 24 hr. The organic phase was washed 3 times with 3 mL of water to give an optically-active alcohol. GC analysis of the reaction product confirmed that 1-(3'-trifluoromethylphenyl)ethanol with 90.0% ee optical purity was produced at 100% yield.

Comparative Example E-2

Asymmetric Reduction of 3'-trifluoromethylacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example E-1, except that 0.81 mg (1.0 µmol) of Ru(OTf)[(R)—Cs—(R,R)-dpen](p-cymene) was used as the catalyst. GC analysis of the reaction product confirmed that 1-(3'-trifluoromethylphenyl)ethanol with 93.4% ee optical purity was produced at 100% yield.

Example E-6

Asymmetric Reduction of 3'-trifluoromethylacetophenone by RuCl[(S,S)—(C$_2$H$_5$)$_2$CHCH$_2$SO$_2$dpen](p-cymene) Complex Using Potassium Formate Solution as Hydrogen Source The reaction was carried out with the same conditions as in Comparative example E-1, except that 0.63 mg (1.0 µmol) of RuCl[(S,S)—(C$_2$H$_5$)$_2$CHCH$_2$SO$_2$dpen](p-cymene) was used as the catalyst. GC analysis of the reaction product confirmed that 1(3'-trifluoromethylphenyl)ethanol with 93.5% ee optical purity was produced at 99% yield. Comparison with Comparative examples E-1 and E-2 indicated the superiority of this complex.

Example E-7

Asymmetric Reduction of 3'-trifluoromethylacetophenone by RuCl[(S,S)-2',6'-Me$_2$PhCH$_2$SO$_2$dpen](p-cymene) Complex Using Potassium Formate Solution as Hydrogen Source The reaction was carried out with the same conditions as in Comparative example E-1, except that 1.99 mg (3.0 µmol) of RuCl[(S,S)-2',6'-Me$_2$PhCH$_2$SO$_2$dpen](p-cymene) was used as the catalyst. GC analysis of the reaction product confirmed that 1-(3'-trifluoromethylphenyl)ethanol with 93.7% ee optical purity was produced at 100% yield. Comparison with Comparative examples E-1 and E-2 indicated the superiority of this complex.

Comparative Example E-9

Asymmetric Reduction of 3'-trifluoromethylacetophenone by Cp*Ir(OTf)[(S)—Cs—(S,S)-dpen] Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 µmol) of tetra-n-butylammonium bromide as a phase-transfer catalyst, and 0.92 mg (1.0 µmol) of Cp*Ir(OTf)[(S)—Cs—(S,S)-dpen] as a catalyst were introduced and subjected to argon-gas replacement. 747 μL (5.0 mmol) of 3'-trifluoromethylacetophenone and 1 mL of water were added and stirred at 50° C. for 24 hr. The organic phase was washed 3 times with 3 mL of water to give an optically-active alcohol. GC analysis of the reaction product confirmed that 1-(3'-trifluoromethylphenyl) ethanol with 92.0% ee optical purity was produced at 100% yield.

Example E-10

Asymmetric Reduction of 3'-trifluoromethylacetophenone by Cp*IrCl[(S,S)—($C_2H_5$)$_2$CHCH$_2$SO$_2$dpen] Complex Using Potassium Formate Solution as Hydrogen Source The reaction was carried out with the same conditions as in Comparative example E-9, except that 0.72 mg (1.0 μmol) of Cp*IrCl[(S,S)—($C_2H_5$)$_2$CHCH$_2$SO$_2$dpen] was used as the catalyst. GC analysis of the reaction product confirmed that 1-(3'-trifluoromethylphenyl)ethanol with 94.3% ee optical purity was produced at 100% yield. Comparison with Comparative example E-9 indicated the superiority of this complex.

Comparative Example F-1

Asymmetric Reduction of 4'-trifluoromethylacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 μmol) of tetra-n-butylammonium bromide as a phase-transfer catalyst, and 0.53 mg (0.71 μmol) of Ru(OTf)[(S,S)-Tsdpen](p-cymene) as a catalyst were introduced and subjected to argon-gas replacement. 747 μL (5.0 mmol) of 4'-trifluoromethylacetophenone and 1 mL of water were added and stirred at 50° C. for 24 hr. The organic phase was washed 3 times with 3 mL of water to give an optically-active alcohol. GC analysis of the reaction product confirmed that 1-(4'-trifluoromethylphenyl)ethanol with 91.9% ee optical purity was produced at 94% yield.

Comparative Example F-2

Asymmetric Reduction of 4'-trifluoromethylacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example F-1, except that 0.57 mg (0.71 μmol) of Ru(OTf)[(R)—Cs—(R,R)-dpen](p-cymene) was used as the catalyst. GC analysis of the reaction product confirmed that 1-(4'-trifluoromethylphenyl)ethanol with 94.8% ee optical purity was produced at 68% yield.

Example F-6

Asymmetric Reduction of 4'-trifluoromethylacetophenone by RuCl[(S,S)—($C_2H_5$)$_2$CHCH$_2$SO$_2$dpen](p-cymene) Complex Using Potassium Formate Solution as Hydrogen Source The reaction was carried out with the same conditions as in Comparative example F-1, except that 0.45 mg (0.71 μmol) of RuCl[(S,S)—($C_2H_5$)$_2$CHCH$_2$SO$_2$dpen](p-cymene) was used as the catalyst. GC analysis of the reaction product confirmed that 1-(4'-trifluoromethylphenyl)ethanol with 94.9% ee optical purity was produced at 61% yield. Comparison with Comparative examples F-1 and F-2 indicated the superiority of this complex.

Example F-7

Asymmetric Reduction of 4'-trifluoromethylacetophenone by RuCl[(S,S)-2',6'-Me$_2$PhCH$_2$SO$_2$dpen](p-cymene) Complex Using Potassium Formate Solution as Hydrogen Source The reaction was carried out with the same conditions as in Comparative example F-1, except that 0.47 mg (0.71 μmol) of RuCl[(S,S)-2',6'-Me$_2$PhCH$_2$SO$_2$dpen](p-cymene) was used as the catalyst. GC analysis of the reaction product confirmed that 1-(4'-trifluoromethylphenyl)ethanol with 94.6% ee optical purity was produced at 100% yield. Comparison with Comparative examples F-1 and F-2 indicated the superiority of this complex.

Comparative Example F-9

Asymmetric Reduction of 4'-trifluoromethylacetophenone by Cp*Ir(OTf)[(S)—Cs—(S,S)-dpen] Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 μmol) of tetra-n-butylammonium bromide as a phase-transfer catalyst, and 0.65 mg (0.71 μmol) of Cp*Ir(OTf)[(S)—Cs—(S,S)-dpen] as a catalyst were introduced and subjected to argon-gas replacement. 747 μL (5.0 mmol) of 4'-trifluoromethylacetophenone and 1 mL of water were added and stirred at 50° C. for 24 hr. The organic phase was washed 3 times with 3 mL of water to give an optically-active alcohol. GC analysis of the reaction product confirmed that 1-(4'-trifluoromethylphenyl)ethanol with 93.6% ee optical purity was produced at 100% yield.

Example F-10

Asymmetric Reduction of 4'-trifluoromethylacetophenone by Cp*IrCl[(S,S)—($C_2H_5$)$_2$CHCH$_2$SO$_2$dpen] Complex Using Potassium Formate Solution as Hydrogen Source The reaction was carried out with the same conditions as in Comparative example F-9, except that 0.51 mg (0.71 μmol) of Cp*IrCl[(S,S)—($C_2H_5$)$_2$CHCH$_2$SO$_2$dpen] was used as the catalyst. GC analysis of the reaction product confirmed that 1-(4'-trifluoromethylphenyl)ethanol with 95.9% ee optical purity was produced at 100% yield. Comparison with Comparative example F-9 indicated the superiority of this complex.

Comparative Example G-1

Asymmetric Reduction of 3',4'-dichloroacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 μmol) of tetra-n-butylammonium bromide as a phase-transfer catalyst, and 0.53 mg (0.71 µmol) of Ru(OTf)[(S,S)-Tsdpen](p-cymene) as a catalyst were introduced and subjected to argon-gas replacement. 945 mg (5.0 mmol) of 3',4'-dichloroacetophenone, 1 mL of water and 1 mL of ethyl acetate were added and stirred at 50° C. for 24 hr. The organic phase was washed 3 times with 3 mL of water to give an optically-active alcohol. GC analysis of the reaction product confirmed that 1-(3',4'-dichlorophenyl)ethanol with 87.8% ee optical purity was produced at 100% yield.

Comparative Example G-2

Asymmetric Reduction of 3',4'-dichloroacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example G-1, except that 0.57 mg (0.71 µmol) of Ru(OTf)[(R)—Cs—(R,R)-dpen](p-cymene) was used as the catalyst. GC analysis of the reaction product confirmed that 1-(3',4'-dichlorophenyl)ethanol with 92.9% ee optical purity was produced at 94% yield.

Example G-6

Asymmetric Reduction of 3',4'-dichloroacetophenone by RuCl[(S,S)—$(C_2H_5)_2CHCH_2SO_2$dpen](p-cymene) Complex Using Potassium Formate Solution as Hydrogen Source The reaction was carried out with the same conditions as in Comparative example G-1, except that 0.45 mg (0.71 µmol) of RuCl[(S,S)—$(C_2H_5)_2CHCH_2SO_2$dpen](p-cymene) was used as the catalyst. GC analysis of the reaction product confirmed that 1-(3',4'-dichlorophenyl)ethanol with 92.5% ee optical purity was produced at 100% yield. Comparison with Comparative examples G-1 and G-2 indicated the superiority of this complex.

Comparative Example H-1

Asymmetric Reduction of 2'-nitroacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 µmol) of tetra-n-butylammonium bromide as a phase-transfer catalyst, and 1.25 mg (1.67 µmol) of Ru(OTf)[(S,S)-Tsdpen](p-cymene) as a catalyst were introduced and subjected to argon-gas replacement. 826 mg (5.0 mmol) of 2'-nitroacetophenone and 1 mL of water were added and stirred at 50° C. for 24 hr. The organic phase was washed 3 times with 3 mL of water to give an optically-active alcohol. GC analysis of the reaction product confirmed that 1-(2'-nitrophenyl)ethanol with 86.7% ee optical purity was produced at 46% yield.

Comparative Example H-2

Asymmetric Reduction of 2'-nitroacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example H-1, except that 1.35 mg (1.67 µmol) of Ru(OTf)[(R)—Cs—(R,R)-dpen](p-cymene) was used as the catalyst. GC analysis of the reaction product confirmed that 1-(2'-nitrophenyl)ethanol with 93.0% ee optical purity was produced at 37% yield.

Example H-6

Asymmetric Reduction of 2'-nitroacetophenone by RuCl[(S,S)—$(C_2H_5)_2CHCH_2SO_2$dpen](p-cymene) Complex Using Potassium Formate Solution as Hydrogen Source The reaction was carried out with the same conditions as in Comparative example H-1, except that 1.05 mg (1.67 µmol) of RuCl[(S,S)—$(C_2H_5)_2CHCH_2SO_2$dpen](p-cymene) was used as the catalyst. GC analysis of the reaction product confirmed that 1-(2'-nitrophenyl)ethanol with 93.0% ee optical purity was produced at 48% yield. Comparison with Comparative examples H-1 and H-2 indicated the superiority of this complex.

Comparative Example I-1

Asymmetric Reduction of 3'-nitroacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 µmol) of tetra-n-butylammonium bromide as a phase-transfer catalyst, and 0.75 mg (1.0 µmol) of Ru(OTf)[(S,S)-Tsdpen](p-cymene) as a catalyst were introduced and subjected to argon-gas replacement. 826 mg (5.0 mmol) of 3'-nitroacetophenone, 1 mL of water and 1 mL of ethyl acetate were added and stirred at 50° C. for 24 hr. The organic phase was washed 3 times with 3 mL of water to give an optically-active alcohol. GC analysis of the reaction product confirmed that 1-(3'-nitrophenyl)ethanol with 75.8% ee optical purity was produced at 64% yield.

Comparative example I-2

Asymmetric Reduction of 3'-nitroacetophenone by Ru(OTf)[(R)—Cs—(R,R)-dpen] (p-cymene) Complex Using Potassium Formate Solution as Hydrogen Source (Comparison of Catalyst)

The reaction was carried out with the same conditions as in Comparative example I-1, except that 0.81 mg (1.0 µmol) of Ru(OTf)[(R)—Cs—(R,R)-dpen](p-cymene) was used as the catalyst. GC analysis of the reaction product confirmed that 1-(3'-nitrophenyl)ethanol with 84.5% ee optical purity was produced at 68% yield.

Example I-6

Asymmetric Reduction of 3'-nitroacetophenone by RuCl[(S,S)—$(C_2H_5)_2CHCH_2SO_2$dpen](p-cymene) Complex Using Potassium Formate Solution as Hydrogen Source The reaction was carried out with the same conditions as in Comparative example I-1, except that 0.63 mg (1.0 µmol) of RuCl[(S,S)—$(C_2H_5)_2CHCH_2SO_2$dpen](p-cymene) was used as the catalyst. GC analysis of the reaction product confirmed that 1-(3'-nitrophenyl)ethanol with 85.4% ee optical purity was produced at 65% yield. Comparison with Comparative examples I-1 and I-2 indicated the superiority of this complex.

Comparative Example J-1

Asymmetric Reduction of 4'-cyanoacetophenone by Ru(OTf)[(S,S)-Tsdpen](p-cymene) Complex Using Potassium Formate Solution as Hydrogen Source (Comparison of Catalyst)

In a 20-mL Schlenk tube, 0.84 g (10.0 mmol) of HCOOK as a hydrogen source, 16.1 mg (50 µmol) of tetra-n-butylammonium bromide as a phase-transfer catalyst, and 0.75 mg (1.0 µmol) of Ru(OTf)[(S,S)-Tsdpen](p-cymene) as a catalyst were introduced and subjected to argon-gas replacement. 826 mg (5.0 mmol) of 4'-cyanoacetophenone, 1 mL of water and 1 mL of ethyl acetate were added and stirred at 50° C. for 2.4 hr. The organic phase was washed 3 times with 3 mL of water to give an optically-active alcohol. GC analysis of the reaction product confirmed that 1-(4'-cyanophenyl)ethanol with 84.5% ee optical purity was produced at 100% yield.

Comparative Example J-2

Asymmetric Reduction of 4'-cyanoacetophenone by Ru(OTf)[(R)—Cs—(R,R)-dpen](p-cymene) Complex Using Potassium Formate Solution as Hydrogen Source (Comparison of Catalyst)

The reaction was carried out with the same conditions as in Comparative example J-1, except that 0.81 mg (1.0 µmol) of Ru(OTf)[(R)—Cs—(R,R)-dpen](p-cymene) was used as the catalyst. GC analysis of the reaction product confirmed that 1-(4'-cyanophenyl)ethanol with 90.7% ee optical purity was produced at 71% yield.

Example J-6

Asymmetric Reduction of 4'-cyanoacetophenone by RuCl[(S,S)—($C_2H_5$)$_2$CHCH$_2$SO$_2$dpen](p-cymene) Complex Using Potassium Formate Solution as Hydrogen Source The reaction was carried out with the same conditions as in Comparative example J-1, except that 0.63 mg (1.0 µmol) of RuCl[(S,S)—($C_2H_5$)$_2$CHCH$_2$SO$_2$dpen](p-cymene) was used as the catalyst. GC analysis of the reaction product confirmed that 1-(4'-cyanophenyl)ethanol with 89.4% ee optical purity was produced at 100% yield. Comparison with Comparative examples J-1 and J-2 indicated the superiority of this complex.

The invention claimed is:

1. An organic metal compound of general formula (1):

(Chem. 1)

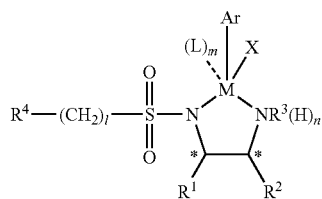

(1)

wherein in general formula (1), $R^1$ and $R^2$ are a mutually identical or mutually different, unsubstituted or substituted alkyl group, aryl group, cycloalkyl group, or heterocyclic group, or $R^1$ and $R^2$ are bound to form an alicyclic ring, $R^3$ is a hydrogen atom or an alkyl group, $R^4$ is an alkyl group that is branched or that does or does not form a ring by itself, an unsubstituted or substituted aryl group, or an unsubstituted or substituted heterocyclic group, Ar is an unsubstituted or substituted cyclopentadienyl group that is bound to M via a π bond, or an unsubstituted or substituted benzene, X is a hydride group or an anionic group, M is ruthenium, rhodium or iridium, L is a solvent molecule or a water molecule, l is 1 or 2, m is an integer from 0 to 2, n is 0 or 1, and when n is 0, X does not exist, and * represents asymmetric carbon, wherein $R^4$ is not a camphor group, a camphor derivative group, an isopropyl group or a phenyl group whenever $R^1$ and $R^2$ are both a phenyl group.

2. The organic metal compound according to claim 1, wherein in general formula (1), $R^4$ is an unsubstituted or substituted aryl group, or an unsubstituted or substituted heterocyclic group.

3. The organic metal compound according to claim 1, wherein in general formula (1), M is ruthenium and Ar is an unsubstituted or substituted benzene.

4. The organic metal compound according to claim 1, wherein in general formula (1), M is iridium and Ar is an unsubstituted or substituted cyclopentadienyl group.

5. The organic metal compound according to claim 1, wherein in general formula (1), $R^3$ is a hydrogen atom, n is 1, and X is a sulfonate group.

6. The organic metal compound according to claim 1, wherein in general formula (1), $R^3$ is a hydrogen atom, n is 1, and X is a halogen atom.

7. A compound of general formula (2):

(Chem. 2)

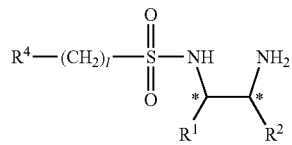

(2)

wherein in general formula (2), $R^1$ and $R^2$ are a mutually identical or mutually different, unsubstituted or substituted alkyl group, aryl group, or cycloalkyl group, or $R^1$ and $R^2$ are bound to form an alicyclic ring, $R^4$ is an unsubstituted or substituted C4-C15 alkyl group that is branched or that does or does not form a ring by itself, and that does not have a multiple bond and a hetero atom, or an unsubstituted or substituted aryl group, or an unsubstituted or substituted heterocyclic group, l is 1 or 2, * represents asymmetric carbon, wherein $R^4$ is not a camphor group, a camphor derivative group, an isopropyl group or a phenyl group whenever $R^1$ and $R^2$ are both a phenyl group.

8. The compound according to claim 7, wherein in general formula (2), $R^4$ is an unsubstituted or substituted aryl group, or an unsubstituted or substituted heterocyclic group.

9. A catalyst comprising a compound of general formula (2):

(Chem. 3)

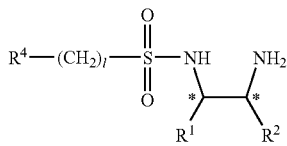
(2)

wherein in general formula (2), $R^1$ and $R^2$ are a mutually identical or mutually different, unsubstituted or substituted alkyl group, aryl group, or cycloalkyl group, or $R^1$ and $R^2$ are bound to form an alicyclic ring, $R^4$ is an unsubstituted or substituted C4-C15 alkyl group that is branched or that does or does not form a ring by itself, and that does not have a multiple bond and a hetero atom, or an unsubstituted or substituted aryl group, or an unsubstituted or substituted heterocyclic group, l is 1 or 2, * represents asymmetric carbon, wherein $R^4$ is not a camphor group, a camphor derivative group, an isopropyl group or a phenyl group whenever $R^1$ and $R^2$ are both a phenyl group, and an organic metal compound of general formula (3):

$$(ArMX_2)_2 \quad (3)$$

wherein in general formula (3), Ar is an unsubstituted or substituted cyclopentadienyl group that is bound to M via a π bond, or an unsubstituted or substituted benzene, X is a hydride group or an anionic group, M is ruthenium, rhodium or iridium.

10. The catalyst according to claim 9, wherein in general formula (2), $R^4$ is an unsubstituted or substituted aryl group, or an unsubstituted or substituted heterocyclic group.

11. A process for preparing optically active alcohols, wherein a ketone substrate and a hydrogen donor are reacted under the presence of the organic metal compound of general formula (1):

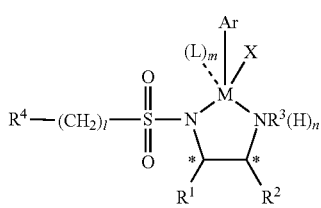
(1)

wherein in general formula (1), $R^1$ and $R^2$ are a mutually identical or mutually different, unsubstituted or substituted alkyl group, aryl group, cycloalkyl group, or heterocyclic group, or $R^1$ and $R^2$ are bound to form an alicyclic ring, $R^3$ is a hydrogen atom or an alkyl group, $R^4$ is an alkyl group that is branched or that does or does not form a ring by itself, an unsubstituted or substituted aryl group, or an unsubstituted or substituted heterocyclic group, Ar is an unsubstituted or substituted cyclopentadienyl group that is bound to M via a π bond, or an unsubstituted or substituted benzene, X is a hydride group or an anionic group, M is ruthenium, rhodium or iridium, L is a solvent molecule or a water molecule, l is 1 or 2, m is an integer from 0 to 2, n is 0 or 1, and when n is 0, X does not exist, and * represents asymmetric carbon, wherein $R^4$ is not a camphor group, a camphor derivative group, an isopropyl group or a phenyl group whenever $R^1$ and $R^2$ are both a phenyl group.

12. A process for preparing optically active alcohols, wherein a ketone substrate and a hydrogen donor are reacted under the presence of a catalyst comprising the organic compound of general formula (2):

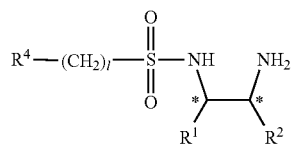
(2)

wherein in general formula (2), $R^1$ and $R^2$ are a mutually identical or mutually different, unsubstituted or substituted alkyl group, aryl group, or cycloalkyl group, or $R^1$ and $R^2$ are bound to form an alicyclic ring, $R^4$ is an unsubstituted or substituted C4-C15 alkyl group that is branched or that does or does not form a ring by itself, and that does not have a multiple bond and a hetero atom, or an unsubstituted or substituted aryl group, or an unsubstituted or substituted heterocyclic group, l is 1 or 2, * represents asymmetric carbon, wherein $R^4$ is not a camphor group, a camphor derivative group, an isopropyl group or a phenyl group whenever $R^1$ and $R^2$ are both a phenyl group, and the organic metal compound of general formula (3):

$$(ArMX_2)_2 \quad (3)$$

wherein in general formula (3), Ar is an unsubstituted or substituted cyclopentadienyl group that is bound to M via a π bond, or an unsubstituted or substituted benzene, X is a hydride group or an anionic group, M is ruthenium, rhodium or iridium.

13. The process according to claim 11, wherein hydrogen gas is used as the hydrogen donor.

14. The process according to claim 12, wherein hydrogen gas is used as the hydrogen donor.

15. The process according to claim 11, wherein a mixture of formic acid and organic amine is used as the hydrogen donor.

16. The process according to claim 12, wherein a mixture of formic acid and organic amine is used as the hydrogen donor.

17. The process according to claim 11, wherein a formate is used as the hydrogen donor and in addition, water or water/organic solvent is used as the solvent.

18. The process according to claim 12, wherein a formate is used as the hydrogen donor and in addition, water or water/organic solvent is used as the solvent.

19. The process according to claim 17, wherein a phase-transfer catalyst is further added.

20. The process according to claim 18, wherein a phase-transfer catalyst is further added.

21. The process according to claim 11, wherein an aromatic ketone having a substituent at 2'-position of the benzene ring is used as the substrate.

22. The process according to claim 12, wherein an aromatic ketone having a substituent at 2'-position of the benzene ring is used as the substrate.

23. The process according to claim 11, wherein an aromatic ketone having a plurality of substituents in the benzene ring is used as the substrate.

24. The process according to claim 12, wherein an aromatic ketone having a plurality of substituents in the benzene ring is used as the substrate.

25. The process according to claim 11, wherein bis(trifluoromethyl)acetophenone is used as the substrate.

26. The process according to claim 12, wherein bis(trifluoromethyl)acetophenone is used as the substrate.

27. The process according to claim 11, wherein 3',5'-bis(trifluoromethyl)acetophenone is used as the substrate.

28. The process according to claim 12, wherein 3',5'-bis(trifluoromethyl)acetophenone is used as the substrate.

* * * * *